United States Patent
Kolluri et al.

(10) Patent No.: US 12,110,285 B2
(45) Date of Patent: *Oct. 8, 2024

(54) SUBSTITUTED PYRIDINE DERIVATIVES AS SARM1 INHIBITORS

(71) Applicant: Nura Bio, Inc., South San Francisco, CA (US)

(72) Inventors: Rao Kolluri, San Francisco, CA (US); Christopher Michael Tegley, San Carlos, CA (US); Liusheng Zhu, Foster City, CA (US); Sean Pomeroy Brown, Half Moon Bay, CA (US); Charles Howard Reynolds, Austin, TX (US); Andrew Stewart Tasker, Simi Valley, CA (US); Cheryl A. Grice, Castle Rock, CO (US)

(73) Assignee: NURA BIO, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/178,325

(22) Filed: Mar. 3, 2023

(65) Prior Publication Data
US 2023/0286941 A1    Sep. 14, 2023

Related U.S. Application Data

(62) Division of application No. 17/875,301, filed on Jul. 27, 2022, now Pat. No. 11,629,136.

(60) Provisional application No. 63/368,034, filed on Jul. 8, 2022, provisional application No. 63/305,103, filed on Jan. 31, 2022, provisional application No. 63/226,557, filed on Jul. 28, 2021.

(51) Int. Cl.
*C07D 401/06*   (2006.01)
*C07D 417/14*   (2006.01)

(52) U.S. Cl.
CPC ......... *C07D 401/06* (2013.01); *C07D 417/14* (2013.01)

(58) Field of Classification Search
CPC .......................... C07D 401/06; C07D 417/14
USPC ......................................................... 514/341
See application file for complete search history.

(56) References Cited

U.S. PATENT DOCUMENTS

| | | | |
|---|---|---|---|
| 11,629,136 B1 * | 4/2023 | Kolluri | C07D 417/14 514/341 |
| 11,970,481 B1 | 4/2024 | Kozak et al. | |
| 2004/0186129 A1 | 9/2004 | Koya et al. | |
| 2006/0252778 A1 | 11/2006 | Guo et al. | |
| 2017/0197981 A1 | 7/2017 | Shaw et al. | |
| 2017/0355708 A1 | 12/2017 | Jefson et al. | |
| 2022/0056013 A1 | 2/2022 | Bosanac et al. | |
| 2022/0081417 A1 | 3/2022 | Brown et al. | |
| 2023/0105696 A1 | 4/2023 | Kolluri et al. | |
| 2023/0286978 A1 | 9/2023 | Bentley et al. | |
| 2023/0339913 A1 | 10/2023 | Kozak et al. | |

FOREIGN PATENT DOCUMENTS

| | | |
|---|---|---|
| WO | WO-9918096 A1 | 4/1999 |
| WO | WO-2005085220 A1 | 9/2005 |
| WO | WO-2005105780 A2 | 11/2005 |
| WO | WO-2009046802 A1 | 4/2009 |
| WO | WO-2009114552 A1 | 9/2009 |
| WO | WO-2010093849 A2 | 8/2010 |
| WO | WO-2012049161 A1 | 4/2012 |
| WO | WO-2012050141 A1 | 4/2012 |
| WO | WO-2014158998 A1 | 10/2014 |
| WO | WO-2014187928 A1 | 11/2014 |
| WO | WO-2015140130 A1 | 9/2015 |
| WO | WO-2016012474 A1 | 1/2016 |
| WO | WO-2016187324 A1 | 11/2016 |
| WO | WO-2018094362 A1 | 5/2018 |
| WO | WO-2019236890 A1 | 12/2019 |
| WO | WO-2020176863 A1 | 9/2020 |
| WO | WO-2020247701 A2 | 12/2020 |
| WO | WO-2020252229 A2 | 12/2020 |
| WO | WO-2021142006 A1 | 7/2021 |
| WO | WO-2022031736 A1 | 2/2022 |
| WO | WO-2022046606 A1 | 3/2022 |
| WO | WO-2022060812 A1 | 3/2022 |
| WO | WO-2023009663 A1 | 2/2023 |
| WO | WO-2024026368 A1 | 2/2024 |

OTHER PUBLICATIONS

Berge et al. Pharmaceutical Salts. Journal of Pharmaceutical Sciences 66(1):1-19 (Jan. 1977).
Bosanac et al., Pharmacological SARM1 inhibition protects axon structure and function in paclitaxel-induced peripheral neuropathy. Brain 144(10):3226-3238 (2021).
Coleman et al. An 85-kb tandem triplication in the slow Wallerian degeneration (Wlds) mouse. PNAS USA 95(17):9985-90 (1998).
Essuman et al. The SARM1 Toll/Interleukin-1 Receptor Domain Possesses Intrinsic NAD + Cleavage Activity that Promotes Pathological Axonal Degeneration. Neuron 93(6):1334-43 (2017).
Flierl et al. Mouse closed head injury model induced by a weight-drop device. Na Protoc 4(9):1328-1337 (2009).
Geisler et al. Prevention of vincristine-induced peripheral neuropathy by genetic deletion of SARM1 in mice. Brain 139(Pt 12):3092-3108 (2016).
Gerdts et al. Axon Self-Destruction: New Links among SARM1, MAPKs, and NAD+ Metabolism. Neuron 89:449-60 (2016).
Gerdts et al. SARM1 activation triggers axon degeneration locally via $NAD^+$ destruction. Science 348(6233):453-57 (2015).

(Continued)

*Primary Examiner* — Kahsay Habte
(74) *Attorney, Agent, or Firm* — WILSON SONSINI GOODRICH & ROSATI

(57) ABSTRACT

This disclosure is drawn to pyridine derivatives, compositions thereof, and associated methods, useful for inhibition of SARM1 activity and/or for treating or preventing neurological disorders.

19 Claims, No Drawings

(56) References Cited

OTHER PUBLICATIONS

Henninger et al. Attenuated traumatic axonal injury and improved functional outcome after traumatic brain injury in mice lacking Sarm1. Brain 139(Pt 4):1094 (2016).
Hughes et al., Small molecule SARM1 inhibitors recapitulate the SARM1-/- phenotype and allow recovery of a metastable pool of axons fated to degenerate. Cell Rep. 34(1):108588 (2021).
Ishita et al. Synthesis and biological evaluation of aminothiazoles against Histoplasma capsula-tum and Cryptococcus neoformans. Bioorg Med Chem 26:2251-2261 (2018).
Kanamori et al. Retrograde and Wallerian axonal degeneration occur synchronously after retinal ganglion cell axotomy. Am. J. Pathol. 181(1):62-73 (2012).
Kurowska et al. Is Axonal Degeneration a Key Early Event in Parkinson's Disease? J. Parkinson's Dis. 6:703-07 (2016).
Lipinski. Bioisosteric Design of Conformationally Restricted Pyridyltriazole Histamine H2 Receptor Antagonists. J Med Chem 26(1):1-6 (1983).
Loring et al. Identification of the First Noncompetitive SARM1 Inhibitors. Bioorg Med Chem 28(18):115644 (2020).
Lyons et al. B cells are critical to induction of experimental allergic encephalomyelitis by protein but not by a short encephalitogenic peptide. Eur J of Immunology 29(11):3432-9 (1999).
PCT/US2021/044389 International Invitation to Pay Additional Fees dated Nov. 12, 2021.
PCT/US2021/044389 International Search Report and Written Opinion dated Jan. 10, 2022.
PCT/US2021/050426 International Search Report and Written Opinion dated Dec. 20, 2021.
PCT/US2022/038577 International Search Report and Written Opinion dated Nov. 17, 2022.
Ravin. Chapter 76: Preformulation. Remington's Pharmaceutical Sciences, 17th ed., Mack Publishing Company, Easton, Pa. (pp. 1409-1423) (1985).
Registry No. 1372613-10-9, File Registry on STN, entered STN May 3, 2012.
Registry No. 1372613-27-8, File Registry on STN, entered STN May 3, 2012.
Salvadores et al. Axonal Degeneration during Aging and Its Functional Role in Neurodegenerative Disorders. Front. Neurosci. 11:451 (2017).
Segapelo et al. Pyrazolylmethyl)amino-pyridine platinum (II) and gold (II) complexes. Syn-thesis, structures and evaluation as anti-cancer agents. Inorganic Chimica Acta 362(9):3314-3324 (2009).
Shi et al. Structural basis of SARM1 activation, substrate recognition, and inhibition by small molecules. Mol Cell 82(9):1643-1659 (2022).
Sprowl et al. Oxaliplatin-induced neurotoxicity is dependent on the organic cation transporter OCT2. PNAS USA 110(27):11199-11204 (2013).
Summers et al. Mitochondrial dysfunction induces Sarm1-dependent cell death in sensory neurons. J Neurosci. 34(28):9338-50 (2014).
Summers et al. SARM1-specific motifs in the TIR domain enable NAD+ loss and regulate injury-induced SARM1 activation. PNAS USA 113(41):E6271-E6280 (2016).
U.S. Appl. No. 17/475,896 Office Action dated Jan. 17, 2023.
U.S. Appl. No. 17/875,301 Office Action dated Nov. 8, 2022.
Wang et al. WldS mice are resistant to paclitaxel (taxol) neuropathy. Ann. Neurol. 52(4)442-7 (2002).
Yang et al. Pathological axonal death through a MAPK cascade that triggers a local energy deficit. Cell 160(1-2):161-76 (2015).
Bratkowski et al., Structural and mechanistic regulation of the pro-degenerative NAD hydrolase SARM1. Cell Rep. 32(5):107999 (2020).
Cavaletti et al., Chemotherapy-induced peripheral neurotoxicity: a multifaceted, still unsolved issue. J Peripher Nerv Syst. 24(Suppl 2):S6-S12 (2019).
Essuman et al., TIR domain proteins are an ancient family of NAD+-consuming enzymes. Curr Biol. 28(3):421-430.e4 (2018).
Figley et al., SARM1 is a metabolic sensor activated by an increased NMN/NAD+ ratio to trigger axon degeneration. Neuron 109(7):1118-1136.e11 (2021).
Fischer et al. Amyotrophic lateral sclerosis is a distal axonopathy: evidence in mice and man. Exp Neurol 185:232-240 (2004).
Fukuda et al., A mechanistic understanding of axon degeneration in chemotherapy-induced peripheral neuropathy. Front Neurosci. 11:481 (2017).
Gaetani et al., Neurofilament light chain as a biomarker in neurological disorders. J Neurol Neurosurg Psychiatry 90(8):870-881 (2019).
Gagliardi et al., Diagnostic and prognostic value of CSF neurofilaments in a cohort of patients with motor neuron disease: A cross-sectional study. J Cell Mol Med. 25(8):3765-3771 (2021).
Gerdts et al., Image-based screening identifies novel roles for IkappaB kinase and glycogen synthase kinase 3 in axonal degeneration. J Biol Chem. 286(32):28011-28018 (2011).
Gerdts et al., Sarm1-mediated axon degeneration requires both SAM and TIR interactions. J Neurosci. 33(33):13569-13580 (2013).
Gordon. Neurofilaments in disease: what do we know? Curr Opin Neurobiol. 61:105-115 (2020).
Graham et al., Diffuse axonal injury predicts neurodegeneration after moderate-severe traumatic brain injury. Brain 143(12):3685-3698 (2020).
Haffner et al., Discovery, synthesis, and biological evaluation of thiazoloquin(az)olin(on)es as potent CD38 inhibitors. J Med Chem. 58(8):3548-3571 (2015).
Horsefield et al., NAD+ cleavage activity by animal and plant TIR domains in cell death pathways. Science 365(6455):793-799 (2019).
Huang et al., Longitudinal biomarkers in amyotrophic lateral sclerosis. Ann Clin Transl Neurol. 7(7):1103-1116 (2020).
Jiang et al., The NAD+-mediated self-inhibition mechanism of pro-neurodegenerative SARM1. Nature 588(7839):658-663 (2020).
Kaneko et al., Protecting axonal degeneration by increasing nicotinamide adenine dinucleotide levels in experimental autoimmune encephalomyelitis models. J Neurosci. 26(38):9794-9804 (2006).
Kim et al., MyD88-5 links mitochondria, microtubules, and JNK3 in neurons and regulates neuronal survival. J Exp Med. 204(9):2063-2074 (2007).
Koliatsos et al., Wallerian degeneration as a therapeutic target in traumatic brain injury. Curr Opin Neurol. 32(6):786-795 (2019).
Ma et al., Direct pathogen-induced assembly of an NLR immune receptor complex to form a holoenzyme. Science 370(6521):eabe3069 (2020).
Maglemose et al., Potassium channel abnormalities are consistent with early axon degeneration of motor axons in the G127X SOD1 mouse model of amyotrophic lateral sclerosis. Exp Neurol. 292:154-167 (2017).
Martin et al., Structure of the activated ROQ1 resistosome directly recognizing the pathogen effector XopQ. Science 370(6521):eabd9993 (2020).
Osterloh et al., dSarm/Sarm1 is required for activation of an injury-induced axon death pathway. Science 337(6093):481-484 (2012).
Perry et al., Evidence that very slow wallerian degeneration in C57BL/Ola mice is an intrinsic property of the peripheral nerve. Eur J Neurosci. 2(9):802-808 (1990).
RCSB Protein Data Bank, 7NAI Crystal structure of the TIR domain from human SARM1 in complex with 3AD. https://www.rcsb.org/structure/7NAI (2021).
Sasaki et al., Nicotinamide mononucleotide adenylyl transferase-mediated axonal protection requires enzymatic activity but not increased levels of neuronal nicotinamide adenine dinucleotide. J Neurosci. 29(17):5525-5535 (2009).
Schlaepfer. Calcium-induced degeneration of axoplasm in isolated segments of rat peripheral nerve. Brain Res. 69(2):203-215 (1974).
Scully et al., Synthesis and evaluation of thiazoloquinolinones with linkers to enable targeting of CD38. ACS Med Chem Lett. 8(2):196-200 (2017).
Shen et al., Multiple domain interfaces mediate SARM1 autoinhibition. Proc Natl Acad Sci USA. 118(4):e2023151118 (2021).
Sporny et al., Structural basis for SARM1 inhibition and activation under energetic stress. Elife 9:e62021 (2020).

(56) References Cited

OTHER PUBLICATIONS

Tarrago et al., A Potent and Specific CD38 Inhibitor Ameliorates Age-Related Metabolic Dysfunction by Reversing Tissue NAD+ Decline. Cell Metab. 27(5):1081-1095.e10 (2018).
Uccellini et al., Passenger mutations confound phenotypes of SARM1-deficient mice. BioRxiv. Oct. 18, 2019; Cell Reports 31(1):107498 (2020).
Viar et al., Sarm1 knockout protects against early but not late axonal degeneration in experimental allergic encephalomyelitis. PLoS One 15(6):e0235110 (2020).
Waller. Experiments on the section of the glossopharyngeal and hypoglossal nerves of the frog, and observations of the alterations produced thereby in the structure of their primitive fibres. Philosophical Transactions of the Royal Society of London 140(0):423-429 (1850).
Weber et al., CLARITY reveals a more protracted temporal course of axon swelling and disconnection than previously described following traumatic brain injury. Brain Pathol. 29(3):437-450 (2019).
Williams et al., Neurofilaments in progressive multiple sclerosis: a systematic review. J Neurol. 268(9):3212-3222 (2021).
Zhao et al., A cell-permeant mimetic of NMN activates SARM1 to produce cyclic ADP-ribose and induce non-apoptotic cell death. iScience 15:452-466 (2019).
Cecil Textbook of Medicine, 20th edition (1996), vol. 2, pp. 1992-1996.
Cecil Textbook of Medicine, 20th edition (1996), vol. 2, pp. 2050-2057.
Chemical Abstracts STN Registry Database, Record for RN 2224489-34-1, Entered STN: May 21, 2018.
Co-pending U.S. Appl. No. 18/481,173, inventors Kozak; Jennifer et al., filed Oct. 4, 2023.
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html.
PCT/US2023/071058 International Search Report and Written Opinion dated Oct. 10, 2023.
U.S. Appl. No. 62/958,178, published by WIPO in International Application No. PCT/US2021/012333 on Jul. 15, 2021.
U.S. Appl. No. 17/475,896 Office Action dated Aug. 7, 2023.
U.S. Appl. No. 18/481,173 Notice of Allowance dated Feb. 6, 2024.
U.S. Appl. No. 18/481,173 Office Action dated Dec. 22, 2023.

\* cited by examiner

SUBSTITUTED PYRIDINE DERIVATIVES AS SARM1 INHIBITORS

CROSS-REFERENCE

This application is a Division of U.S. Ser. No. 17/875,301, filed on Jul. 27, 2022, which claims priority to U.S. Provisional Application Nos. 63/226,557, filed on Jul. 28, 2021, 63/305,103, filed on Jan. 31, 2022, and 63/368,034, filed on Jul. 8, 2022, each of which is incorporated by reference in its entirety.

FIELD OF THE INVENTION

This disclosure is drawn to compounds and compositions, and associated methods, useful for inhibition of SARM1 activity and/or for treating or preventing a neurological disorder.

BACKGROUND OF THE INVENTION

Aging constitutes the main risk factor for the development of neurodegenerative diseases. Axonal degeneration is an important pathological event in many neurodegenerative and neurological disorders, including peripheral neuropathy and traumatic brain injury (Gerdts, J. et al., Neuron, 2016, 89, 449-60). Axonal degeneration has also been implicated in, for example, Alzheimer's disease, Parkinson's disease, and Amyotrophic Lateral Sclerosis, where degeneration precedes symptom onset and widespread neuronal loss (Kurowska, Z. et al., J. Parkinson's Dis., 2016, 6, 703-07). While these neurological conditions have unique underlying etiologies, inhibition of axonal degeneration in the conditions' early stages may slow or prevent their progression by preventing the loss of functional synapses and maintaining neuronal connectivity (Essuman, K. et al., Neuron, 2017 Mar. 22, 93(6), 1334-43).

Axonal degeneration after injury occurs both toward the proximal cell body (termed retrograde degeneration) and toward the distal axon terminal (termed Wallerian or orthograde degeneration) (Kanamori A. et al., Am. J. Pathol. 2012 July; 181(1):62-73). Wallerian degeneration, which occurs in that section of the axon that is distal to the site of injury, occurs after axonal injury in both the peripheral nervous system (PNS) and the central nervous system (CNS). Wallerian degeneration usually begins within 24-36 hours of a lesion. Prior to degeneration, the distal section of the axon tends to remain electrically excitable, while after injury, the axonal skeleton disintegrates and the axonal membrane breaks apart.

The processes of death of the cell body and degeneration of the axon are independent events. As alluded to above, evidence exists indicating that the degeneration of axons precedes clinical symptoms in neurodegenerative diseases and occurs before cell body loss. Thus, axonal degeneration constitutes an early event in pathological processes and provides a potential therapeutic target to treat neurodegeneration prior to neuronal cell death (Salvadores, N. et al., Front. Neurosci., 2017, 11, 451).

In view of the above, new modalities are needed for the treatment of neurological disorders such as neurodegenerative disease by the prevention of axonal degeneration.

SUMMARY OF THE INVENTION

The present invention is directed to inhibitors of SARM1 such as a compound of Formula I:

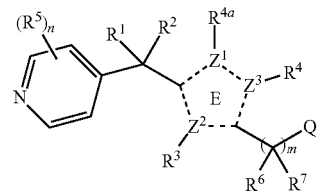

I or a pharmaceutically acceptable salt thereof, wherein constituent members are defined herein.

In one aspect described herein is a compound of Formula IIa, or a pharmaceutically acceptable salt thereof:

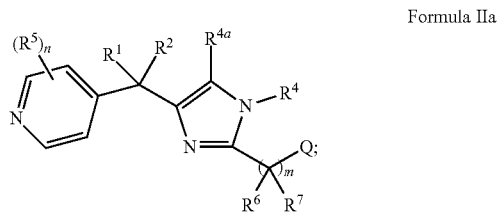

Formula IIa wherein:
Q is —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^4$ and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
$R^6$ and $R^7$ are each independently selected from H, —$OR^a$, —$NR^cR^d$, $C_{1-4}$ alkyl, and $C_{1-4}$ haloalkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^c R^d$, $NR^cR^d$, $NR^cC(O)R^b$, $NR^cC(O)OR^a$, $NR^cC(O)NR^c R^d$, $C(=NR^e)R^b$, $C(=NR^e)NR^cR^d$, $NR^cC(=NR^e)NR^c R^d$, $NR^cS(O)R^b$, $NR^cS(O)_2R^b$, $NR^cS(O)_2NR^cR^d$, $S(O) R^b$, $S(O)NR^cR^d$, $S(O)_2R^b$, and $S(O)_2NR^cR^d$;
each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;
each $R^e$ is independently selected from H, $C_{1-4}$ alkyl, and CN;
n is 0, 1, or 2; and
m is 1 or 2.

In some embodiments is a compound of Formula IIa, wherein R² is H or methyl. In some embodiments is a compound of Formula IIa, wherein R² is H. In some embodiments is a compound of Formula IIa, wherein R⁴ is H. In some embodiments is a compound of Formula IIa, wherein R⁴ᵃ is H. In some embodiments is a compound of Formula IIa, wherein R⁵ is H. In some embodiments is a compound of Formula IIa, wherein R⁶ and R⁷ are each independently selected from H and OH. In some embodiments is a compound of Formula IIa, wherein both R⁶ and R⁷ are H. In some embodiments is a compound of Formula IIa, wherein R⁶ is OH and R⁷ is H. In some embodiments is a compound of Formula IIa, wherein R⁶ is NRᶜRᵈ and R⁷ is H. In some embodiments is a compound of Formula IIa, wherein R⁷ is H. In some embodiments is a compound of Formula IIa, wherein Q is —CF₃, or C₁₋₄ alkyl-CF₃. In some embodiments is a compound of Formula IIa, wherein Q is —CF₃. In some embodiments is a compound of Formula IIa, wherein Q is —Cy or —C₁₋₄ alkyl-Cy. In some embodiments is a compound of Formula IIa, wherein Q is —Cy. In some embodiments is a compound of Formula IIa, wherein Cy is selected from C₆₋₁₀ aryl and 5-6 membered heteroaryl, each optionally substituted by 1, 2, 3, 4, or 5 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRᶜS(O)Rᵇ, NRᶜS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ. In some embodiments is a compound of Formula IIa, wherein Cy is selected from 5-6 membered heteroaryl optionally substituted by 1, 2, 3, or 4 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRᶜS(O)Rᵇ, NRᶜS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ. In some embodiments is a compound of Formula IIa, wherein Cy is selected from 5-membered heteroaryl optionally substituted by 1 or 2 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRᶜS(O)Rᵇ, NRᶜS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ. In some embodiments is a compound of Formula IIa, wherein Cy is thiazoyl optionally substituted by 1 or 2 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRᶜS(O)Rᵇ, NRᶜS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ. In some embodiments is a compound of Formula IIa, wherein Cy is unsubstituted thiazoyl. In some embodiments is a compound of Formula IIa, wherein Cy is

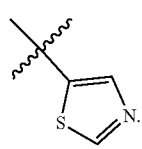 [SMILES: *c1cncs1]

In some embodiments is a compound of Formula IIa, wherein each R^Cy substituent is independently selected from halo, C₁₋₄ alkyl, C₁₋₄ haloalkyl, CN, ORᵃ, C(O)Rᵇ, C(O)NRᶜRᵈ, C(O)ORᵃ, NRᶜRᵈ, NRᶜC(O)Rᵇ, NRᶜS(O)₂Rᵇ, S(O)₂Rᵇ, and S(O)₂NRᶜRᵈ. In some embodiments is a compound of Formula IIa, wherein n is 0. In some embodiments is a compound of Formula IIa, wherein n is 1. In some embodiments is a compound of Formula IIa, wherein n is 2.

In another aspect described herein is a compound of Formula IV, or a pharmaceutically acceptable salt thereof:

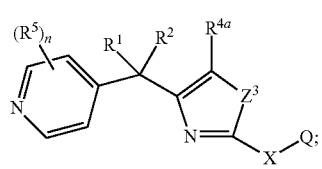

Formula IV wherein:
Z³ is S or N(R⁴);
Q is —Cy, —C₁₋₄ alkyl-Cy, —CF₃, or C₁₋₄ alkyl-CF₃;
X is —C(R⁶)(R⁷)—, —C(O)—, or —C(=N—OH)—;
R¹ is H;
R² is H or C₁₋₄ alkyl;
R⁴ and R⁴ᵃ are each independently selected from H, halo, and C₁₋₄ alkyl;
each R⁵ is independently selected from H, halo, and C₁₋₄ alkyl, wherein R⁵ is attached to a carbon atom;
R⁶ and R⁷ are each independently selected from H, —ORᵃ, —NRᶜRᵈ, C₁₋₄ alkyl, and C₁₋₄ haloalkyl;
Cy is selected from C₆₋₁₀ aryl, C₃₋₇ cycloalkyl, 5-6 membered heteroaryl, and 4-7 membered heterocycloalkyl, each optionally substituted by 1, 2, 3, 4, or 5 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRS(O)Rᵇ, NRS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ;
or two adjacent R^Cy substituents together with the atoms to which they are attached form a fused phenyl, C₃₋₇ cycloalkyl, 5-6 membered heteroaryl, or 4-7 membered heterocycloalkyl ring, each optionally substituted by 1, 2, 3, 4, or 5 substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRᶜS(O)Rᵇ, NRᶜS(O)₂Rᵇ, NRᶜS(O)₂NRᶜRᵈ, S(O)Rᵇ, S(O)NRᶜRᵈ, S(O)₂Rᵇ, and S(O)₂NRᶜRᵈ;
each Rᵃ, Rᵇ, Rᶜ, and Rᵈ is independently selected from H, C₁₋₄ alkyl, and C₁₋₄ haloalkyl, wherein said C₁₋₄ alkyl is optionally substituted with 1, 2, or 3 substituents independently selected from OH, CN, amino, halo, C₁₋₄ alkyl, C₁₋₄ alkoxy, C₁₋₄haloalkyl, and C₁₋₄haloalkoxy;
each Rᵉ is independently selected from H, C₁₋₄ alkyl, and CN; and
n is 0, 1, or 2.

In some embodiments is a compound of Formula IV, wherein X is —C(R⁶)(R⁷)—. In some embodiments is a compound of Formula IV, wherein X is —C(O)—.

In another aspect described herein is a compound of Formula IVa, or a pharmaceutically acceptable salt thereof:

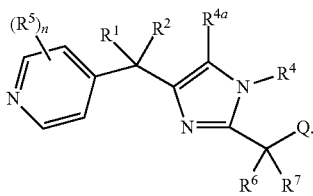

Formula IVa

In some embodiments is a compound of Formula IVa, wherein $R^4$ is H.

In another aspect described herein is a compound of Formula IVb, or a pharmaceutically acceptable salt thereof:

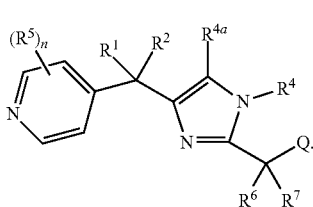

Formula IVb

In some embodiments is a compound of Formula IV, IVa, or IVb, wherein $R^2$ is H or methyl. In some embodiments is a compound of Formula IV, IVa, or IVb, wherein $R^2$ is H. In some embodiments is a compound of Formula IV, IVa, or IVb, wherein $R^{4a}$ is H. In some embodiments is a compound of Formula IV, IVa, or IVb, wherein $R^6$ and $R^7$ are each independently selected from H and OH. In some embodiments is a compound of Formula IV, IVa, or IVb, wherein at least one of $R^6$ and $R^7$ is H. In some embodiments is a compound of Formula IV, IVa, or IVb, wherein both $R^6$ and $R^7$ are H. In some embodiments is a compound of Formula IV, IVa, or IVb, wherein $R^6$ is OH and $R^7$ is H. In some embodiments is a compound of Formula IV, IVa, or IVb, wherein n is 0. In some embodiments is a compound of Formula IV, IVa, or IVb, wherein n is 1.

In another aspect described herein is a compound of Formula II, or a pharmaceutically acceptable salt thereof:

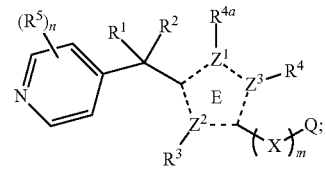

Formula II wherein:
$Z^1$, $Z^2$, and $Z^3$ are each independently selected from O, S, N, or C, wherein Ring E is a 5-membered aromatic ring;

Q is —CN, —$C_{1-4}$ alkyl-CN, —Cy, —$C_{1-4}$ alkyl-Cy, —$CF_3$, or $C_{1-4}$ alkyl-$CF_3$;

X is —C($R^6$)($R^7$)—, —C(O)—, or —C(=N—OH)—;

$R^1$ is H;

$R^2$ is H or $C_{1-4}$ alkyl;

$R^3$, $R^4$, and $R^{4a}$ are each independently selected from H, halo, and $C_{1-4}$ alkyl;

each $R^5$ is independently selected from H, halo, and $C_{1-4}$ alkyl, wherein $R^5$ is attached to a carbon atom;

wherein $R^3$ is absent when $Z^2$ is —O—, —S—, or —N=;

wherein $R^4$ is absent when $Z^3$ is —O—, —S—, or —N=;

wherein $R^{4a}$ is absent when $Z^1$ is —O—, —S—, or —N=;

$R^6$ and $R^7$ are each independently selected from H, —$OR^a$, —$NR^cR^d$, $C_{1-4}$ alkyl, and $C_{1-4}$ haloalkyl;

Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ haloalkyl, and $C_{1-4}$ haloalkoxy;

each $R^e$ is independently selected from H, $C_{1-4}$ alkyl, and CN;

n is 0, 1, or 2; and m is 1 or 2, wherein the compound is other than:

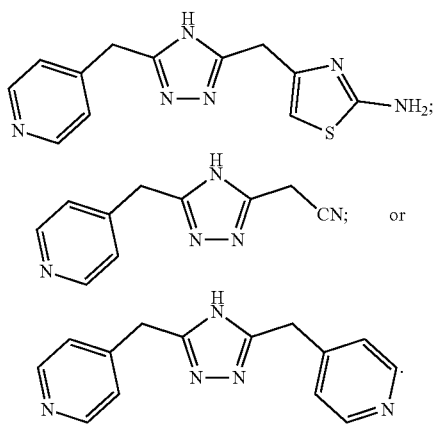

In some embodiments is a compound of Formula II, wherein X is —C($R^6$)($R^7$)—. In some embodiments is a compound of Formula II, wherein X is —C(O)—. In some embodiments is a compound of Formula II, wherein X is —C(=N—OH)—.

In another aspect described herein is a compound of Formula I, or a pharmaceutically acceptable salt thereof:

Formula I

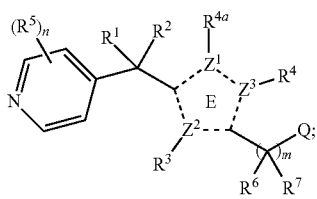

wherein:
- $Z^1$, $Z^2$, and $Z^3$ are each independently selected from O, S, N, or C, wherein Ring E is a 5-membered aromatic ring;
- Q is —CN, —$C_{1-4}$ alkyl-CN, —Cy, —$C_{1-4}$ alkyl-Cy, —$CF_3$, or $C_{1-4}$ alkyl-$CF_3$;
- $R^1$ is H;
- $R^2$ is H or $C_{1-4}$ alkyl;
- $R^3$, $R^4$, and $R^{4a}$ are each independently selected from H, halo, and $C_{1-4}$ alkyl;
- each $R^5$ is independently selected from H, halo, and $C_{1-4}$ alkyl, wherein $R^5$ is attached to a carbon atom;
- wherein $R^3$ is absent when $Z^2$ is —O—, —S—, or —N═;
- wherein $R^4$ is absent when $Z^3$ is —O—, —S—, or —N═;
- wherein $R^{4a}$ is absent when $Z^1$ is —O—, —S—, or —N═;
- $R^6$ and $R^7$ are each independently selected from H, OH, and $C_{1-4}$ alkyl;
- Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(\!=\!NR^e)R^b$, $C(\!=\!NR^e)NR^cR^d$, $NR^cC(\!=\!NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
- or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(\!=\!NR^e)R^b$, $C(\!=\!NR^e)NR^cR^d$, $NR^cC(\!=\!NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
- each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ haloalkyl, and $C_{1-4}$ haloalkoxy;
- each $R^e$ is independently selected from H, $C_{1-4}$ alkyl, and CN;
- n is 0, 1, or 2; and
- m is 1 or 2, wherein the compound is other than:

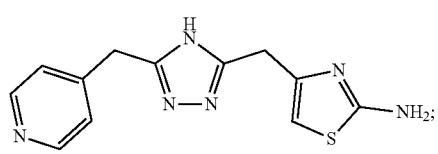

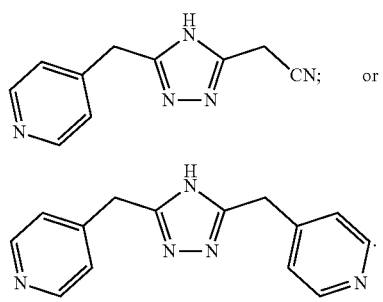

In some embodiments, the compound of Formula I or II is a compound having the structure of Formula IIa, IIb, IIc, IId, or IIe:

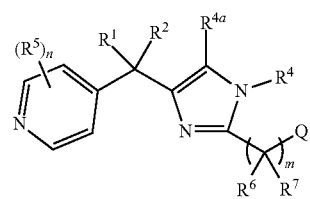

IIa

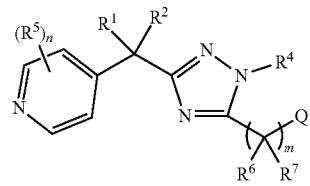

IIb

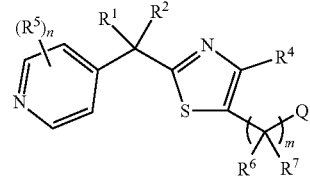

IIc

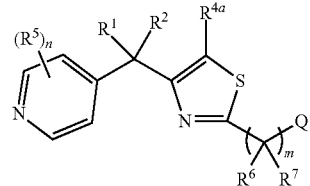

IId

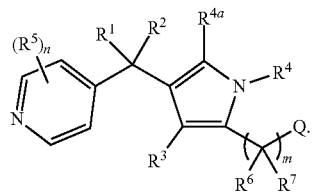

IIe

In some embodiments, the compound of Formula I or II is a compound having the structure of Formula IIa:

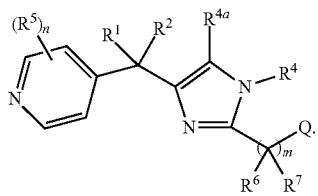

IIa

In some embodiments is a compound of Formula I, II, IIa, IIb, IIc, IId, or IIe, wherein $R^2$ is H or methyl. In some embodiments is a compound of Formula I, II, IIa, IIb, IIc, IId, or IIe, wherein $R^2$ is H. In some embodiments is a compound of Formula I, II, IIa, IIb, IIc, IId, or IIe, wherein $R^3$ is H. In some embodiments is a compound of Formula I, II, IIa, IIb, IIc, IId, or IIe, wherein $R^4$ is H. In some embodiments is a compound of Formula I, II, IIa, IIb, IIc, IId, or IIe, wherein $R^{4a}$ is H. In some embodiments is a compound of Formula I, II, IIa, IIb, IIc, IId, or IIe, wherein $R^5$ is H. In some embodiments is a compound of Formula I, II, IIa, IIb, IIc, IId, or IIe, wherein $R^6$ and $R^7$ are each independently selected from H and OH. In some embodiments is a compound of Formula I, II, IIa, IIb, IIc, IId, or IIe, wherein at least one of $R^6$ and $R^7$ is H. In some embodiments is a compound of Formula I, II, IIa, IIb, IIc, IId, or IIe, wherein both $R^6$ and $R^7$ are H. In some embodiments is a compound of Formula I, II, IIa, IIb, IIc, IId, or IIe, wherein $R^6$ is OH and $R^7$ is H. In some embodiments is a compound of Formula II, IIa, IIb, IIc, IId, or IIe, wherein $R^6$ is —$OR^a$ and $R^7$ is H. In some embodiments is a compound of Formula II, IIa, IIb, IIc, IId, or IIe, wherein $R^6$ is —$OR^a$, $R^a$ is $C_{1-4}$ alkyl, and $R^7$ is H. In some embodiments is a compound of Formula II, IIa, IIb, IIc, IId, or IIe, wherein $R^6$ is —$OCH_3$ and $R^7$ is H. In some embodiments is a compound of Formula I, II, IIa, IIb, IIc, IId, or IIe, wherein $R^6$ is $NR^cR^d$ and $R^7$ is H. In some embodiments is a compound of Formula I, II, IIa, IIb, IIc, IId, or IIe, wherein $R^7$ is H. In some embodiments is a compound of Formula I, II, IIa, IIb, IIc, IId, or IIe, wherein Q is —CN or —$C_{1-4}$ alkyl-CN. In some embodiments is a compound of Formula I, II, IIa, IIb, IIc, IId, or IIe, wherein Q is —CN. In some embodiments is a compound of Formula I, II, IIa, IIb, IIc, IId, or IIe, wherein Q is —$CF_3$, or $C_{1-4}$ alkyl-$CF_3$. In some embodiments is a compound of Formula I, II, IIa, IIb, IIc, IId, or IIe, wherein Q is —$CF_3$. In some embodiments is a compound of Formula I, II, IIa, IIb, IIc, IId, or IIe, wherein Q is —Cy or —$C_{1-4}$ alkyl-Cy. In some embodiments is a compound of Formula I, II, IIa, IIb, IIc, IId, or IIe, wherein Q is —Cy. In some embodiments is a compound of Formula I, II, IIa, IIb, IIc, IId, or IIe, wherein Cy is selected from $C_{6-10}$ aryl and 5-6 membered heteroaryl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula I, II, IIa, IIb, IIc, IId, or IIe, wherein Cy is selected from 5-6 membered heteroaryl optionally substituted by 1, 2, 3, or 4 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula I, II, IIa, IIb, IIc, IId, or IIe, wherein Cy is selected from 5-membered heteroaryl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula I, II, IIa, IIb, IIc, IId, or IIe, wherein Cy is selected from thiazoyl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula I, II, IIa, IIb, IIc, IId, or IIe, wherein Cy is thiazoyl. In some embodiments is a compound of Formula I, II, IIa, IIb, IIc, IId, or IIe, wherein each $R^{Cy}$ substituent is independently selected from halo, $C_{1-4}$ alkyl, $C_{1-4}$ haloalkyl, CN, $OR^a$, $C(O)R^b$, $C(O)NR^cR^d$, $C(O)OR^a$, $NR^cR^d$, $NR^cC(O)R^b$, $NR^cS(O)_2R^b$, $S(O)_2R^b$, and $S(O)_2NR^cR^d$. In some embodiments is a compound of Formula I, II, IIa, IIb, IIc, IId, or IIe, wherein n is 0. In some embodiments is a compound of Formula I, II, IIa, IIb, IIc, IId, or IIe, wherein m is 1. In some embodiments is a compound of Formula I, II, IIa, IIb, IIc, IId, or IIe, wherein m is 2.

The present invention is further directed to a pharmaceutical composition comprising a compound of the invention, or a pharmaceutically acceptable salt thereof, and at least one pharmaceutically acceptable carrier.

In another aspect is a pharmaceutical composition comprising at least one pharmaceutically acceptable carrier and a compound described herein, or a pharmaceutically acceptable salt thereof.

The present invention is further directed to a method of inhibiting SARM1 comprising contacting the SARM1 with a compound of the invention, or a pharmaceutically acceptable salt thereof.

In another aspect is a method of inhibiting SARM1 comprising contacting the SARM1 with a compound described herein, or a pharmaceutically acceptable salt thereof. In some embodiments is a method of inhibiting SARM1 comprising contacting the SARM1 with a compound described herein, or a pharmaceutically acceptable salt thereof, wherein the contacting is carried out in vitro. In some embodiments is a method of inhibiting SARM1 comprising contacting the SARM1 with a compound described herein, or a pharmaceutically acceptable salt thereof, wherein the contacting is carried out in vivo.

The present invention is further directed to a method of inhibiting axonal degeneration in a patient in need thereof comprising administering to the patient an inhibiting amount of a compound of the invention, or a pharmaceutically acceptable salt thereof.

In another aspect is a method of inhibiting axonal degeneration in a patient in need thereof comprising administering to the patient an inhibiting amount of a compound described herein, or a pharmaceutically acceptable salt thereof. In some embodiments is a method of inhibiting axonal degeneration in a patient in need thereof comprising administering to the patient an inhibiting amount of a compound described herein, or a pharmaceutically acceptable salt thereof, wherein the axonal degeneration is caused by abnormal reduction or depletion of NAD+ in the axons.

The present invention is further directed to a method of treating or preventing a neurological disorder in a patient in need thereof comprising administering to the patient a therapeutically effective amount of a compound of the invention, or a pharmaceutically acceptable salt thereof.

In another aspect is a method of treating or preventing a neurological disorder in a patient in need thereof comprising administering to the patient a therapeutically effective amount of a compound described herein, or a pharmaceutically acceptable salt thereof. In some embodiments is a method of treating or preventing a neurological disorder in a patient in need thereof comprising administering to the patient a therapeutically effective amount of a compound described herein, or a pharmaceutically acceptable salt thereof, wherein the neurological disorder is a neurodegenerative disease.

The present invention is further directed to a method of treating or preventing a neurological disorder in a patient in need thereof comprising administering to the patient a therapeutically effective amount of a compound of the invention, or a pharmaceutically acceptable salt thereof, in combination with a further pharmaceutically active agent.

In some embodiments is a method of treating or preventing a neurological disorder in a patient in need thereof comprising administering to the patient a therapeutically effective amount of a compound described herein, or a pharmaceutically acceptable salt thereof, in combination with a further pharmaceutically active agent.

The present invention is further directed to use of a compound of the invention, or a pharmaceutically acceptable salt thereof, in treating or preventing a neurological disorder in a patient in need thereof.

The present invention is further directed to a compound of the invention, or a pharmaceutically acceptable salt thereof, for use in the preparation of a medicament for treating or preventing a neurological disorder in a patient in need thereof.

DETAILED DESCRIPTION

Similar to programmed cell death pathways (e.g., apoptosis), axonal degeneration in response to injury or disease stimulates a local signaling cascade that causes destruction of the injured axon segment (Summers D. W., et al., PNAS USA, 2016 Oct. 11, 113(41):E6271-E6280). Following injury, the axonal skeleton disintegrates, and the axonal membrane breaks apart. Subsequent to axonal degeneration, the myelin sheath degrades and infiltration by macrophages follows; the macrophages, along with Schwann cells, clear the cellular debris resulting from the degeneration (Coleman M. P., et al., PNAS USA, 1998 August, 95(17):9985-90).

SARM1 (sterile alpha and TIR motif-containing 1) protein (NP_055892) is a 724 amino acid protein involved in axon degeneration. It has also been implicated in infectious and inflammatory disorders. The SARM1 protein, also known as FLJ36296, KIAA0524, MyD88-5, SAM domain-containing protein 2, and SAMD2, comprises four domains, i) a mitochondrial localization signal, ii) an auto-inhibitory N-terminus region consisting of armadillo/HEAT motifs, iii) two sterile alpha motifs responsible for multimerization, and iv) a C-terminus Toll/Interleukin-1 receptor that possesses enzymatic activity (Essuman K., et al., Neuron 2017 March, 93(6):1334-43.e5).

SARM1 protein plays a critical role in the Wallerian degeneration pathway. Activation of SARM1 triggers a rapid collapse of NAD$^+$ levels in the distal section of the injured axon, which then undergoes degeneration (Gerdts J. et al., Science 2015 April 348(6233):453-57). Promoting dimerization of the Toll/interleukin receptor (TIR) domain of SARM1 has been shown to be sufficient to promote NAD$^+$ loss and axon degeneration.

SARM1's activity is responsible for, at least in part, the protective nature of the survival factor NMNAT2, as NMKNAT enzymes have been found to prevent SARM1-mediated depletion of NAD$^+$. Other pro-degeneration signaling pathways, including the MAP kinase pathway, have been linked to SARM1 activation. MAPK signaling has been shown to promote the loss of NMNAT2, which promotes SARM1 activation (See, e.g., Yang J. et al., Cell 2015 January 160(1-2):161-76).

SARM1 is involved in the innate immune response. It promotes neuronal cell death in response to stress and other stimuli. SARM1 acts as a negative regulator of TICAM1/TRIF-dependent Toll-like receptor signaling by inhibiting induction of TLR3- and TLR4-dependent genes, which play a pivotal role in activating axonal degeneration following injury. In addition, SARM1 specifically blocks TICAM1/TRIF-dependent transcription factor activation and gene induction, without affecting the MYD88-dependent pathway or non-TLR signaling. It is also a negative regulator of NF-kappa-B and TRF activation. (See, e.g., Summers, D. W. et al., J Neurosci., 2014 Jul. 9, 34(28):9338-50).

In some embodiments, the present invention provides inhibitors of SARM1. SARM1 activation can cause a rapid reduction in NAD+ levels in injured axons, which then undergo degeneration. In particular embodiments, the compounds inhibit axonal degeneration, including axonal degeneration that results from reduction or depletion of NAD$^+$ (e.g., inhibition of SARM1 NADase).

Further described herein are active-site SARM1 NAD hydrolase inhibitors. In some aspects, the inhibitors described herein actin the catalytic pocket but do not directly compete with substrate binding. In some aspects, the inhibitors are uncompetitive, pro-inhibitors that function by opportunistically intercepting the NAD hydrolysis reaction and undergoing covalent conjugation with the reaction product adenosine diphosphate ribose (ADPR). In some embodiments, the resulting small molecule-ADPR adducts confer knock-out like axon protection in vivo—reducing levels of the translatable biomarker neurofilament light and conferring functional protection. In some embodiments, described herein is a mode of pharmacologic inhibition that has implications not just for SARM1 but for a broader panel of related NAD hydrolases linked to age-related decline and disease.

Compounds

Compounds described herein, including pharmaceutically acceptable salts, active metabolites and pharmaceutically acceptable solvates thereof, are inhibitors of SARM1.

The present invention is directed to inhibitors of SARM1 such as a compound of Formula I:

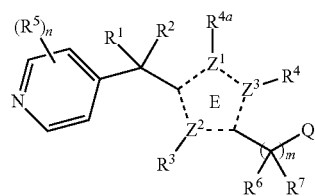

I or a pharmaceutically acceptable salt thereof, wherein:

$Z^1$, $Z^2$, and $Z^3$ are each independently selected from O, S, N, or C, wherein Ring E is a 5-membered aromatic ring;

Q is —CN, —$C_{1-4}$ alkyl-CN, —Cy, —$C_{1-4}$ alkyl-Cy, —$CF_3$, or $C_{1-4}$ alkyl-$CF_3$;

$R^1$ is H;

$R^2$ is H or $C_{1-4}$ alkyl;

$R^3$, $R^4$, and $R^{4a}$ are each independently selected from H, halo, and $C_{1-4}$ alkyl;

each $R^5$ is independently selected from H, halo, and $C_{1-4}$ alkyl, wherein $R^5$ is attached to a carbon atom;

wherein $R^3$ is absent when $Z^2$ is —O—, —S—, or —N=;

wherein $R^4$ is absent when $Z^3$ is —O—, —S—, or —N=;

wherein $R^{4a}$ is absent when $Z^1$ is —O—, —S—, or —N=;

$R^6$ and $R^7$ are each independently selected from H, OH, and $C_{1-4}$ alkyl;

Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;

each $R^e$ is independently selected from H, $C_{1-4}$ alkyl, and CN;

n is 0, 1, or 2; and m is 1 or 2.

In some embodiments, the compound is other than:

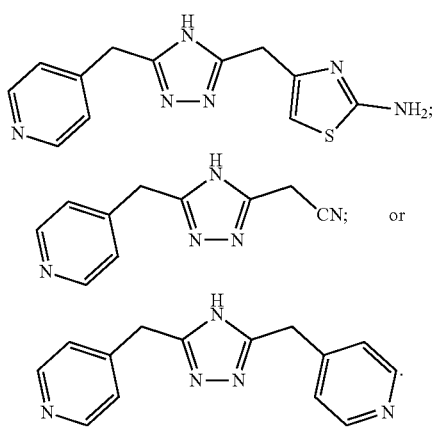

In some embodiments, the compound of the invention has Formula IIa, IIb, IIc, IId, or IIe:

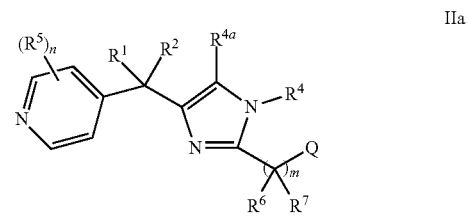

IIa

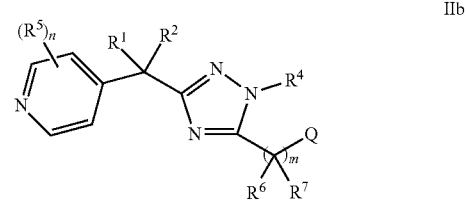

IIb

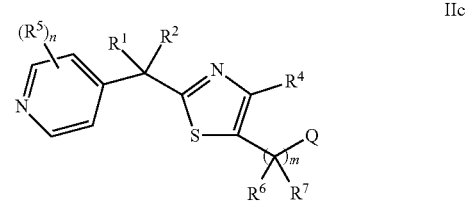

IIc

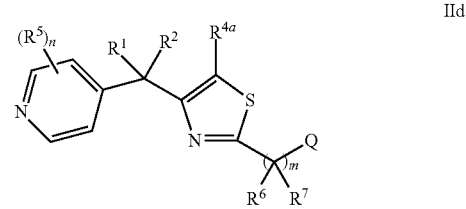

IId

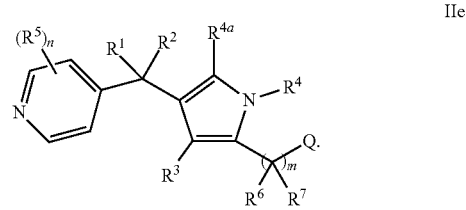

IIe

In some embodiments, Ring E is a 5-membered aromatic ring selected from pyrrole, pyrazole, imidazole, triazole, thiazole, isoxazole, oxazole, isoxazole, furan, and thiophene. In some embodiments, Ring E is a 5-membered aromatic ring selected from pyrrole, imidazole, triazole, and thiazole.

In some embodiments, $R^2$ is H or methyl. In some embodiments, $R^2$ is H.

In some embodiments, $R^3$ is H.

In some embodiments, $R^4$ is H.

In some embodiments, $R^{4a}$ is H.

In some embodiments, each $R^5$ is H.

In some embodiments, $R^6$ and $R^7$ are each independently selected from H and OH. In some embodiments, at least one of $R^6$ and $R^7$ is H. In some embodiments, both $R^6$ and $R^7$ are H.

In some embodiments, Q is —CN, —$C_{1-4}$ alkyl-CN, —$CF_3$, or $C_{1-4}$ alkyl-$CF_3$. In some embodiments, Q is —CN or —$C_{1-4}$ alkyl-CN. In some embodiments, Q is —CN. In some embodiments, Q is —$CF_3$, or $C_{1-4}$ alkyl-$CF_3$. In some embodiments, Q is —$CF_3$. In some embodiments, Q is —Cy or —$C_{1-4}$ alkyl-Cy. In some embodiments, Q is —Cy.

In some embodiments, Cy is selected from $C_{6-10}$ aryl and 5-6 membered heteroaryl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is selected from 5-6 membered heteroaryl optionally substituted by 1, 2, 3, or 4 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is selected from 5-membered heteroaryl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NRS(O)_2NR^cR^d$, $S(O)R^b$, $S(O)NR^cR^d$, $S(O)_2R^b$, and $S(O)_2NR^cR^d$.

In some embodiments, Cy is selected from thiazoyl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is thiazoyl.

In some embodiments, each $R^{cy}$ substituent is independently selected from halo, $C_{1-4}$ alkyl, $C_{1-4}$ haloalkyl, CN, $OR^a$, $C(O)R^b$, $C(O)NR^cR^d$, $C(O)OR^a$, $NR^cR^d$, $NR^cC(O)R^b$, $NR^cS(O)_2R^b$, $S(O)_2R^b$, and $S(O)_2NR^cR^d$.

In some embodiments, n is 0. In some embodiments, n is 1. In some embodiments, n is 2.

In some embodiments, m is 1. In some embodiments, m is 2.

In some embodiments, the compound is a compound of Formula IIIa, IIIb, IIIc, IIId, or IIIe:

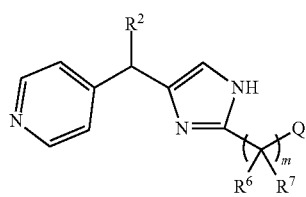
IIIa

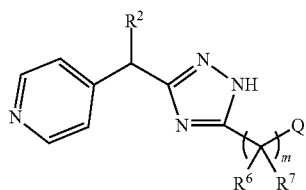
IIIb

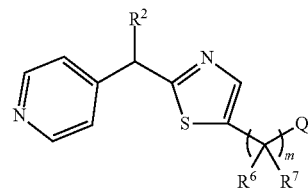
IIIc

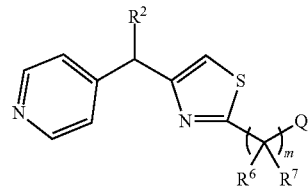
IIId

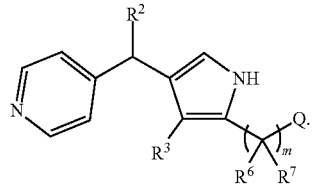
IIIe

In some embodiments described herein is a SARM1 inhibitor which is a compound of Formula II, or a pharmaceutically acceptable salt thereof:

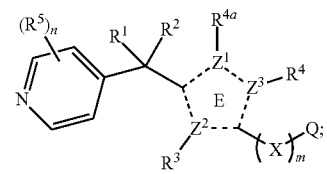
Formula II wherein:
$Z^1$, $Z^2$, and $Z^3$ are each independently selected from O, S, N, or C, wherein Ring E is a 5-membered aromatic ring;

Q is —CN, —$C_{1-4}$ alkyl-CN, —Cy, —$C_{1-4}$ alkyl-Cy, —$CF_3$, or $C_{1-4}$ alkyl-$CF_3$;

X is —C($R^6$)($R^7$)—, —C(O)—, or —C(=N—OH)—;

$R^1$ is H;

$R^2$ is H or $C_{1-4}$ alkyl;

$R^3$, $R^4$, and $R^{4a}$ are each independently selected from H, halo, and $C_{1-4}$ alkyl;

each $R^5$ is independently selected from H, halo, and $C_{1-4}$ alkyl, wherein $R^5$ is attached to a carbon atom;

wherein $R^3$ is absent when $Z^2$ is —O—, —S—, or —N=;

wherein $R^4$ is absent when $Z^3$ is —O—, —S—, or —N=;

wherein $R^{4a}$ is absent when $Z^1$ is —O—, —S—, or —N=;

$R^6$ and $R^7$ are each independently selected from H, —$OR^a$, —$NR^cR^d$, $C_{1-4}$ alkyl, and $C_{1-4}$ haloalkyl;

Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

or two adjacent R$^{Cy}$ substituents together with the atoms to which they are attached form a fused phenyl, C$_{3-7}$ cycloalkyl, 5-6 membered heteroaryl, or 4-7 membered heterocycloalkyl ring, each optionally substituted by 1, 2, 3, 4, or 5 substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^a$, R$^b$, R$^c$, and R$^d$ is independently selected from H, C$_{1-4}$ alkyl, and C$_{1-4}$ haloalkyl, wherein said C$_{1-4}$ alkyl is optionally substituted with 1, 2, or 3 substituents independently selected from OH, CN, amino, halo, C$_{1-4}$ alkyl, C$_{1-4}$ alkoxy, C$_{1-4}$haloalkyl, and C$_{1-4}$haloalkoxy;

each R$^e$ is independently selected from H, C$_{1-4}$ alkyl, and CN;

n is 0, 1, or 2; and m is 1 or 2, wherein the compound is other than:

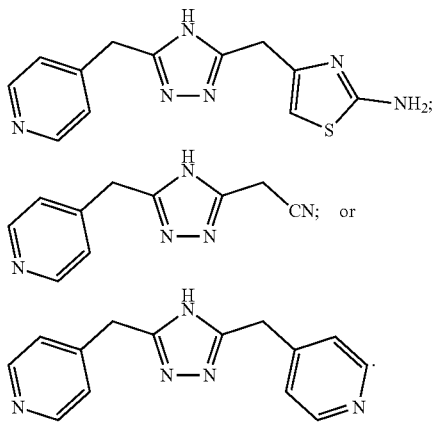

In some embodiments is a compound of Formula II, wherein X is —C(R$^6$)(R$^7$)—. In some embodiments is a compound of Formula II, wherein X is —C(O)—. In some embodiments is a compound of Formula II, wherein X is —C(R$^6$)(R$^7$)— and m is 1. In some embodiments is a compound of Formula II, wherein X is —C(R$^6$)(R$^7$)— and m is 2. In some embodiments is a compound of Formula II, wherein R$^6$ and R$^7$ are each independently selected from H and OH. In some embodiments is a compound of Formula II, wherein at least one R$^6$ and R$^7$ is H. In some embodiments is a compound of Formula II, wherein both R$^6$ and R$^7$ are H. In some embodiments is a compound of Formula II, wherein R$^6$ is OH and R$^7$ is H. In some embodiments is a compound of Formula II, wherein R$^6$ is —OR$^a$ and R$^7$ is H. In some embodiments is a compound of Formula II, wherein R$^6$ is —OR$^a$, R$^a$ is C$_{1-4}$ alkyl, and R$^7$ is H. In some embodiments is a compound of Formula II, wherein R$^6$ is —OCH$_3$ and R$^7$ is H. In some embodiments is a compound of Formula II, wherein R$^6$ is NR$^c$R$^d$ and R$^7$ is H. In some embodiments is a compound of Formula II, wherein R$^6$ is NH$_2$ and R$^7$ is H.

In some embodiments is a compound of Formula II, wherein X is —C(O)—. In some embodiments is a compound of Formula II, wherein X is —C(O)— and m is 1.

In some embodiments is a compound of Formula II, wherein X is —C(=N—OH)—. In some embodiments is a compound of Formula II, wherein X is —C(=N—OH)— and m is 1.

In some embodiments is a compound of Formula II, wherein Q is —CN or —C$_{1-4}$ alkyl-CN.

In some embodiments is a compound of Formula II, wherein Q is —CN. In some embodiments is a compound of Formula II, wherein Q is —C$_{1-4}$ alkyl-CN.

In some embodiments is a compound of Formula II, wherein Q is —CF$_3$ or C$_{1-4}$ alkyl-CF$_3$.

In some embodiments is a compound of Formula II, wherein Q is —CF$_3$. In some embodiments is a compound of Formula II, wherein Q is C$_{1-4}$ alkyl-CF$_3$.

In some embodiments is a compound of Formula II, wherein Q is —Cy or —C$_{1-4}$ alkyl-Cy.

In some embodiments is a compound of Formula II, wherein Q is —Cy. In some embodiments is a compound of Formula II, wherein Q is —C$_{1-4}$ alkyl-Cy.

In some embodiments is a compound of Formula II, wherein Q is —Cy and Cy is selected from C$_{6-10}$ aryl and 5-6 membered heteroaryl, each optionally substituted by 1, 2, 3, 4, or 5 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$. In some embodiments is a compound of Formula II, wherein Q is —Cy and Cy is selected from 5-6 membered heteroaryl optionally substituted by 1, 2, 3, or 4 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$. In some embodiments is a compound of Formula II, wherein Q is —Cy and Cy is selected from 5-membered heteroaryl optionally substituted by 1 or 2 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$. In some embodiments is a compound of Formula II, wherein Q is —Cy and Cy is thiazoyl optionally substituted by 1 or 2 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$. In some embodiments is a compound of Formula II, wherein Q is —Cy and Cy is thiazoyl optionally substituted by 1 or 2 R$^{Cy}$ substituents and each R$^{Cy}$ substituent is independently selected from halo, C$_{1-4}$ alkyl, C$_{1-4}$ haloalkyl, CN, OR$^a$, C(O)R$^b$, C(O)NR$^c$R$^d$, C(O)OR$^a$, NR$^c$R$^d$, NR$^c$C(O)R$^b$, NR$^c$S(O)$_2$R$^b$, S(O)$_2$R$^b$, and S(O)$_2$NR$^c$R$^d$.

In some embodiments is a compound of Formula II, wherein Q is —Cy and Cy is unsubstituted thiazoyl.

In some embodiments is a compound of Formula II, wherein n is 0. In some embodiments is a compound of Formula II, wherein n is 1. In some embodiments is a compound of Formula II, wherein n is 2.

In some embodiments is a compound of Formula II, wherein $R^2$ is H or methyl. In some embodiments is a compound of Formula II, wherein $R^2$ is H. In some embodiments is a compound of Formula II, wherein $R^2$ is methyl.

In some embodiments described herein is a compound of Formula IIa, or a pharmaceutically acceptable salt thereof:

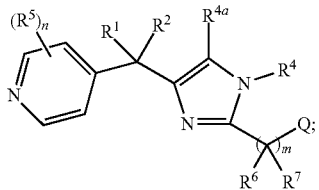

Formula IIa wherein:
- Q is —Cy, —$C_{1-4}$ alkyl-Cy, —$CF_3$, or $C_{1-4}$ alkyl-$CF_3$;
- $R^1$ is H;
- $R^2$ is H or $C_{1-4}$ alkyl;
- $R^4$ and $R^{4a}$ are each independently selected from H, halo, and $C_{1-4}$ alkyl;
- each $R^5$ is independently selected from H, halo, and $C_{1-4}$ alkyl, wherein $R^5$ is attached to a carbon atom;
- $R^6$ and $R^7$ are each independently selected from H, —$OR^a$, —$NR^cR^d$, $C_{1-4}$ alkyl, and $C_{1-4}$ haloalkyl;
- Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
- or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
- each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;
- each $R^e$ is independently selected from H, $C_{1-4}$ alkyl, and CN;
- n is 0, 1, or 2; and
- m is 1 or 2.

In some embodiments is a compound of Formula IIa, wherein $R^4$ is selected from H and $C_{1-4}$ alkyl. In some embodiments is a compound of Formula IIa, wherein $R^4$ is H. In some embodiments is a compound of Formula IIa, wherein $R^4$ is $C_{1-4}$ alkyl.

In some embodiments is a compound of Formula IIa, wherein $R^{4a}$ is selected from H and $C_{1-4}$ alkyl. In some embodiments is a compound of Formula IIa, wherein $R^{4a}$ is H. In some embodiments is a compound of Formula IIa, wherein $R^{4a}$ is $C_{1-4}$ alkyl.

In some embodiments is a compound of Formula IIa, wherein m is 1. In some embodiments is a compound of Formula IIa, wherein m is 2. In some embodiments is a compound of Formula IIa, wherein $R^6$ and $R^7$ are each independently selected from H and OH.

In some embodiments is a compound of Formula IIa, wherein at least one $R^6$ and $R^7$ is H. In some embodiments is a compound of Formula IIa, wherein both $R^6$ and $R^7$ are H. In some embodiments is a compound of Formula IIa, wherein $R^6$ is OH and $R^7$ is H. In some embodiments is a compound of Formula IIa, wherein $R^6$ is —$OR^a$ and $R^7$ is H. In some embodiments is a compound of Formula IIa, wherein $R^6$ is —$OR^a$, $R^a$ is $C_{1-4}$ alkyl, and $R^7$ is H. In some embodiments is a compound of Formula IIa, wherein $R^6$ is —$OCH_3$ and $R^7$ is H. In some embodiments is a compound of Formula IIa, wherein $R^6$ is $NR^cR^d$ and $R^7$ is H. In some embodiments is a compound of Formula IIa, wherein $R^6$ is $NH_2$ and $R^7$ is H.

In some embodiments is a compound of Formula IIa, wherein Q is —$CF_3$ or $C_{1-4}$ alkyl-$CF_3$. In some embodiments is a compound of Formula IIa, wherein Q is —$CF_3$. In some embodiments is a compound of Formula IIa, wherein Q is $C_{1-4}$ alkyl-$CF_3$.

In some embodiments is a compound of Formula IIa, wherein Q is —Cy or —$C_{1-4}$ alkyl-Cy. In some embodiments is a compound of Formula IIa, wherein Q is —Cy. In some embodiments is a compound of Formula IIa, wherein Q is —$C_{1-4}$ alkyl-Cy.

In some embodiments is a compound of Formula IIa, wherein Q is —Cy and Cy is selected from $C_{6-10}$ aryl and 5-6 membered heteroaryl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^c(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula IIa, wherein Q is —Cy and Cy is selected from 5-6 membered heteroaryl optionally substituted by 1, 2, 3, or 4 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula IIa, wherein Q is —Cy and Cy is selected from 5-membered heteroaryl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments is a compound of Formula IIa, wherein Q is —Cy and Cy is thiazoyl optionally substituted by 1 or 2 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NRS(O)_2R^b$, $NR^cS(O)_2NR^cR^d$, $S(O)R^b$, $S(O)NR^cR^d$, $S(O)_2R^b$, and $S(O)_2NR^cR^d$. In some embodiments a compound of Formula IIa, wherein Q is —Cy and Cy is thiazoyl optionally substituted by 1 or 2 $R^{Cy}$ substituents and each $R^{Cy}$ substituent is independently selected from halo, $C_{1-4}$ alkyl, $C_{1-4}$ haloalkyl, CN, $OR^a$, $C(O)R^b$, $C(O)NR^cR^d$, $C(O)OR^a$, $NR^cR^d$, $NR^cC(O)R^b$, $NR^cS(O)_2R^b$, $S(O)_2R^b$, and $S(O)_2NR^cR^d$.

In some embodiments is a compound of Formula IIa, wherein Q is —Cy and Cy is unsubstituted thiazoyl.

In some embodiments is a compound of Formula IIa, wherein n is 0. In some embodiments is a compound of Formula IIa, wherein n is 1. In some embodiments is a compound of Formula IIa, wherein n is 2.

In some embodiments is a compound of Formula IIa, wherein $R^2$ is H or methyl. In some embodiments is a compound of Formula IIa, wherein $R^2$ is H. In some embodiments is a compound of Formula IIa, wherein $R^2$ is methyl.

In some embodiments is a compound selected from:
4-((2-(2,2,2-Trifluoroethyl)-1H-imidazol-4-yl)methyl)pyridine;
4-((2-(3,3,3-trifluoropropyl)-1H-imidazol-4-yl)methyl)pyridine;
2-(4-(Pyridin-4-ylmethyl)-1H-imidazol-2-yl)acetonitrile;
3-(4-(Pyridin-4-ylmethyl)-1H-imidazol-2-yl)propanenitrile;
rac-4-(1-(2-(2,2,2-Trifluoroethyl)-1H-imidazol-4-yl)ethyl)pyridine;
(R)-4-(1-(2-(2,2,2-Trifluoroethyl)-1H-imidazol-4-yl)ethyl)pyridine;
(S)-4-(1-(2-(2,2,2-Trifluoroethyl)-1H-imidazol-4-yl)ethyl)pyridine;
5-((4-(Pyridin-4-ylmethyl)-1H-imidazol-2-yl)methyl)thiazole;
4-((5-(2,2,2-Trifluoroethyl)-1H-1,2,4-triazol-3-yl)methyl)pyridine;
2-(Pyridin-4-ylmethyl)-4-(2,2,2-trifluoroethyl)thiazole;
4-(Pyridin-4-ylmethyl)-2-(2,2,2-trifluoroethyl)thiazole;
rac-4-(1-(5-(2,2,2-trifluoroethyl)-1H-pyrrol-2-yl)ethyl)pyridine;
(S)-2,2,2-Trifluoro-1-(5-(pyridin-4-ylmethyl)-1H-imidazol-2-yl)ethan-1-ol;
(R)-2,2,2-Trifluoro-1-(5-(pyridin-4-ylmethyl)-1H-imidazol-2-yl)ethan-1-ol;
2,2,2-Trifluoro-1-(5-(pyridin-4-ylmethyl)-1H-imidazol-2-yl)ethan-1-one;
(E/Z)-2,2,2-Trifluoro-1-(5-(pyridin-4-ylmethyl)-1H-imidazol-2-yl)ethan-1-one oxime;
4-((5-Methyl-2-(2,2,2-trifluoroethyl)-1H-imidazol-4-yl)methyl)pyridine;
(S)-2,2,2-trifluoro-1-(4-(pyridin-4-ylmethyl)-1H-imidazol-2-yl)ethan-1-amine;
(R)-2,2,2-trifluoro-1-(4-(pyridin-4-ylmethyl)-1H-imidazol-2-yl)ethan-1-amine;
(S)-2,2,2-Trifluoro-N-methyl-1-(5-(pyridin-4-ylmethyl)-1H-imidazol-2-yl)ethan-1-amine;
(R)-2,2,2-Trifluoro-N-methyl-1-(5-(pyridin-4-ylmethyl)-1H-imidazol-2-yl)ethan-1-amine;
(S)-2,2,2-Trifluoro-N,N-dimethyl-1-(5-(pyridin-4-ylmethyl)-1H-imidazol-2-yl)ethan-1-amine;
(R)-2,2,2-Trifluoro-N,N-dimethyl-1-(5-(pyridin-4-ylmethyl)-1H-imidazol-2-yl)ethan-1-amine;
(E/Z)-2,2,2-Trifluoro-1-(4-(pyridin-4-ylmethyl)thiazol-2-yl)ethan-1-one oxime;
(R)-2,2,2-Trifluoro-1-(5-(pyridin-4-ylmethyl)thiazol-2-yl)ethan-1-amine;
(S)-2,2,2-Trifluoro-1-(5-(pyridin-4-ylmethyl) thiazol-2-yl)ethan-1-amine;
(S)-(4-(Pyridin-4-ylmethyl)-1H-imidazol-2-yl)(thiazol-5-yl)methanol;
(R)-(4-(Pyridin-4-ylmethyl)-1H-imidazol-2-yl)(thiazol-5-yl)methanol;
(5-((3-Methylpyridin-4-yl)methyl)-1H-imidazol-2-yl)(thiazol-5-yl)methanol;
3,5-Dichloro-4-((2-(2,2,2-trifluoroethyl)-1H-imidazol-5-yl)methyl)pyridine;
1-(4-((3-Chloropyridin-4-yl)methyl)-1H-imidazol-2-yl)-2,2,2-trifluoroethan-1-ol;
(S)-2,2,2-trifluoro-1-(4-((S)-1-(pyridin-4-yl)ethyl)-1H-imidazol-2-yl)ethan-1-ol;
(R)-2,2,2-trifluoro-1-(4-((S)-1-(pyridin-4-yl)ethyl)-1H-imidazol-2-yl)ethan-1-ol;
(S)-2,2,2-trifluoro-1-(4-((R)-1-(pyridin-4-yl)ethyl)-1H-imidazol-2-yl)ethan-1-ol;
(R)-2,2,2-trifluoro-1-(4-((R)-1-(pyridin-4-yl)ethyl)-1H-imidazol-2-yl)ethan-1-ol;
3-Methyl-4-((2-(2,2,2-trifluoroethyl)-1H-imidazol-4-yl)methyl)pyridine;
(R)-2,2,2-Trifluoro-1-(4-(pyridin-4-ylmethyl)-1H-imidazol-2-yl)-1-(thiazol-5-yl)ethan-1-ol; and
(S)-2,2,2-Trifluoro-1-(4-(pyridin-4-ylmethyl)-1H-imidazol-2-yl)-1-(thiazol-5-yl)ethan-1-ol;
or a pharmaceutically acceptable salt of any of the aforementioned.

In some embodiments is a compound selected from:
3-Chloro-4-((2-(2,2,2-trifluoroethyl)-1H-imidazol-4-yl)methyl)pyridine;
2-Chloro-4-((2-(2,2,2-trifluoroethyl)-1H-imidazol-4-yl)methyl)pyridine;
2-Fluoro-4-((2-(2,2,2-trifluoroethyl)-3H-imidazol-4-yl)methyl)pyridine;
(S)-(5-((3-Methylpyridin-4-yl)methyl)-1H-imidazol-2-yl)(thiazol-5-yl)methanol;
(R)-(5-((3-Methylpyridin-4-yl)methyl)-1H-imidazol-2-yl)(thiazol-5-yl)methanol;
(R)-(5-(Pyridin-4-ylmethyl)-1H-imidazol-2-yl)(thiazol-2-yl)methanol;
(S)-(5-(Pyridin-4-ylmethyl)-1H-imidazol-2-yl)(thiazol-2-yl)methanol;
(R)-1,1,1-Trifluoro-2-(5-(pyridin-4-ylmethyl)-1H-imidazol-2-yl)propan-2-ol;
(S)-1,1,1-Trifluoro-2-(5-(pyridin-4-ylmethyl)-1H-imidazol-2-yl)propan-2-ol;
(S)-4-((2-(2,2,2-trifluoro-1-methoxyethyl)-1H-imidazol-5-yl)methyl)pyridine;
(R)-4-((2-(2,2,2-trifluoro-1-methoxyethyl)-1H-imidazol-5-yl)methyl)pyridine;
(R)-2,2,2-Trifluoro-1-(5-((2-fluoropyridin-4-yl)methyl)-1H-imidazol-2-yl)ethan-1-ol;
(S)-2,2,2-Trifluoro-1-(5-((2-fluoropyridin-4-yl)methyl)-1H-imidazol-2-yl)ethan-1-ol;
Pyridin-2-yl(5-(pyridin-4-ylmethyl)-1H-imidazol-2-yl)methanol;
3-Fluoro-4-((2-(2,2,2-trifluoroethyl)-1H-imidazol-4-yl)methyl)pyridine;
(S)-2,2,2-Trifluoro-1-(4-((3-methylpyridin-4-yl)methyl)-1H-imidazol-2-yl)ethan-1-ol;
(R)-2,2,2-Trifluoro-1-(4-((3-methylpyridin-4-yl)methyl)-1H-imidazol-2-yl)ethan-1-ol;
(S)-2,2,2-Trifluoro-1-(4-((3-fluoropyridin-4-yl)methyl)-1H-imidazol-2-yl)ethan-1-ol;
(R)-2,2,2-Trifluoro-1-(4-((3-fluoropyridin-4-yl)methyl)-1H-imidazol-2-yl)ethan-1-ol;
1,1,1,3,3,3-Hexafluoro-2-(4-(pyridin-4-ylmethyl)-1H-imidazol-2-yl)propan-2-ol; and
1,1,1-Trifluoro-2-(4-(pyridin-4-ylmethyl)-1H-imidazol-2-yl)propan-2-ol;

23 or a pharmaceutically acceptable salt of any of the aforementioned.

Further Embodiments

1. A compound of Formula II:

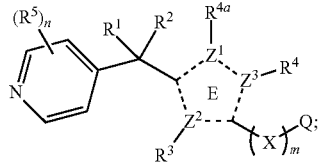

Formula II or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
X is —C($R^6$)($R^7$)—, —C(O)—, or —C(=N—OH)—;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, —$OR^a$, —$NR^cR^d$, $C_{1-4}$ alkyl, and $C_{1-4}$ haloalkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;
each $R^e$ is independently selected from H, $C_{1-4}$ alkyl, and CN;
n is 0, 1, or 2; and
m is 1 or 2,

24 wherein the compound is other than:

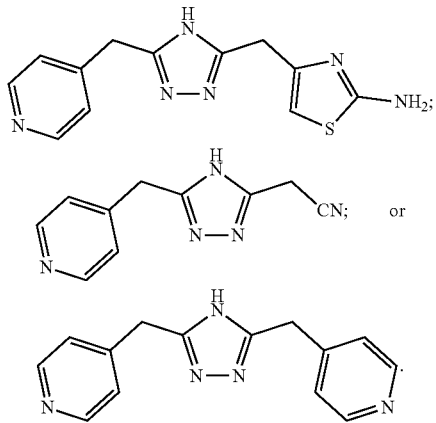

2. The compound of embodiment 1, or a pharmaceutically acceptable salt thereof, wherein X is —C($R^6$)($R^7$)—.
3. The compound of embodiment 1, or a pharmaceutically acceptable salt thereof, wherein X is —C(O)—.
4. A compound of Formula I:

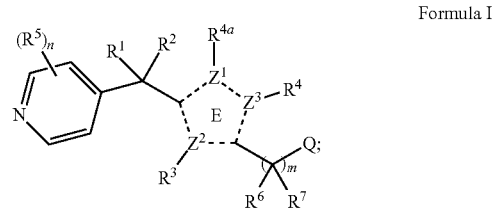

Formula I or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, OH, and $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^c R^d$, $NR^cR^d$, $NR^cC(O)R^b$, $NR^cC(O)OR^a$, $NR^cC(O)NR^c R^d$, $C(=NR^e)R^b$, $C(=NR^e)NR^cR^d$, $NR^cC(=NR^e)NR^c R^d$, $NR^cS(O)R^b$, $NR^cS(O)_2R^b$, $NR^cS(O)_2NR^cR^d$, $S(O) R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;

each $R^e$ is independently selected from H, $C_{1-4}$ alkyl, and CN;

n is 0, 1, or 2; and m is 1 or 2, wherein the compound is other than:

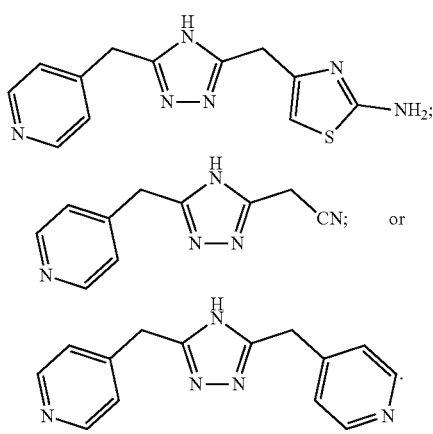

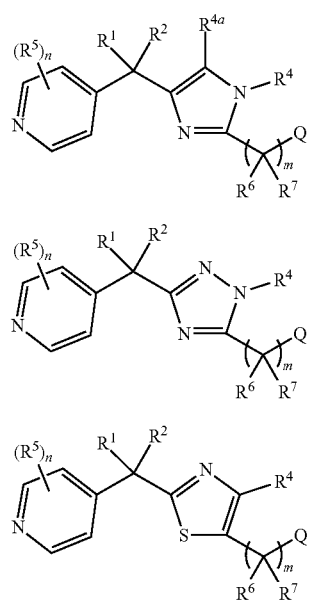

5. The compound of embodiment 1 or embodiment 4, or a pharmaceutically acceptable salt thereof, having Formula IIa, IIb, IIc, IId, or IIe:

IIa
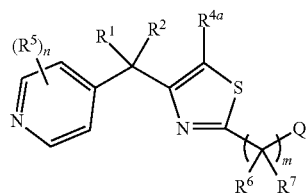

IIb
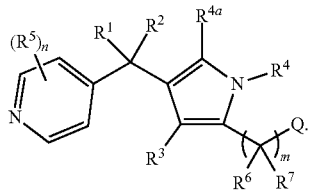

IIc
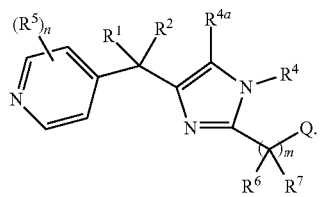

IId

IIe

6. The compound of embodiment 5, or a pharmaceutically acceptable salt thereof, having Formula IIa:

IIa

7. The compound of any one of embodiments 1-6, or a pharmaceutically acceptable salt thereof, wherein $R^2$ is H or methyl.

8. The compound of any one of embodiments 1-7, or a pharmaceutically acceptable salt thereof, wherein $R^2$ is H.

9. The compound of any one of embodiments 1-8, or a pharmaceutically acceptable salt thereof, wherein $R^3$ is H.

10. The compound of any one of embodiments 1-9, or a pharmaceutically acceptable salt thereof, wherein $R^4$ is H.

11. The compound of any one of embodiments 1-10, or a pharmaceutically acceptable salt thereof, wherein $R^{4a}$ is H.

12. The compound of any one of embodiments 1-11, or a pharmaceutically acceptable salt thereof, wherein each $R^5$ is H.

13. The compound of any one of embodiments 1-12, or a pharmaceutically acceptable salt thereof, wherein $R^6$ and $R^7$ are each independently selected from H and OH.

14. The compound of any one of embodiments 1-13, or a pharmaceutically acceptable salt thereof, wherein at least one of $R^6$ and $R^7$ is H.

15. The compound of any one of embodiments 1-13, or a pharmaceutically acceptable salt thereof, wherein both $R^6$ and $R^7$ are H.

16. The compound of any one of embodiments 1-13, or a pharmaceutically acceptable salt thereof, wherein $R^6$ is OH and $R^7$ is H.

17. The compound of any one of embodiments 1-13, or a pharmaceutically acceptable salt thereof, wherein $R^6$ is $NR^cR^d$ and $R^7$ is H.

18. The compound of embodiment 17, or a pharmaceutically acceptable salt thereof, wherein $R^6$ is $NH_2$ and $R^7$ is H.

19. The compound of any one of embodiments 1-18, or a pharmaceutically acceptable salt thereof, wherein Q is —CN or —$C_{1-4}$ alkyl-CN.

20. The compound of any one of embodiments 1-18, or a pharmaceutically acceptable salt thereof, wherein Q is —CN.

21. The compound of any one of embodiments 1-18, or a pharmaceutically acceptable salt thereof, wherein Q is —CF$_3$, or C$_{1-4}$ alkyl-CF$_3$.

22. The compound of any one of embodiments 1-18, or a pharmaceutically acceptable salt thereof, wherein Q is —CF$_3$.

23. The compound of any one of embodiments 1-18, or a pharmaceutically acceptable salt thereof, wherein Q is —Cy or —C$_{1-4}$ alkyl-Cy.

24. The compound of any one of embodiments 1-18, or a pharmaceutically acceptable salt thereof, wherein Q is —Cy.

25. The compound of any one of embodiments 1-18, 23, and 24, or a pharmaceutically acceptable salt thereof, wherein Cy is selected from C$_{6-10}$ aryl and 5-6 membered heteroaryl, each optionally substituted by 1, 2, 3, 4, or 5 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

26. The compound of any one of embodiments 1-18, 23, and 24, or a pharmaceutically acceptable salt thereof, wherein Cy is selected from 5-6 membered heteroaryl optionally substituted by 1, 2, 3, or 4 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

27. The compound of any one of embodiments 1-18, 23, and 24, or a pharmaceutically acceptable salt thereof, wherein Cy is selected from 5-membered heteroaryl optionally substituted by 1 or 2 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

28. The compound of any one of embodiments 1-18, 23, and 24, or a pharmaceutically acceptable salt thereof, wherein Cy is thiazoyl optionally substituted by 1 or 2 R$^{Cy}$ substituents independently selected from halo, C$_{1-4}$ alkyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

29. The compound of any one of embodiments 1-18, 23, and 24, or a pharmaceutically acceptable salt thereof, wherein Cy is unsubstituted thiazoyl.

30. The compound of any one of embodiments 1-18 and 23 to 28, or a pharmaceutically acceptable salt thereof, wherein each R$^{Cy}$ substituent is independently selected from halo, C$_{1-4}$ alkyl, C$_{1-4}$ haloalkyl, CN, OR$^a$, C(O)R$^b$, C(O)NR$^c$R$^d$, C(O)OR$^a$, NR$^c$R$^d$, NR$^c$C(O)R$^b$, NR$^c$S(O)$_2$R$^b$, S(O)$_2$R$^b$, and S(O)$_2$NR$^c$R$^d$.

31. The compound of any one of embodiments 1-30, or a pharmaceutically acceptable salt thereof, wherein n is 0.

32. The compound of any one of embodiments 1-31, or a pharmaceutically acceptable salt thereof, wherein m is 1.

33. The compound of any one of embodiments 1-31, or a pharmaceutically acceptable salt thereof, wherein m is 2.

34. The compound of embodiment 1 which is selected from:
4-((2-(2,2,2-Trifluoroethyl)-1H-imidazol-4-yl)methyl)pyridine;
4-((2-(3,3,3-Trifluoropropyl)-1H-imidazol-4-yl)methyl) pyridine;
2-(4-(Pyridin-4-ylmethyl)-1H-imidazol-2-yl)acetonitrile;
3-(4-(Pyridin-4-ylmethyl)-1H-imidazol-2-yl)propanenitrile;
rac-4-(1-(2-(2,2,2-Trifluoroethyl)-1H-imidazol-4-yl)ethyl) pyridine;
(R)-4-(1-(2-(2,2,2-Trifluoroethyl)-1H-imidazol-4-yl)ethyl) pyridine;
(S)-4-(1-(2-(2,2,2-Trifluoroethyl)-1H-imidazol-4-yl)ethyl) pyridine;
5-((4-(Pyridin-4-ylmethyl)-1H-imidazol-2-yl)methyl)thiazole;
2,2,2-Trifluoro-1-(4-(pyridin-4-ylmethyl)-1H-imidazol-2-yl)ethanol;
4-((5-(2,2,2-Trifluoroethyl)-1H-1,2,4-triazol-3-yl)methyl) pyridine;
2-(Pyridin-4-ylmethyl)-4-(2,2,2-trifluoroethyl)thiazole;
4-(Pyridin-4-ylmethyl)-2-(2,2,2-trifluoroethyl)thiazole;
rac-4-(1-(5-(2,2,2-trifluoroethyl)-1H-pyrrol-2-yl)ethyl)pyridine;
(S)-2,2,2-Trifluoro-1-(5-(pyridin-4-ylmethyl)-1H-imidazol-2-yl)ethan-1-ol;
(R)-2,2,2-Trifluoro-1-(5-(pyridin-4-ylmethyl)-1H-imidazol-2-yl)ethan-1-ol (12a);
2,2,2-Trifluoro-1-(5-(pyridin-4-ylmethyl)-1H-imidazol-2-yl)ethan-1-one hydrochloride;
(E/Z)-2,2,2-Trifluoro-1-(5-(pyridin-4-ylmethyl)-1H-imidazol-2-yl)ethan-1-one oxime;
4-((5-Methyl-2-(2,2,2-trifluoroethyl)-1H-imidazol-4-yl) methyl)pyridine;
(S)-2,2,2-Trifluoro-1-(4-(pyridin-4-ylmethyl)-1H-imidazol-2-yl)ethanamine;
(R)-2,2,2-Trifluoro-1-(4-(pyridin-4-ylmethyl)-1H-imidazol-2-yl)ethanamine;
(S)-2,2,2-Trifluoro-N-methyl-1-(5-(pyridin-4-ylmethyl)-1H-imidazol-2-yl)ethan-1-amine;
(R)-2,2,2-Trifluoro-N-methyl-1-(5-(pyridin-4-ylmethyl)-1H-imidazol-2-yl)ethan-1-amine;
(S)-2,2,2-Trifluoro-N,N-dimethyl-1-(5-(pyridin-4-ylmethyl)-1H-imidazol-2-yl)ethan-1-amine;
(R)-2,2,2-Trifluoro-N,N-dimethyl-1-(5-(pyridin-4-ylmethyl)-1H-imidazol-2-yl)ethan-1-amine;
(E/Z)-2,2,2-Trifluoro-1-(4-(pyridin-4-ylmethyl)thiazol-2-yl) ethan-1-one oxime;
(R)-2,2,2-Trifluoro-1-(5-(pyridin-4-ylmethyl)thiazol-2-yl) ethan-1-amine;
(S)-2,2,2-Trifluoro-1-(5-(pyridin-4-ylmethyl) thiazol-2-yl) ethan-1-amine;
(S)-(4-(Pyridin-4-ylmethyl)-1H-imidazol-2-yl)(thiazol-5-yl)methanol;
(R)-(4-(Pyridin-4-ylmethyl)-1H-imidazol-2-yl)(thiazol-5-yl)methanol;
(5-((3-Methylpyridin-4-yl)methyl)-1H-imidazol-2-yl)(thiazol-5-yl)methanol;
3,5-Dichloro-4-((2-(2,2,2-trifluoroethyl)-1H-imidazol-5-yl) methyl)pyridine;
1-(4-((3-Chloropyridin-4-yl)methyl)-1H-imidazol-2-yl)-2,2,2-trifluoroethan-1-ol;

(1R)-2,2,2-Trifluoro-1-(4-(1-(pyridin-4-yl)ethyl)-1H-imidazol-2-yl)ethan-1-ol;
(S)-2,2,2-Trifluoro-1-(4-((S)-1-(pyridin-4-yl)ethyl)-1H-imidazol-2-yl)ethan-1-ol;
3-Methyl-4-((2-(2,2,2-trifluoroethyl)-1H-imidazol-4-yl)methyl)pyridine;
(R)-2,2,2-Trifluoro-1-(4-(pyridin-4-ylmethyl)-1H-imidazol-2-yl)-1-(thiazol-5-yl)ethan-1-ol; and
(S)-2,2,2-Trifluoro-1-(4-(pyridin-4-ylmethyl)-1H-imidazol-2-yl)-1-(thiazol-5-yl)ethan-1-ol;
or a pharmaceutically acceptable salt of any of the aforementioned.

35. A pharmaceutical composition comprising at least one pharmaceutically acceptable carrier and a compound of any one of embodiments 1 to 34 or a compound of Formula I:

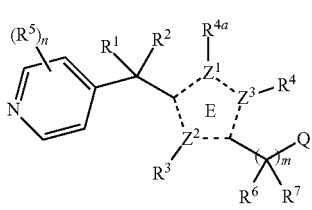

or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, OH, and $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;
each $R^e$ is independently selected from H, $C_{1-4}$ alkyl, and CN;
n is 0, 1, or 2; and
m is 1 or 2.

36. A pharmaceutical composition comprising at least one pharmaceutically acceptable carrier and a compound of any one of embodiments 1 to 34, or a pharmaceutically acceptable salt thereof.

37. A method of inhibiting SARM1 comprising contacting the SARM1 with a compound of any one of embodiments 1 to 34 or a compound of Formula I:

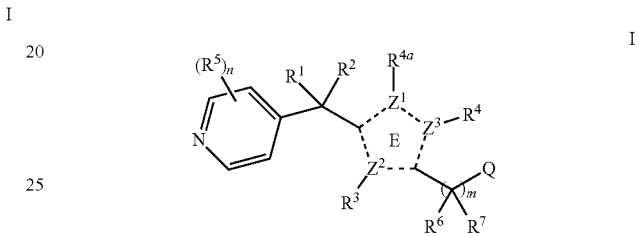

or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, OH, and $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently
selected from OH, CN, amino, halo, $C_{1-4}$ alkyl, $C_{1-4}$ alkoxy, $C_{1-4}$haloalkyl, and $C_{1-4}$haloalkoxy; each $R^e$ is independently selected from H, $C_{1-4}$ alkyl, and CN;
n is 0, 1, or 2; and
m is 1 or 2.

38. A method of inhibiting SARM1 comprising contacting the SARM1 with a compound of any one of embodiments 1 to 34, or a pharmaceutically acceptable salt thereof.

39. The method of embodiment 37 or embodiment 38 wherein the contacting is carried out in vitro.

40. The method of embodiment 37 or embodiment 38 wherein the contacting is carried out in vivo.

41. A method of inhibiting axonal degeneration in a patient in need thereof comprising administering to the patient an inhibiting amount of a compound of any one of embodiments 1 to 34 or a compound of Formula I:

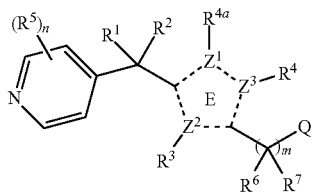

I or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, OH, and $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^c$ $R^d$, $NR^cR^d$, $NR^cC(O)R^b$, $NR^cC(O)OR^a$, $NR^cC(O)NR^c$ $R^d$, $C(=NR^e)R^b$, $C(=NR^e)NR^cR^d$, $NR^cC(=NR^e)NR^c$ $R^d$, $NRS(O)R^b$, $NR^cS(O)_2R^b$, $NR^cS(O)_2NR^cR^d$, $S(O)$ $R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;
each $R^e$ is independently selected from H, $C_{1-4}$ alkyl, and CN;
n is 0, 1, or 2; and
m is 1 or 2.

42. A method of inhibiting axonal degeneration in a patient in need thereof comprising administering to the patient an inhibiting amount of a compound of any one of embodiments 1 to 34; or a pharmaceutically acceptable salt thereof.

43. The method of embodiment 41 or embodiment 42, wherein the axonal degeneration is caused by abnormal reduction or depletion of NAD+ in the axons.

44. A method of treating or preventing a neurological disorder in a patient in need thereof comprising administering to the patient a therapeutically effective amount of a compound of any one of embodiments 1 to 34 or a compound of Formula:

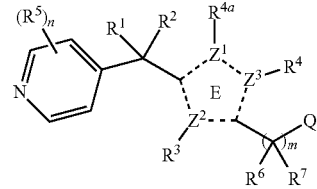

I or a pharmaceutically acceptable salt thereof, wherein:
$Z^1$, $Z^2$, and $Z^3$ are each independently selected from O, S, N, or C, wherein Ring E is a 5-membered aromatic ring;
Q is —CN, —$C_{1-4}$ alkyl-CN, —Cy, —$C_{1-4}$ alkyl-Cy, —$CF_3$, or $C_{1-4}$ alkyl-$CF_3$;
$R^1$ is H;
$R^2$ is H or $C_{1-4}$ alkyl;
$R^3$, $R^4$, and $R^{4a}$ are each independently selected from H, halo, and $C_{1-4}$ alkyl;
each $R^5$ is independently selected from H, halo, and $C_{1-4}$ alkyl, wherein $R^5$ is attached to a carbon atom;
wherein $R^3$ is absent when $Z^2$ is —O—, —S—, or —N=;
wherein $R^4$ is absent when $Z^3$ is —O—, —S—, or —N=;
wherein $R^{4a}$ is absent when $Z^1$ is —O—, —S—, or —N=;
$R^6$ and $R^7$ are each independently selected from H, OH, and $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^c R^d$, $NR^cR^d$, $NR^cC(O)R^b$, $NR^cC(O)OR^a$, $NR^cC(O)NR^c R^d$, $C(=NR^e)R^b$, $C(=NR^e)NR^cR^d$, $NR^cC(=NR^e)NR^c R^d$, $NR^cS(O)R^b$, $NR^cS(O)_2R^b$, $NR^cS(O)_2NR^cR^d$, $S(O) R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$haloalkyl, and $C_{1-4}$haloalkoxy;

each $R^e$ is independently selected from H, $C_{1-4}$ alkyl, and CN;

n is 0, 1, or 2; and m is 1 or 2.

45. A method of treating or preventing a neurological disorder in a patient in need thereof comprising administering to the patient a therapeutically effective amount of a compound of any one of embodiments 1 to 35, or a pharmaceutically acceptable salt thereof.

46. The method of embodiment 44 or embodiment 45 wherein the neurological disorder is a neurodegenerative disease.

47. The method of any one of embodiments 44-46, comprising administering to the patient a therapeutically effective amount of a compound of any one of embodiments 1 to 35, or a pharmaceutically acceptable salt thereof, in combination with a further pharmaceutically active agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

At various places in the present specification a di-valent or linking group may be present. Each linking group is understood as linking in either direction. That is, if a linking group is described as -A-B—, then it is understood, unless otherwise specified, that the linking group is not directionally limited and can also be —B-A-. For example, when a linking group is written as —C(=O)—O—, it also means —O—C(=O)—.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency. In some embodiments, an atom substituted by oxo (=O) has two hydrogen atoms replaced by the oxo substituent.

As used herein, the term "$C_{i-j}$" where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl. In some embodiments, the alkyl group is methyl.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino," employed alone or in combination with other terms, refers to $NH_2$.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{27}$ monocyclic heterocycloalkyl group. In some embodiments, the heterocycloalkyl group is a morpholine ring, pyrrolidine ring, piperazine ring, piperidine ring, tetrahydropyran ring, tetrahydropyridine, azetidine ring, or tetrahydrofuran ring.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl. In some embodiments, the aryl group is phenyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen.

In some embodiments, the heteroaryl group is a 5-14 membered heteroaryl group. In some embodiments, the heteroaryl group is a 5-10 membered heteroaryl group. In some embodiments, the heteroaryl group is a 5-6 membered heteroaryl group. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H— and 3H-imidazole, 1H—, 2H— and 4H-1,2,4-triazole, 1H— and 2H-isoindole, and 1H— and 2H-pyrazole.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric isomers, tautomers, and isotopes of the structures depicted, unless otherwise specified. The term "compound" is also not limited by the way in which it was made. Thus, a compound of the invention includes molecules that were made by a synthetic process or by a biological process (such as through enzyme conversion or metabolism), or combinations thereof.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of a compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Methods of Use

Compounds of the invention can inhibit the activity of SARM1. For example, the compounds of the invention can be used to inhibit activity or a function of SARM1 in a cell or in an individual or patient in need of inhibition of the enzyme by administering an inhibiting amount of a compound of the invention to the cell, individual, or patient. As used herein, the term "in a cell" includes both inside the cell membrane and on the surface of the cell membrane.

Compounds of the invention, as SARM1 inhibitors, can increase levels of NAD+ in a cell. Accordingly, the present invention is further directed to a method of increasing the level of NAD+ in a sample or in a patient, comprising contacting the sample or administering to the patient a compound of the invention, or a pharmaceutically acceptable salt thereof, wherein the increased level of NAD+ is relative to the level of NAD+ prior to the contacting or administering.

Compounds of the invention, as SARM1 inhibitors, can inhibit axonal degeneration. Accordingly, the present invention is further directed to a method of inhibiting axonal degeneration in a sample or in a patient, comprising contacting the sample or administering to the patient an inhibiting amount of a compound of the invention, or a pharmaceutically acceptable salt thereof.

The compounds of the invention are useful in the treatment and prevention of various diseases associated with abnormal expression or activity of SARM1. For example, the compounds of the invention are useful in the treatment and prevention of neurological disorders. The term "neurological disorder" generally refers to a disorder affecting the nervous system, including the central nervous system or the peripheral nervous system. The term "neurological disorder" also includes ocular indications having a nexus to the nervous system.

In some embodiments, the neurological disorder treatable or preventable by administration of a compound of the invention includes neurodegenerative diseases. Neurodegenerative diseases are characterized by damage to the central nervous system and can be identified by progressive dysfunction, degeneration and death of specific populations of neurons which are often synaptically interconnected. Examples of neurodegenerative diseases include Parkinson's disease (PD), Alzheimer's disease (AD), Huntington's disease (HD), prion disease, motor neuron diseases (MND), spinocerebellar ataxia (SCA), spinal muscular atrophy (SMA), amyotrophic lateral sclerosis (ALS), and epilepsy.

Examples of neurological disorders treatable or preventable according to the methods of the invention include spinal muscular atrophy (SMA), Chemotherapy Induced Peripheral Neuropathy (representative chemotherapeutic agents include vinca-alkaloids, taxols and platins), multiple sclerosis (MS), traumatic brain injury (TBI), spinal cord injury, stroke, Parkinson' disease, glaucoma, Huntington's disease, Alzheimer's disease, Charcot-Marie-Tooth disease (CMT), retinitis pigmentosa (RP), age-related macular degeneration (AMD), small fiber neuropathies, peripheral neuropathy (e.g., viral neuropathy), spinocerebellar ataxias, cystic fibrosis, familial amyloidotic polyneuropathy, spongiform encephalopathies, spinal and bulbar muscular atrophy, hereditary dentatorubral-pallidoluysian atrophy, adrenoleukodystrophy, adrenomyeloneuropathy, Alexander's disease, amyotrophic lateral sclerosis (ALS), Bassen-Kornzweig syndrome, Bell's palsy, progressive supra nuclear palsy (PSP), central pontine myelolysis, cluster headache, congenital hypomyelination, corticobasal degeneration, Creutzfeldt-Jakob disease, epilepsy, dementia (e.g., frontotemporal dementia and Lewy body dementia), demyelination disorders (e.g., ischemic demyelination), encephalomyelitis, Friedrich's ataxia, Gaucher's disease, hereditary sensory and autonomic neuropathy (HSAN), Hurler syndrome, Krabbe's disease, metachromatic leukodystrophy, migraine and tension headaches, mild cognitive impairment, motor spinoneuron disease, neuromyelitis optica, Niemann- Pick disease, optic neuritis, Pelizaeus Merzbacher disease, peripheral neuropathy, periventricular leukomalacia, postherpetic neuralgia, prion disease, progressive supranuclear palsy, progressive multifocal leukoencephalopathy, Tay-Sacks disease, thoracic disc herniation, traverse myelitis, trigeminal neuralgia, Wallerian degeneration, cerebellar degeneration, chiari malformation, dystonia, encephalitis (e.g., pediatric viral encephalitis and La Crosse virus encephalitis), hyperekplexia, multifocal motor neuropathy, muscular dystrophy, myasthenia gravis, myopathy, neurofibromatosis, neuronal ceroid lipofuscinosis, neuropathies (e.g., peripheral neuropathy), pseudobulbar affect, restless legs syndrome, spina bifida, syringomyelia, thoracic outlet syndrome, and transverse myelitis.

In other embodiments, the neurological disorder treatable or preventable by administration of a compound of the invention is a neuropathy. As used herein, the term "neuropathy" refers broadly to diseased conditions of the nervous system, including polyneuropathy; neuropathy, ataxia, and retinosa pigmentosa (NARP); familial amyloid neuropathies; diabetic neuropathy (peripheral neuropathy due to diabetes mellitus); peripheral neuropathy (e.g., chemotherapy-induced peripheral neuropathy (CIPN), including CIPN caused by vinca alkaloids, bortezomib, lxabepilone, thalidomide and its analogs, taxanes, and platinum-based agents); and cranial neuropathy (e.g., auditory neuropathy and optic neuropathy). The term also includes other neuropathies associated with genetic disorders (e.g., NMNAT2 genetic mutation disorders).

In still other embodiments, the neurological disorder treatable or preventable by administration of a compound of the invention is an ocular neuropathy (e.g., optic neuropathy). The term "optic neuropathy" refers to damage to the optic nerve from a number of causes. Types of optic neuropathy include ischemic optic neuropathy (e.g., anterior and posterior ischemic optic neuropathy); optic neuritis (e.g., chronic relapsing inflammatory optic neuropathy (CRION), single isolated optic neuritis (SION), and relapsing isolated optic neuritis); compressive optic neuropathy; infiltrative optic neuropathy; traumatic optic neuropathy; mitochondrial optic neuropathies; and hereditary optic neuropathies (e.g., Leber's hereditary optic neuropathy (LHON), hereditary neuropathy with liability to pressure palsy (HNPP), and dominant optic atrophy).

In still other embodiments, the neurological disorder treatable or preventable by administration of a compound of the invention is multiple sclerosis (MS), chemotherapy-induced peripheral neuropathy (CIPN), amyotrophic lateral sclerosis (ALS), glaucoma, traumatic brain injury (TBI), or stroke.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" SARM1 or "contacting" a cell with a compound of the invention includes the administration of a compound of the present invention to an individual or patient, such as a human, having SARM1, as well as, for example, introducing a compound of the invention into a sample containing a cellular or purified preparation containing SARM1.

As used herein, the term "individual" or "patient," used interchangeably, refers to mammals, and particularly humans. The individual or patient can be in need of treatment.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the phrase "inhibiting amount" refers to the amount of active compound or pharmaceutical agent that elicits a measurable SARM1 inhibition or axonal degeneration in a tissue, system, animal, individual or human.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease. In some embodiments, the invention is directed to a method of preventing a disease in a patient, by administering to the patient a therapeutically effective amount of a compound of the invention, or a pharmaceutically acceptable salt thereof.

Combination Therapy

One or more additional pharmaceutically active agents or treatment methods can be used in combination with the compounds of the present invention. The agents can be combined with the present compounds in a single dosage form, or the agents can be administered simultaneously or sequentially as separate dosage forms. Examples of additional agents include acamprosate, agomelatine, almotriptan, amantadine, amisulpride, amitriptyline, apomorphine, aripiprazole, asenapine, atomoxetine, baclofen, botulinum toxin type A, bromocriptine, buccal midazolam, buprenorphine, buspirone, cabergoline, carbamazepine, chlordiazepoxide, chlorpromazine, citalopram, clobazam, clomethiazole, clomipramine, clonazepam, clozapine, denzapine, co-beneldopa, co-careldopa, dantrolene, dexamfetamine, diazepam, divalproex sodium, donepezil, doxepin, duloxetine, eletriptan, entacapone, epinephrine, escitalopram, eslicarbazepine, ethosuximide, fingolimod, fluoxetine, flupentixol, flupentixol, fluphenazine long-acting injection (modecate), fluvoxamine (Faverin), frovatriptan, gabapentin, galantamine, haloperidol, imipramine, lacosamide, lamotrigine, levetiracetam, levomepromazine, lisdexamfetamine, lithium, lofepramine, loprazolam, lorazepam, lormetazepam, lurasidone, melatonin, memantine, methylphenidate, mianserin, mirtazapine, moclobemide, modafinil, naratriptan, neostigmine, nitrazepam, nortriptyline, olanzapine, orlistat, orphenadrine, oxazepam, oxcarbazepine, paliperidone, paliperidone, paroxetine, perampanel, pergolide, pericyazine, phenobarbital, phenytoin, piracetam, pizotifen, pramipexole, pregabalin, primidone, prochlorperazine, procyclidine, pyridostigmine, quetiapine, rasagiline, reboxetine, risperidone, rivastigmine, rizatriptan, ropinirole, rotigotine, rufinamide, selegiline, sertraline, sodium oxybate, sodium valproate, sulpiride, sumatriptan, temazepam, tetrabenazine, tiagabine, tizanidine, tolcapone, topiramate, trazodone, trihexyphenidyl, trimipramine, valproate semisodium, venlafaxine, vigabatrin, vortioxetine, zolmitriptan, zolpidem, zonisamide, zopiclone, and zuclopenthixol.

In some embodiments, the one or more additional pharmaceutically active agent can include a neuroprotective agent. In some embodiments, the neuroprotective agent is a dual leucine-zipper kinase (DLK) inhibitor. In some embodiments, the neuroprotective agent is a nicotinamide phosphoribosyltransferase (NAMPT) inhibitor.

In some embodiments, the one or more additional pharmaceutically active agent can be NAD+ or an NAD+ precursor. NAD+ precursors include, for example, nicotinamide riboside (NR), nicotinic acid (NA), nicotinic acid riboside (NaR), nicotinamide (NAM), nicotinamide mononucleotide (NMN), nicotinic acid mononucleotide (NaMN), tryptophan, vitamin B3, and nicotinic acid adenine dinucleotide (NAAD).

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier.

These compositions can be prepared in a manner well known in the pharmaceutical art, and can be administered by a variety of routes, depending upon whether local or systemic treatment is desired and upon the area to be treated. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular (e.g., eye drops or intravitreal, subconjunctival, subtenon, or retrobulbar injection), or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsule s. This solid pre-formulation is then subdivided into unit dosage forms of the type described above.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of SARM1 according to one or more of the assays provided herein.

EXAMPLES

General Experimental:

All reactions sensitive to air or moisture were carried out in flame-dried glassware under an atmosphere of nitrogen. All commercially available reagents were purchased from suppliers such as Sigma-Aldrich (MilliporeSigma), Combi-Blocks, Enamine, Sinopharm Chemical Reagent Co. (SCRC), and Alfa Aesar and were used without purification unless otherwise noted. Proton nuclear magnetic resonance ($^1$H NMR) spectra were recorded on Bruker AVIII 400 or Bruker AVIII 500 spectrometers. Samples were dissolved in deuterated chloroform (CDCl$_3$), dimethyl sulfoxide (DMSO-d$_6$), acetonitrile (CD$_3$CN) or methanol (CD$_3$OD). Chemical shifts are recorded in parts per million (ppm) and are referenced to the centerline of deuterochloroform ($\delta$ 7.26 ppm), of DMSO-d$_6$ ($\delta$ 2.50 ppm), of CD$_3$CN ($\delta$ 1.94 ppm) or of CD$_3$OD ($\delta$ 3.31 ppm). Data were recorded as follows: chemical shift, multiplicity (s=singlet, d=doublet, t=triplet, q=quartet, qt=quintet, m=multiplet, br=broad). Coupling constants (J values) are given in Hertz (Hz). Low resolution ESI mass spectra were recorded on a either an Agilent 1200 HPLC/6100 SQ system or an Agilent 1260 Infinity II HPLC/6125 SQ system. LCMS measurements were recorded on Agilent 1200 HPLC/6100 SQ System.

LIST OF ABBREVIATIONS aq aqueous
Boc tert-butyloxycarbonyl
Boc$_2$O Boc-anhydride or di-tert-butyl dicarbonate
CDI 1,1'-carbonyl-diimidazole
d day(s)
D $^2$H (deuterium)
DABCO 1,4-diazabicyclo[2.2.2]octane
dba dibenzylideneacetone
DCM dichloromethane
DMP Dess-Martin periodinane or 3-Oxo-1$\lambda^5$,2-benziodoxole-1,1,1(3H)-triyl triacetate
DEA diethylamine
DHP 3,4-dihydropyran
DIAD diisopropyl azodicarboxylate
DIPEA N,N-diisopropylethylamine
DMAP 4-(dimethylamino)pyridine
DMF dimethylformamide
DMSO dimethylsulfoxide
DPPA diphenyl phosphoryl azide
EDC HCl N-ethyl-N'-(3-dimethylaminopropyl)carbodiimide hydrochloride
ESI-MS electrospray ionization-mass spectrometry
Et ethyl
EtOAc ethyl acetate
EtOH ethanol
equiv equivalent(s)
FA formic acid
h hour(s)
HATU 1-[bis(dimethylamino)methylene]-1H-1,2,3-triazolo[4,5-b]pyridinium 3-oxide hexafluorophosphate
HOBt 1-hydroxybenzotriazole
LAH lithium aluminum hydride
LCMS liquid chromatography mass spectrometry
LiHMDS lithium bis(trimethylsilyl)amide
MS mass spectrometry
MeCN acetonitrile
MeOH methanol
MHz megahertz
min minute(s)
mg milligram(s)
mL milliliter(s)
mmol millimole(s)
M molar
MeCN acetonitrile
mol mole(s)
Ms methanesulfonyl
MW microwave
N normal
NBS N-bromosuccinimide
NCS N-chlorosuccinimide
OTf trifluoromethanesulfonate
Pd/C palladium on carbon
PE petroleum ether
Ph phenyl
PTSA p-toluenesulfonic acid
$^1$H NMR proton nuclear magnetic resonance
RP-HPLC reverse-phase high performance liquid chromatography
RT retention time
rt room temperature
sat saturated
SEM 2-(trimethylsilyl)ethoxymethyl SFC supercritical fluid chromatography
T3P propylphosphonic anhydride
TBAF tetrabutylammonium fluoride
TBPH tert-butyl hydroperoxide solution (Luperox®, TBH70X)
t-BuOK potassium tert-butoxide
TEA triethylamine
TFA trifluoroacetic acid
THF tetrahydrofuran
THP tetrahydropyran
TLC thin layer chromatography
Tol toluene
TosMIC p-toluenesulfonylmethyl isocyanide
wt % weight percent
v/v % volume by volume percent
w/v % weight by volume percent
XPhos 2-dicyclohexylphosphino-2',4',6'-triisopropylbiphenyl Example 1: 4-((2-(2,2,2-Trifluoroethyl)-1H-imidazol-4-yl)methyl)pyridine

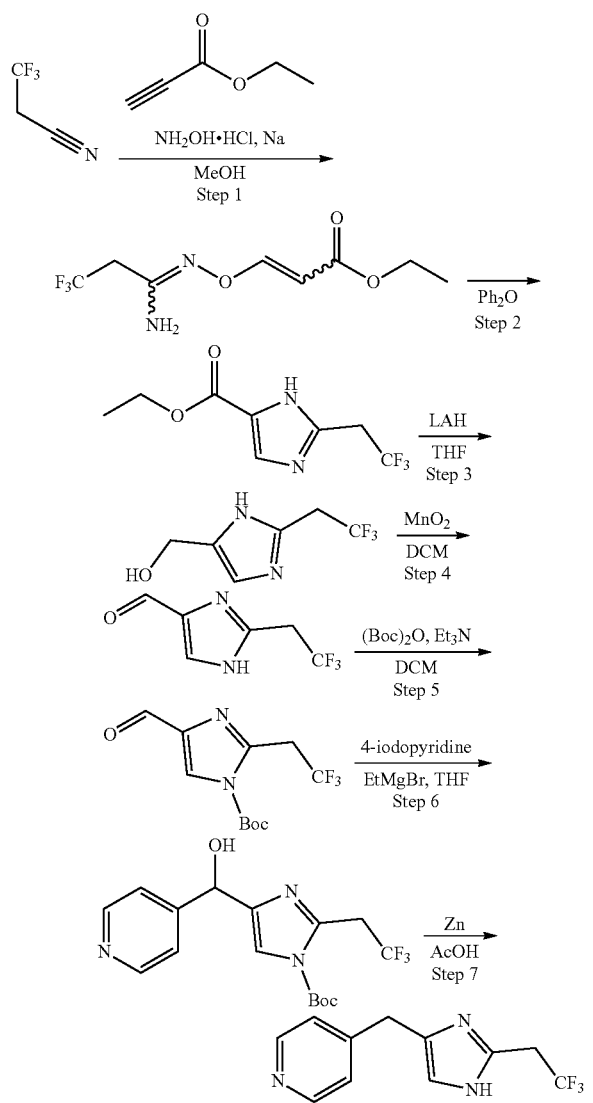

Step 1: Ethyl 3-(((1-amino-3,3,3-trifluoropropylidene)amino)oxy)acrylate. To a flask containing sodium metal (843 mg, 36.7 mmol) in MeOH (10 mL), a suspension of NH$_2$OH HCl (2.55 g, 36.7 mmol) in MeOH (10 mL) was added slowly using an addition funnel. The resulting mixture was stirred for 15 min. The suspension was filtered, the filtrate was cooled to 0° C. and 3,3,3-trifluoropropionitrile (4 g, 36.7 mmol) was added. The reaction mixture was stirred for 1 h. The solvent was evaporated under reduced pressure and the resulting oil was dissolved in MeCN (150 mL) and TEA (3.72 g, 36.7 mmol) was added to the solution. The resulting mixture was heated to 80° C. and a solution of ethyl propiolate (3.6 g, 36.7 mmol) in MeCN (20 mL) was added. The resulting reaction was stirred at 80° C. for 18 h. The reaction was then cooled to room temperature, the solvent was evaporated under reduced pressure and the crude product was purified by silica gel column chromatography to yield ethyl 3-(((1-amino-3,3,3-trifluoropropylidene)amino)oxy)acrylate (7.1 g, 81%) as a yellow oil. LCMS ESI-MS m/z: 241 [M+H]$^+$.

Step 2: Ethyl 2-(2,2,2-trifluoroethyl)-1H-imidazole-5-carboxylate. Ethyl 3-(((1-amino-3,3,3-trifluoropropylidene)amino)oxy)acrylate (5 g, 20.8 mmol) and Ph$_2$O (60 mL) was heated to 180° C. and stirred for 30 min. The reaction was cooled and the crude mixture was purified via silica gel column chromatography to yield the ethyl 2-(2,2,2-trifluoroethyl)-1H-imidazole-5-carboxylate (1.8 g) as a yellow oil. This compound was used in the next step without further purification. LCMS ESI-MS m/z: 223 [M+H]$^+$.

Step 3: (2-(2,2,2-Trifluoroethyl)-1H-imidazol-5-yl)methanol. To a solution of ethyl 2-(2,2,2-trifluoroethyl)-1H-imidazole-5-carboxylate (1 g, 4.5 mmol) in anhydrous THF (50 mL) was added 1 M LAH in THF (11.2 mL, 11.2 mmol) at 0° C. The resulting mixture was warmed to room temperature and stirred for 3 h. The reaction was quenched by the addition of water and filtered. The filtrate was dried over Na$_2$SO$_4$, filtered, and concentrated under reduced pressure to yield (2-(2,2,2-trifluoroethyl)-1H-imidazol-5-yl)methanol (560 mg) as a yellow solid. This compound was used in the next step without further purification. LCMS ESI-MS m/z: 181 [M+H]$^+$.

Step 4: 2-(2,2,2-Trifluoroethyl)-1H-imidazole-4-carbaldehyde. To a solution of (2-(2,2,2-trifluoroethyl)-1H-imidazol-5-yl)methanol (560 mg, 3.11 mmol) in DCM (50 mL) and MeCN (50 mL) was added MnO$_2$ (2.64 g, 31.1 mmol), and the resulting mixture was stirred at room temperature for 3 h. The reaction mixture was filtered and concentrated under reduced pressure to yield the crude 2-(2,2,2-trifluoroethyl)-1H-imidazole-4-carbaldehyde (498 mg) as a yellow solid. This compound was used in the next step without further purification. LCMS ESI-MS m/z: 179 [M+H]$^+$.

Step 5: tert-Butyl 4-formyl-2-(2,2,2-trifluoroethyl)-1H-imidazole-1-carboxylate. A solution of 2-(2,2,2-trifluoroethyl)-1H-imidazole-4-carbaldehyde (1 g, 5.61 mmol), TEA (1.13 g, 11.2 mmol) and (Boc)$_2$O (2.45 g, 11.2 mmol) in DCM (40 mL) was stirred at room temperature for 16 h. The mixture was quenched by the addition of H$_2$O (20 mL) and the organics were extracted into EtOAc (3×100 mL). The organic layers were combined, dried over anhydrous Na$_2$SO$_4$, filtered, and concentrated under reduced pressure. The residue was purified via silica gel column chromatography to yield tert-butyl 4-formyl-2-(2,2,2-trifluoroethyl)-1H-imidazole-1-carboxylate (716 mg, 46%) as a brown oil. LCMS ESI-MS m/z: 179 [M+H-Boc]$^+$.

Step 6: tert-Butyl 4-(hydroxy(pyridin-4-yl)methyl)-2-(2,2,2-trifluoroethyl)-1H-imidazole-1-carboxylate. A solution of 4-iodopyridine (839 mg, 4.09 mmol) in THF (30 mL) was cooled to 0° C., and EtMgBr (4.10 mL, 4.09 mmol, 1.0 M in THF) was added to it dropwise. The mixture was stirred at 0° C. for 1 h, and tert-butyl 4-formyl-2-(2,2,2-trifluoroethyl)-1H-imidazole-1-carboxylate (716 mg, 2.57 mmol) was added at 0° C. After the addition, the resulting mixture was warmed to room temperature and stirred for 16 h. The mixture was quenched with the addition of $H_2O$ (20 mL) and the organics were extracted into EtOAc (3×80 mL). The combined organic layers were dried over anhydrous $Na_2SO_4$, filtered, and concentrated under reduced pressure to yield the crude tert-butyl 4-(hydroxy(pyridin-4-yl)methyl)-2-(2,2,2-trifluoroethyl)-1H-imidazole-1-carboxylate (2.87 g) as a brown oil. This compound was used in the next step without further purification. LCMS ESI-MS m/z: 358 [M+H]$^+$.

Step 7: 4-((2-(2,2,2-Trifluoroethyl)-1H-imidazol-4-yl)methyl)pyridine. A mixture of crude tert-butyl 4-(hydroxy(pyridin-4-yl)methyl)-2-(2,2,2-trifluoroethyl)-1H-imidazole-1-carboxylate (2.87 g, 8.03 mmol) and Zn (5.22 g, 80.3 mmol) in AcOH (50 mL) was heated to 130° C. for 16 h. The resulting mixture was filtered, and the precipitate rinsed with MeOH (50 mL). The filtrate was concentrated under reduced pressure. To this residue was added saturated $NaHCO_3$ (50 mL) and the organics were extracted into DC/MeOH (10:1, 3×50 mL). The combined organic layers were dried over anhydrous $Na_2SO_4$, filtered, and concentrated under reduced pressure. The residue was purified by prep-HPLC to yield 4-((2-(2,2,2-trifluoroethyl)-1H-imidazol-4-yl)methyl)pyridine (308 mg, 31%) as a white solid. $^1$H NMR (400 MHz, DMSO-d6, ppm): δ 12.01 (s, 1H), 8.44 (d, J=6.0 Hz, 2H), 7.23 (d, J=6.0 Hz, 2H), 6.84 (s, 1H), 3.84 (s, 2H), 3.65 (q, J=10.8 Hz, 2H). LCMS ESI-MS m/z: 242 [M+H]$^+$.

Example 2: 4-((2-(3,3,3-trifluoropropyl)-1H-imidazol-4-yl)methyl)pyridine

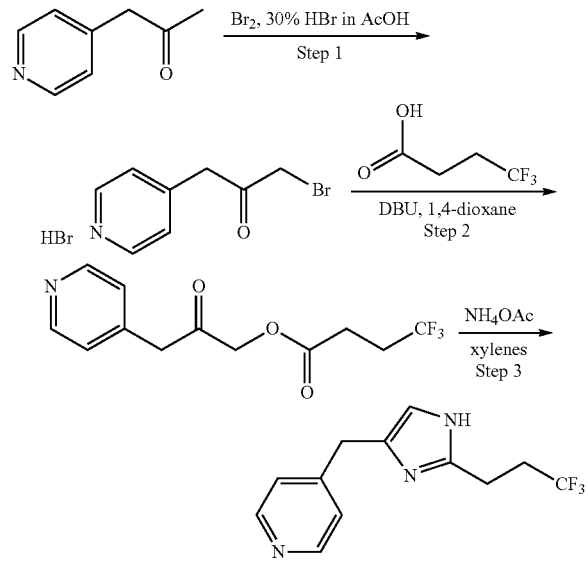

Step 1: 1-Bromo-3-(pyridin-4-yl)propan-2-one hydrobromide. To a stirred mixture of 1-(pyridin-4-yl)propan-2-one (25 g, 185 mmol), HBr (30% in AcOH) (250 mL) was added bromine (29.6 g, 185 mmol) dropwise at 15° C. under a nitrogen atmosphere. The mixture was stirred for 5 h at room temperature. The mixture was diluted with $Et_2O$ (1 L). The resulting mixture was filtered and the filter cake was rinsed with $Et_2O$ (2×20 mL). This resulted in 1-bromo-3-(pyridin-4-yl) propan-2-one hydrobromide (49.8 g) as a light-yellow solid upon concentration under reduced pressure. This compound was used in the next step without further purification. LCMS ESI-MS m/z: 214, 216 [M+H]$^+$.

Step 2: 2-Oxo-3-(pyridin-4-yl)propyl-4,4,4-trifluorobutanoate. A mixture of 4,4,4-trifluorobutanoic acid (3.32 g, 23.3 mmol) and DBU (8.89 g, 58.4 mmol) in 1,4-dioxane (150 mL) was stirred for 5 min at room temperature under a nitrogen atmosphere. To this mixture was added 1-bromo-3-(pyridin-4-yl)propan-2-one (5 g, 23.4 mmol). The resulting mixture was stirred for 3 h at room temperature under a nitrogen atmosphere. The resulting mixture was extracted into EtOAc (3×500 mL). The combined organic layers were washed with brine (2×300 mL), dried over anhydrous $Na_2SO_4$ and filtered. The filtrate was concentrated under reduced pressure to provide 2-oxo-3-(pyridin-4-yl)propyl 4,4,4-trifluorobutanoate (2 g) as a light yellow solid. This compound was used in the next step without further purification. LCMS ESI-MS m/z: 276 [M+H]$^+$.

Step 3: 4-((2-(3,3,3-trifluoropropyl)-1H-imidazol-4-yl)methyl)pyridine. A mixture of 2-oxo-3-(pyridin-4-yl)propyl-4,4,4-trifluorobutanoate (0.2 g, 0.727 mmol) and ammonium acetate (0.56 g, 7.27 mmol) in 1,2-dimethylbenzene (4 mL) was stirred for 10 min at 160° C. in a microwave tube (×10 reactions for a total of 2 g of 2-oxo-3-(pyridin-4-yl)propyl-4,4,4-trifluorobutanoate). The combined mixture was purified by prep-HPLC to afford 4-((2-(3,3,3-trifluoropropyl)-1H-imidazol-4-yl)methyl)pyridine (79.2 mg, 4.3%) as a yellow solid. $^1$H NMR (300 MHz, DMSO-d$_6$, ppm): δ 11.65 (s, 1H), 8.61-8.33 (m, 2H), 7.33-7.12 (m, 2H), 6.76 (s, 1H), 3.80 (s, 2H), 2.89-2.75 (m, 2H), 2.74-2.55 (m, 2H). LCMS ESI-MS m/z: 256 [M+H]$^+$.

Example 3: 2-(4-(Pyridin-4-ylmethyl)-1H-imidazol-2-yl)acetonitrile

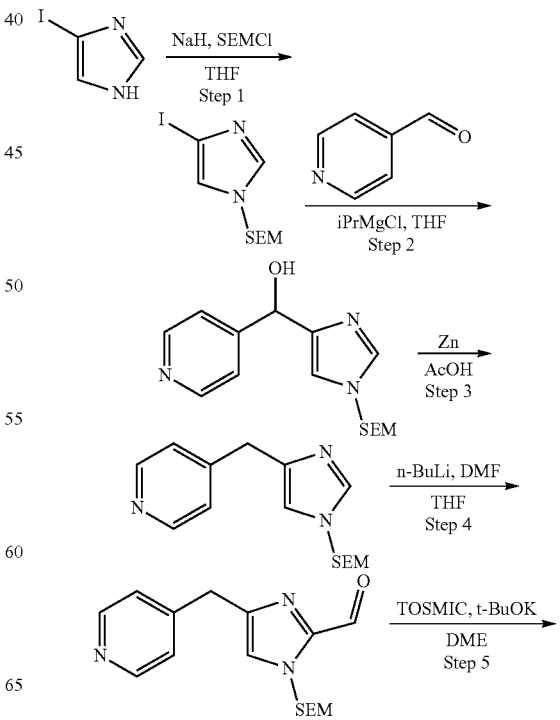

-continued

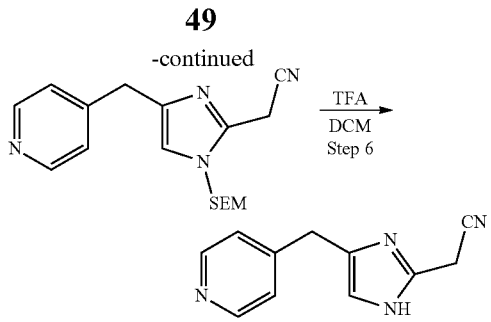

Step 1: 4-Iodo-1-((2-(trimethylsilyl)ethoxy)methyl)-1H-imidazole. A solution of 4-iodo-1H-imidazole (10 g, 0.052 mol) in anhydrous THF (50 mL) was cooled to 0° C., and NaH (2.47 g, 0.062 mol, 60%) was added. The reaction mixture was stirred for 1 h at 0° C., followed by the addition of SEM-Cl (10.3 g, 0.062 mol). The reaction mixture was then warmed to room temperature and stirred for 2 h. The reaction was quenched by the addition of H$_2$O (20 mL) and the resulting mixture was extracted into EtOAc (3×100 mL). The combined organic layers were dried over anhydrous Na$_2$SO$_4$, filtered, and concentrated under reduced pressure to provide the crude residue. The crude residue was purified by silica gel column chromatography to give 4-iodo-1-((2-(trimethylsilyl)ethoxy)methyl)-1H-imidazole (9.58 g, 57%) as a brown liquid. LCMS ESI-MS m/z: 325 [M+H]$^+$.

Step 2: Pyridin-4-yl(1-((2-(trimethylsilyl)ethoxy)methyl)-1H-imidazol-4-yl)methanol. To a solution of 4-iodo-1-((2-(trimethylsilyl)ethoxy)methyl)-1H-imidazole (8.52 g 0.026 mol) in THF (50 mL), iPrMgCl (24.3 mL, 0.032 mol, 1.3 Min THF) was added at 0° C. The mixture was stirred 1 h at 0° C., and isonicotinaldehyde (3.38 g, 0.032 mol) was added. The resulting mixture was warmed to room temperature and stirred for 16 h. The mixture was then quenched by the addition of H$_2$O (20 mL) and extracted into EtOAc (3×100 mL). The combined organic layers were dried over anhydrous Na$_2$SO$_4$, filtered, and concentrated under reduced pressure to provide pyridin-4-yl(1-((2-(trimethylsilyl)ethoxy)methyl)-1H-imidazol-4-yl)methanol (10.4 g) as a brown liquid which was taken to next step without further purification. LCMS ESI-MS m/z=306 [M+H]$^+$.

Step 3: 4-((1-((2-(Trimethylsilyl)ethoxy)methyl)-1H-imidazol-4-yl)methyl)pyridine. A solution of pyridin-4-yl(1-((2-(trimethylsilyl)ethoxy)methyl)-1H-imidazol-4-yl)methanol (10.4 g, 0.034 mol) and Zn (22.2 g, 0.34 mol) in AcOH (100 mL) was heated to 130° C. and stirred for 16 h. The mixture was filtered and rinsed with MeOH (50 mL). The filtrate was then concentrated under reduced pressure. The residue was added to a solution of saturated NaHCO$_3$ (200 mL) and the organics were extracted into EtOAc (3×200 mL). The combined organic layers were dried over anhydrous Na$_2$SO$_4$, filtered, and concentrated under reduced pressure. The crude residue was purified by silica gel column to provide 4-((1-((2-(trimethylsilyl)ethoxy)methyl)-1H-imidazol-4-yl)methyl)pyridine (5.50 g) as a brown liquid which was taken to next step without further purification. LCMS ESI-MS m/z: 290 [M+H]$^+$.

Step 4: 4-(Pyridin-4-ylmethyl)-1-((2-(trimethylsilyl)ethoxy)methyl)-1H-imidazole-2-carbaldehyde. To a stirred solution of 4-((1-((2-(trimethylsilyl)ethoxy)methyl)-1H-imidazol-4-yl)methyl)pyridine (2.22 g, 7.67 mmol) in anhydrous THF (20 mL) at −70° C., n-BuLi (9.2 mL, 23 mmol, 2.5 M solution in hexane) was added under nitrogen atmosphere. The reaction mixture was stirred at −70° C. for 2 h, followed by the addition of DMF (0.841 g, 11.5 mmol). The mixture was then warmed to room temperature and stirred for 16 h. The resulting mixture was quenched by the addition of H$_2$O (20 mL) and the organics were extracted into EtOAc (3×100 mL). The combined organic layers were dried over anhydrous Na$_2$SO$_4$, filtered, and concentrated under reduced pressure. The crude residue was purified by silica gel column chromatography to yield 4-(pyridin-4-ylmethyl)-1-((2-(trimethylsilyl)ethoxy)meth yl)-1H-imidazole-2-carbaldehyde (1.05 g, 43%) as a brown oil. LCMS ESI-MS m/z: 318 [M+H]$^+$.

Step 5: 2-(4-(Pyridin-4-ylmethyl)-1-((2-(trimethylsilyl)ethoxy)methyl)-1H-imidazol-2-yl)acetonitrile. To a stirred solution of 4-(pyridin-4-ylmethyl)-1-((2-(trimethylsilyl)ethoxy))methyl)-1H-imidazole-2-carbaldehyde (250 mg, 0.788 mmol) and TosMIC (231 mg, 1.18 mmol) in DME (10 mL), t-BuOK (134 mg, 1.18 mmol) was added. The mixture was stirred at room temperature for 2 h, and then MeOH (50 mL) was added. The resulting mixture was heated to reflux and stirred for 2 h. At this time, the reaction was quenched by the addition of H$_2$O (20 mL) and extracted into EtOAc (3×50 mL). The combined organic layers were dried over anhydrous Na$_2$SO$_4$, filtered, and concentrated under reduced pressure to yield 2-(4-(pyridin-4-ylmethyl)-1-((2-(trimethylsilyl)ethoxy)methyl)-1H-imidazol-2-yl)acetonitrile (300 mg) as brown liquid which was taken to next step without further purification. LCMS ESI-MS m/z: 329 [M+H]$^+$.

Step 6: 2-(4-(Pyridin-4-ylmethyl)-1H-imidazol-2-yl)acetonitrile. A solution of 2-(4-(pyridin-4-ylmethyl)-1-((2-(trimethylsilyl)ethoxy)methyl)-1H-imidazol-2-yl)acetonitrile (300 mg, 0.913 mmol) in DCM/TFA (10 mL, v/v=2:1) was stirred at room temperature for 3 h. The volatiles were removed under reduced pressure, the residue was added to a solution of saturated NaHCO$_3$ (20 mL), and the organics were extracted into EtOAc (3×20 mL). The combined organic layers were dried over anhydrous Na$_2$SO$_4$, filtered, and concentrated under reduced pressure. The crude residue was purified prep-HPLC to yield 2-(4-(pyridin-4-ylmethyl)-1H-imidazol-2-yl)acetonitrile (37 mg, 24%) as a brown oil. $^1$H NMR (400 MHz, DMSO-d6, ppm): δ 11.99 (s, 1H), 8.44 (d, J=6.8 Hz, 2H), 7.23 (d, J=6.0 Hz, 2H), 6.84 (s, 1H), 4.04 (s, 2H), 3.82 (s, 2H). LCMS ESI-MS m/z: 199 [M+H]$^+$.

Example 4: 3-(4-(Pyridin-4-ylmethyl)-1H-imidazol-2-yl)propanenitrile

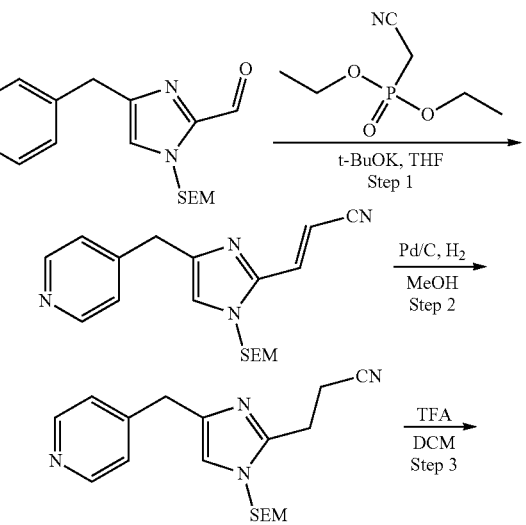

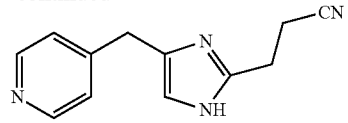

Step 1: (E)-3-(4-(Pyridin-4-ylmethyl)-1-((2-(trimethylsilyl)ethoxy)methyl)-1H-imidazol-2-yl)acrylonitrile. A stirred solution of diethyl(cyanomethyl)phosphonate (167 mg, 0.945 mmol) in THF (10 mL) was cooled to 0° C., then t-BuOK (106 mg, 0.945 mmol) was added. After the mixture was stirred at 0° C. for 1 h, 4-(pyridin-4-ylmethyl)-1-((2-(trimethylsilyl)ethoxy)methyl)-1H-imidazole-2-carbaldehyde (Example 3, Step 4, 250 mg, 0.788 mmol) was added. The resulting mixture was stirred at room temperature for 2 h. The reaction was then quenched by the addition of H₂O (20 mL) and the organics were extracted into EtOAc (3×50 mL). The combined organic layers were dried over anhydrous Na₂SO₄, filtered, and concentrated under reduced pressure. The residue was purified by silica gel column chromatography to yield (E)-3-(4-(pyridin-4-ylmethyl)-1-((2-(trimethylsilyl)ethoxy)methyl)-1H-imidazol-2-yl)acrylonitrile (150 mg, 47%) as a brown oil. LCMS ESI-MS m/z: 341 [M+H]⁺.

Step 2: 3-(4-(Pyridin-4-ylmethyl)-1-((2-(trimethylsilyl)ethoxy)methyl)-1H-imidazol-2-yl)propanenitrile. A mixture of (E)-3-(4-(pyridin-4-ylmethyl)-1-((2-(trimethylsilyl)ethoxy)methyl)-1H-imidazol-2-yl)acrylonitrile (150 mg, 0.441 mmol) and Pd/C (15 mg, 10% wt/wt) in MeOH (10 mL) was stirred at room temperature for 2 h under an atmosphere of hydrogen. The resulting mixture was filtered and the filtrate was concentrated under reduced pressure to afford crude 3-(4-(pyridin-4-ylmethyl)-1-((2-(trimethylsilyl)ethoxy)methyl)-1H-imidazol-2-yl)propanenitrile (126 mg) as a brown oil which was taken to next step without further purification. LCMS ESI-MS m/z: 343 [M+H]⁺.

Step 3: 3-(4-(Pyridin-4-ylmethyl)-1H-imidazol-2-yl)propanenitrile. A solution of 3-(4-(pyridin-4-ylmethyl)-1-((2-(trimethylsilyl)ethoxy)methyl)-1H-imidazol-2-yl)propanenitrile (126 mg, 0.368 mmol) in DCM/TFA (10 mL, v/v=2:1) was stirred at room temperature for 3 h. The reaction was then concentrated under reduced pressure and the residue was added to a solution of saturated NaHCO₃ (20 mL) and extracted into EtOAc (3×20 mL). The combined organic layers were dried over anhydrous Na₂SO₄, filtered, and concentrated under reduced pressure. The residue was purified by reverse phase HPLC to afford 3-(4-(pyridin-4-ylmethyl)-1H-imidazol-2-yl)propanenitrile (53 mg, 57%) as a brown oil. ¹H NMR (400 MHz, DMSO-d6, ppm) δ 11.67 (s, 1H), 8.43 (d, J=5.2 Hz, 2H), 7.23 (d, J=4.8 Hz, 2H), 6.75 (s, 1H), 3.82 (s, 2H), 2.94-2.79 (m, 4H). LCMS ESI-MS m/z: 213 [M+H]⁺.

Example 5, 5a, and 5b: (rac)-4-(1-(2-(2,2,2-Trifluoroethyl)-1H-imidazol-4-yl)ethyl)pyridine, (S)-4-(1-(2-(2,2,2-Trifluoroethyl)-1H-imidazol-4-yl)ethyl)pyridine, and (R)-4-(1-(2-(2,2,2-Trifluoroethyl)-1H-imidazol-4-yl)ethyl)pyridine

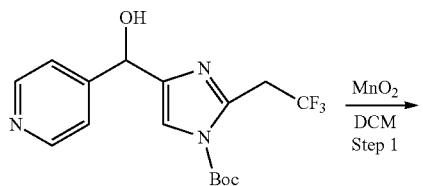

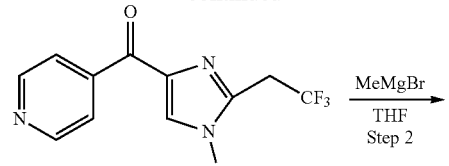

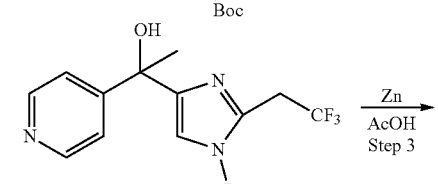

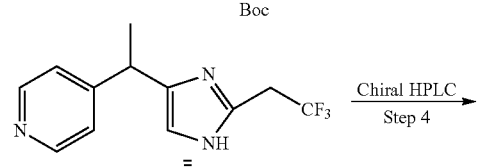

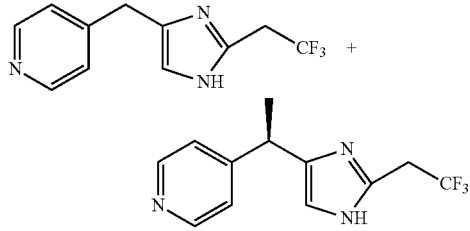

Step 1: tert-Butyl 4-isonicotinoyl-2-(2,2,2-trifluoroethyl)-1H-imidazole-1-carboxylate. A solution of tert-butyl 4-(hydroxy(pyridin-4-yl)methyl)-2-(2,2,2-trifluoroethyl)-1H-imidazole-1-carboxylate (635 mg, 1.78 mmol, Example 1, step 7), MnO₂ (1.55 g, 17.8 mmol) in DCM (30 mL) was stirred at room temperature for 16 h. The resulting mixture was filtered, and the filtrate was concentrated under reduced pressure to yield tert-butyl 4-isonicotinoyl-2-(2,2,2-trifluoroethyl)-1H-imidazole-1-carboxylate (355 mg) as a brown oil. This compound was used in the next step without further purification. LCMS ESI-MS m/z: 256 [M+H-Boc]⁺.

Step 2: tert-Butyl 4-(1-hydroxy-1-(pyridin-4-yl)ethyl)-2-(2,2,2-trifluoroethyl)-1H-imidazole-1-carboxylate. A solution of tert-butyl 4-isonicotinoyl-2-(2,2,2-trifluoroethyl)-1H-imidazole-1-carboxylate (355 mg, 1.00 mmol) in THF (20 mL) was cooled to 0° C. MeMgBr (2 mL, 2 mol, 1.0 M in THF) was added dropwise to this mixture, warmed to room temperature and stirred for 16 h. The resulting mixture was quenched with the addition of H₂O (20 mL), and the organics were extracted into EtOAc (3×50 mL). The combined organic layers were dried over anhydrous Na₂SO₄, filtered, and concentrated under reduced pressure to yield the crude tert-butyl 4-(1-hydroxy-1-(pyridin-4-yl)ethyl)-2-(2,2,2-trifluoroethyl)-1H-imidazole-1-carboxylate (420 mg) as a brown oil. This compound was used in the next step without further purification. LCMS ESI-MS m/z: 372 [M+H]⁺.

Step 3: (rac)-4-(1-(2-(2,2,2-Trifluoroethyl)-1H-imidazol-4-yl)ethyl)pyridine. A mixture of crude tert-butyl 4-(1-hydroxy-1-(pyridin-4-yl)ethyl)-2-(2,2,2-trifluoroethyl)-1H-imidazole-1-carboxylate (420 mg, 1.13 mmol) and Zn (735 mg, 11.3 mol) in AcOH (50 mL) was heated to 130° C. for 16 h. The mixture was filtered, the precipitate was rinsed with MeOH (50 mL) and the filtrate was concentrated under reduced pressure. To this residue was added saturated NaHCO₃ (50 mL) and the organics were extracted into DCM/MeOH (10:1, 3×50 mL). The combined organic layers were dried over anhydrous Na$_2$SO$_4$, filtered, and concentrated under reduced pressure. The residue was purified by prep HPLC to yield 4-(1-(2-(2,2,2-trifluoroethyl)-1H-imidazol-4-yl)ethyl)pyridine (95 mg, 37%) as a brown oil. $^1$H NMR (400 MHz, MeOH-d4, ppm) δ 8.42 (s, 2H), 7.30 (d, J=6.0 Hz, 2H), 6.96 (s, 1H), 4.14 (s, 1H), 3.58 (q, J=10.8 Hz, 2H), 1.61 (d, J=7.2 Hz, 3H). LCMS ESI-MS m/z: 256 [M+H]$^+$.

Step 4: (S)-4-(1-(2-(2,2,2-Trifluoroethyl)-1H-imidazol-4-yl)ethyl)pyridine, and (R)-4-(1-(2-(2,2,2-Trifluoroethyl)-1H-imidazol-4-yl)ethyl)pyridine. 4-(1-(2-(2,2,2-trifluoroethyl)-1H-imidazol-4-yl)ethyl)pyridine (150 mg, 0.588 mmol) was separated by chiral HPLC to afford and early eluting isomer 4-(1-(2-(2,2,2-trifluoroethyl)-1H-imidazol-4-yl)ethyl)pyridine (EXAMPLE 5a, 50.5 mg) and late eluting isomer 4-(1-(2-(2,2,2-trifluoroethyl)-1H-imidazol-4-yl)ethyl)pyridine (EXAMPLE 5b, 44.1 mg) as white solids.

Peak 1. $^1$H NMR (400 MHz, DMSO-d$_6$, ppm) δ 12.0 (s, 1H), 8.44 (d, J=6.0 Hz, 2H), 7.23 (d, J=6.0 Hz, 2H), 6.86 (s, 1H), 4.03 (q, J=7.2 Hz, 1H), 3.64 (q, J=11.2 Hz, 2H), 1.49 (d, J=7.2 Hz, 3H). LCMS ESI-MS m/z: 256 [M+H]$^+$.

Peak 2. $^1$H NMR (400 MHz, DMSO-d$_6$, ppm) δ 11.96 (s, 1H), 8.44 (d, J=6.0 Hz, 2H), 7.23 (d, J=6.0 Hz, 2H), 6.87 (s, 1H), 4.02-4.035 (m, 1H), 3.64 (q, J=11.2 Hz, 2H), 1.49 (d, J=7.2 Hz, 3H). LCMS ESI-MS m/z: 256 [M+H]$^+$.

The absolute stereochemistry was arbitrarily assigned.

Example 6: 5-((4-(Pyridin-4-ylmethyl)-1H-imidazol-2-yl)methyl)thiazole

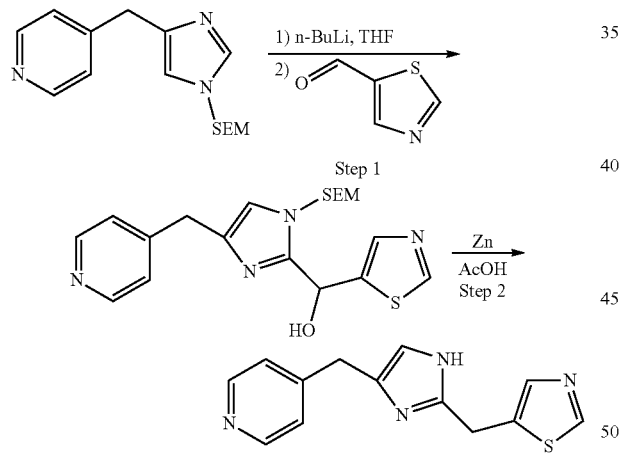

Step 1: (4-(Pyridin-4-ylmethyl)-1-((2-(trimethylsilyl)ethoxy)methyl)-1H-imidazol-2-yl)(thiazol-5-yl)methanol. To a stirred solution of 4-((1-(((2-(trimethylsilyl)ethoxy)methyl)-1H-imidazol-4-yl)methyl)pyridine (Example 3, step 3, 700 mg, 2.42 mmol) in anhydrous THF (20 mL) cooled to –70° C. under a nitrogen atmosphere, was added dropwise n-BuLi (2.42 mL, 6.04 mmol, 2.5 M solution in hexane). The resulting reaction was stirred at –70° C. for 1 h and a solution of thiazole-5-carbaldehyde (812 mg, 7.35 mmol) was added slowly over 5 min. The reaction was then allowed to warm to room temperature and stirred for 3 h. The mixture was quenched by the addition of H$_2$O (20 mL) and the organics were extracted into EtOAc (3×100 mL). The combined organic layers were dried over anhydrous Na$_2$SO$_4$, filtered, and concentrated under reduced pressure to afford crude (4-(pyridin-4-ylmethyl)-1-((2-(trimethylsilyl)ethoxy)methyl)-1H-imidazol-2-yl)(thiazol-5-yl)methanol (1.02 g) as a brown oil and used in the next step without further purification. LCMS ESI-MS m/z: 403 [M+H]$^+$.

Step 2: 5-((4-(Pyridin-4-ylmethyl)-1H-imidazol-2-yl)methyl)thiazole. A mixture of (4-(pyridin-4-ylmethyl)-1-((2-(trimethylsilyl)ethoxy)methyl)-1H-imidazol-2-yl)(thiazol-5-yl)methanol (1.02 g, crude, 2.53 mmol) and Zn (1.65 g, 25.3 mmol) in AcOH (10 mL) was stirred at 130° C. for 16 h. The resulting mixture was filtered, rinsed with MeOH (20 mL); the filtrate was concentrated under reduced pressure. The residue was added to a solution of saturated NaHCO$_3$ (50 mL), and the organics were extracted into DCM/MeOH (10:1 v/v, 3×50 mL). The combined organic layers were dried over anhydrous Na$_2$SO$_4$, filtered, and concentrated under reduced pressure. The residue was purified by reverse phase HPLC to afford 5-((4-(pyridin-4-ylmethyl)-1H-imidazol-2-yl)methyl)thiazole (51 mg, 8%) as a white solid. $^1$H NMR (400 MHz, CDCl$_3$, ppm) δ 8.63 (s, 1H), 8.41 (d, J=6.0 Hz, 2H), 7.53 (s, 1H), 7.15 (d, J=5.6 Hz, 2H), 7.14 (s, 1H), 4.24 (s, 2H), 3.89 (s, 2H). LCMS ESI-MS m/z: 257 [M+H]$^+$.

Example 7 and 7a: (S)-2,2,2-Trifluoro-1-(5-(pyridin-4-ylmethyl)-1H-imidazol-2-yl)ethan-1-ol and (R)-2,2,2-Trifluoro-1-(5-(pyridin-4-ylmethyl)-1H-imidazol-2-yl)ethan-1-ol

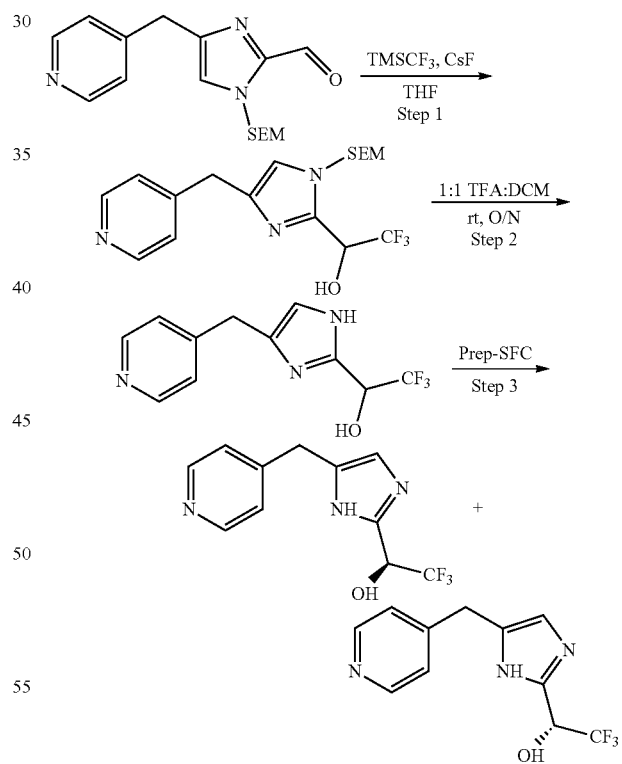

Step 1: 2,2,2-Trifluoro-1-(4-(pyridin-4-ylmethyl)-1-((2-(trimethylsilyl)ethoxy)methyl)-1H-imidazol-2-yl)ethanol. To a mixture of 4-(pyridin-4-ylmethyl)-1-((2-(trimethylsilyl)ethoxy)methyl)-1H-imidazole-2-carbaldehyde (Example 3, step 4, 15.5 g, 48.9 mmol, 1.0 eq) and THF (155 mL) was added TMSCF$_3$ (8.3 g, 58.4 mmol, 1.2 eq). The resulting mixture was cooled to 0° C. and CsF was added. The resulting solution was stirred overnight at room temperature.

The resulting mixture was filtered and the filtrate evaporated under reduced pressure and the resulting residue was purified by reverse phase column chromatography to give 2,2,2-trifluoro-1-(4-(pyridin-4-ylmethyl)-1-((2-(trimethylsilyl)ethoxy)methyl)-1H-imidazol-2-yl)ethanol as an off-white solid (15 g, 79%).

Step 2: (rac)-2,2,2-Trifluoro-1-[4-(pyridin-4-ylmethyl)-1H-imidazol-2-yl]ethanol. A mixture of 2,2,2-trifluoro-1-(4-(pyridin-4-ylmethyl)-1-((2-(trimethylsilyl)ethoxy)methyl)-1H-imidazol-2-yl)ethanol (300 mg, 0.77 mmol) in TFA (3 mL) and DCM (3 mL) was stirred overnight at room temperature under a nitrogen atmosphere. The resulting mixture was concentrated under vacuum to yield a red oil. The crude material (230 mg) was purified by prep-HPLC to afford (rac)-2,2,2-trifluoro-1-[4-(pyridin-4-ylmethyl)-1H-imidazol-2-yl]ethanol (113 mg, 57%) as a white solid. $^1$H NMR (300 MHz, DMSO-$d_6$, ppm): δ 12.19 (d, J=40.6 Hz, 1H), 8.44 (d, J=5.0 Hz, 2H), 7.28-7.14 (m, 2H), 7.08 (d, J=5.8 Hz, 1H), 6.80 (d, J=65.5 Hz, 1H), 5.23-4.94 (m, 1H), 3.33 (s, 2H). LCMS ESI-MS m/z: 258 [M+H]$^+$.

Step 3: (S)-2,2,2-Trifluoro-1-(5-(pyridin-4-ylmethyl)-1H-imidazol-2-yl)ethan-1-ol and (R)-2,2,2-Trifluoro-1-(5-(pyridin-4-ylmethyl)-1H-imidazol-2-yl)ethan-1-ol. (rac)-2,2,2-Trifluoro-1-[4-(pyridin-4-ylmethyl)-1H-imidazol-2-yl]ethanol (1 g) was purified by prep-SFC. Peak 1 was isolated as a white solid (395 mg, 29%) and Peak 2 was isolated as a white solid (391 mg, 29%).

Peak 1. $^1$H NMR (400 MHz, DMSO-$d_6$, ppm): δ 12.25 (s, 1H), 8.51-8.34 (m, 2H), 7.38-7.22 (m, 2H), 7.11 (d, J=5.9 Hz, 1H), 6.86 (s, 1H), 5.25-5.01 (m, 1H), 3.86 (s, 2H). LCMS ESI-MS m/z: 258 [M+H]$^+$.

Peak 2. $^1$H NMR (400 MHz, DMSO-$d_6$, ppm): δ 12.24 (s, 1H), 8.48-8.42 (m, 2H), 7.28-7.22 (m, 2H), 7.11 (d, J=5.9 Hz, 1H), 6.86 (s, 1H), 5.18-5.06 (m, 1H), 3.86 (s, 2H). LCMS ESI-MS m/z: 258 [M+H]$^+$.

The absolute stereochemistry was arbitrarily assigned.

Example 8: 4-((5-(2,2,2-Trifluoroethyl)-1H-1,2,4-triazol-3-yl)methyl)pyridine

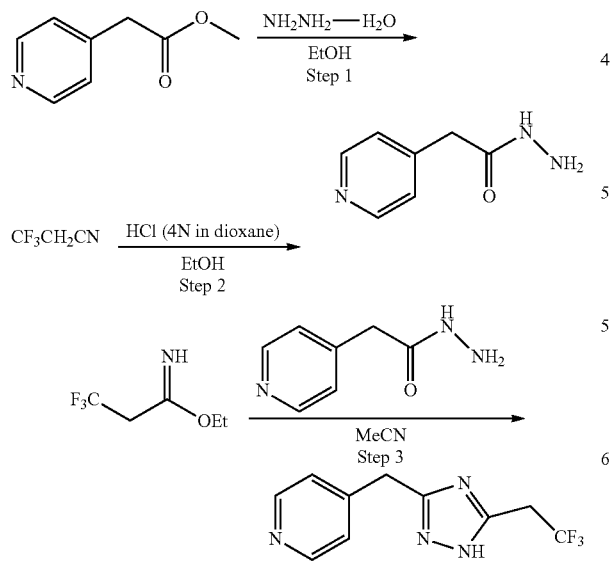

Step 1: 2-(Pyridin-4-yl)acetohydrazide. A solution of methyl-2-(pyridin-4-yl)acetate (206 mg, 1.36 mmol) and hydrazine monohydrate (102 mg, 2.04 mmol) in EtOH (4 mL) was stirred at 75° C. for 16 h. The resulting mixture was concentrated under reduced pressure. The residue was purified by reverse phase HPLC to afford 2-(pyridin-4-yl)acetohydrazide (120 mg, 58%) as a colorless oil and was used in the next step without further purification. LCMS ESI-MS m/z: 152 [M+H]$^+$.

Step 2: Ethyl-3,3,3-trifluoropropanimidate. HCl (4 N in dioxane, 2.5 mL, 10 mmol) was added slowly to a solution of 3,3,3-trifluoropropanenitrile (404 mg, 3.7 mmol) in EtOH at 0° C. and it was stirred at room temperature for 16 h. The resulting mixture was concentrated under reduced pressure to afford ethyl-3,3,3-trifluoropropanimidate as a white solid and was used in the next step without further purification. LCMS ESI-MS m/z: 156 [M+H]$^+$.

Step 3: 4-((5-(2,2,2-Trifluoroethyl)-1H-1,2,4-triazol-3-yl)methyl)pyridine. Ethyl-3,3,3-trifluoropropanimidate (40 mg, 0.26 mmol) was added to a solution of 2-(pyridin-4-yl)acetohydrazide (39 mg, 0.26 mmol) in MeCN (1.5 ml) and it was stirred at room temperature for 10 min and at 50° C. for 20 min. Then it was stirred at 105° C. for 1 h. The resulting mixture was concentrated under reduced pressure. The residue was purified by reverse phase HPLC to afford 4-((5-(2,2,2-trifluoroethyl)-1H-1,2,4-triazol-3-yl)methyl)pyridine (2.4 mg, 4%) as a colorless oil. $^1$H NMR (400 MHz, MeCN-d3, ppm) δ 8.50 (d, J=5.1 Hz, 2H), 7.28 (d, J=5.0 Hz, 2H), 4.13 (s, 2H), 3.62 (q, J=10.8 Hz, 2H). LCMS ESI-MS m/z: 243 [M+H]$^+$.

Example 9: 2-(Pyridin-4-ylmethyl)-4-(2,2,2-trifluoroethyl)thiazole

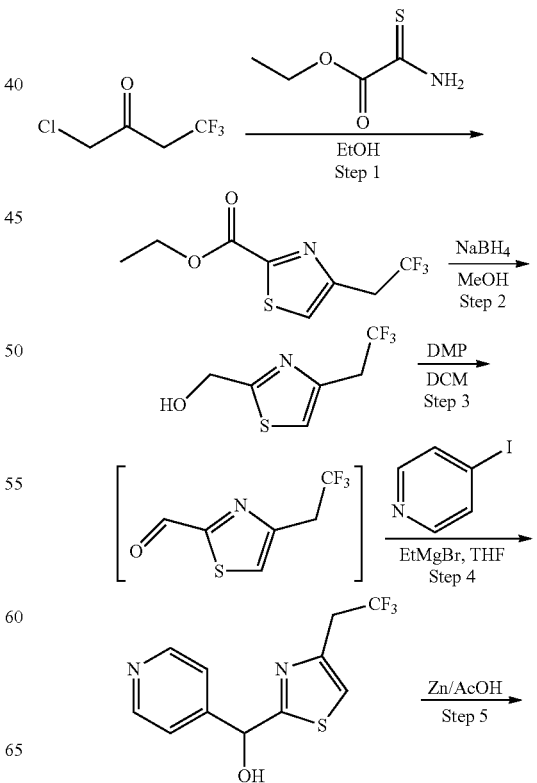

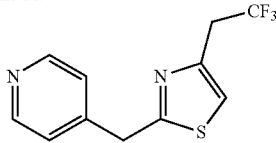

Step 1: Ethyl 4-(2,2,2-trifluoroethyl)-thiazole-2-carboxylate. A vial was charged with 1-chloro-4,4,4-trifluorobutan-2-one (1.81 mL, 0.36 mmol) and EtOH (2 mL). Ethyl carbamothioylformate (57.7 mg, 0.43 mmol) was then added and the resulting reaction mixture was heated to 80° C. After 16 h, the reaction mixture was concentrated under reduced pressure to provide ethyl 4-(2,2,2-trifluoroethyl)thiazole-2-carboxylate as a colorless solid (43 mg) and the compound was used in the next step without further purification. LCMS ESI-MS m/z: 240 [M+H]$^+$.

Step 2: (4-(2,2,2-Trifluoroethyl)-thiazol-2-yl)methanol. A vial was charged with ethyl 4-(2,2,2-trifluoroethyl)-1,3-thiazole-2-carboxylate (10.4 mL, 1.04 mmol) and MeOH (2 mL). Sodium borohydride (118 mg, 3.11 mmol) was added to the reaction mixture and stirred for 1 h. The reaction was quenched with the addition of water (10 mL) and the aqueous layer was extracted with DCM (3×20 mL). The combined organic layers were washed with brine (30 mL), dried over MgSO$_4$, filtered, and concentrated under reduced pressure to provide (4-(2,2,2-trifluoroethyl)thiazol-2-yl)methanol as a light yellow solid (200 mg) which was taken to next step without further purification. LCMS: ESI-MS m/z: 198 [M+H]$^+$.

Step 3: 4-(2,2,2-Trifluoroethyl)-thiazole-2-carbaldehyde. A vial was charged with (4-(2,2,2-trifluoroethyl)-1,3-thiazol-2-yl)methanol (10.4 mL, 1.04 mmol) and was dissolved in DCM (10 mL). 1,1-bis(acetyloxy)-3-oxo-3H-1λ$^5$,2-benziodaoxol-1-yl acetate (617 mg, 1.46 mmol) was then added to the reaction mixture. After 12 h, reaction mixture was diluted with DCM (20 mL), washed with water (1×10 mL), brine (1×10 mL), dried over MgSO$_4$ and filtered. The filtrate was concentrated under reduced pressure to give a crude 4-(2,2,2-trifluoroethyl)thiazole-2-carbaldehyde as a light-yellow oil (82 mg), which was taken to next step without further purification.

Step 4: Pyridin-4-yl(4-(2,2,2-trifluoroethyl)-thiazol-2-yl)methanol. A vial was charged with 4-iodopyridine (1.51 mL, 0.302 mmol) and was dissolved in THF (1.4 mL). The solution was cooled to 0° C. and ethyl magnesium bromide (0.12 mL, 0.363 mmol) was added dropwise over 30 seconds. 4-(2,2,2-trifluoroethyl-thiazole-2-carbaldehyde (Crude from Step 3; 59 mg, 0.3 mmol) was added to the reaction mixture and the resulting mixture was stirred for 10 minutes at 0° C. The reaction was then warmed to room temperature and stirred. The reaction mixture was quenched with the addition of water (20 mL) after 30 minutes and the organics were extracted into EtOAc (3×30 mL). The combined organic layers were washed with brine (1×30 mL) and dried over MgSO$_4$, filtered, and concentrated under reduced pressure. The crude mixture was purified by normal phase chromatography to provide pyridin-4-yl(4-(2,2,2-trifluoroethyl)-thiazol-2-yl)methanol (22 mg, 27%). $^1$H NMR (400 MHz, CDCl$_3$, ppm) δ 8.68-8.44 (m, 2H), 7.51-7.33 (m, 2H), 7.17 (s, 1H), 5.97 (s, 1H), 3.84 (q, J=10.1 Hz, 2H). LCMS ESI-MS m/z: 275 [M+H]$^+$.

Step 5: 2-(Pyridin-4-ylmethyl)-4-(2,2,2-trifluoroethyl)thiazole. A vial was charged with (pyridin-4-yl)(2-(2,2,2-trifluoroethyl)-1,3-thiazol-4-yl)methanol (1.42 mL, 0.142 mmol) and was dissolved in acetic acid (1.4 mL). Zinc (52.4 mg, 0.802 mmol) was then added and the reaction was heated to 80° C. Another portion of zinc (52.4 mg, 0.802 mmol) was added after 18 h. After 2 h, another portion of zinc (52.4 mg, 0.802 mmol) was added and stirred at 80° C. for 2 more hours. The reaction was cooled to room temperature and filtered over celite and washed with EtOAc (10 mL) and MeOH (10 mL). The filtrate was diluted with EtOAc (30 mL) and quenched with aqueous solution of saturated NaHCO$_3$ (40 mL). The aqueous layer was extracted with EtOAc (3×30 mL). The combined organic layers were washed with brine (30 mL), dried over MgSO$_4$. The reaction mixture was concentrated and purified by normal phase chromatography to afford 2-(pyridin-4-ylmethyl)-4-(2,2,2-trifluoroethyl)thiazole as a clear yellow oil (12 mg, 56%). $^1$H NMR (400 MHz, CDCl$_3$, ppm) δ 8.60 (d, J=4.9 Hz, 2H), 7.28 (t, J=3.8 Hz, 2H), 7.15 (s, 1H), 4.35 (s, 2H), 3.63 (q, J=10.5 Hz, 2H). LCMS ESI-MS m/z: 259 [M+H]$^+$.

Example 10: 4-(Pyridin-4-ylmethyl)-2-(2,2,2-trifluoroethyl)thiazole

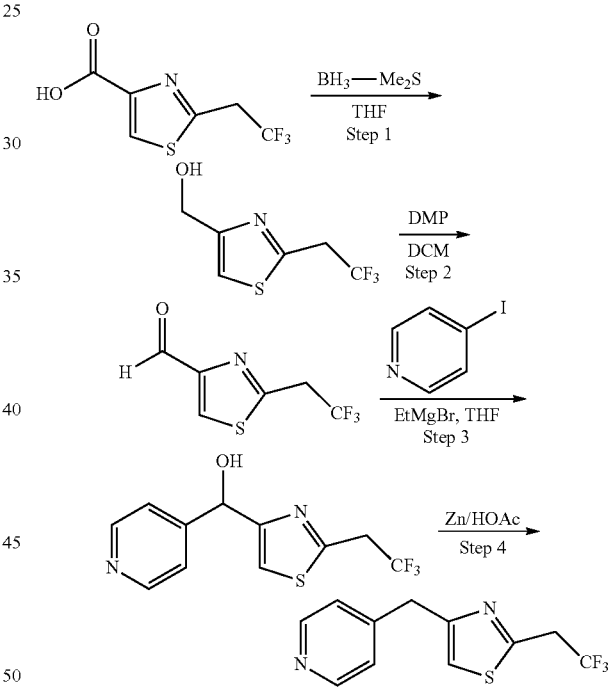

Step 1: (2-(2,2,2-Trifluoroethyl)thiazol-4-yl)methanol. An oven dried vial was charged with 2-(2,2,2-trifluoroethyl)-1,3-thiazole-4-carboxylic acid (435 mg, 2.06 mmol) and was suspended in THF (4.7 mL) under argon. Borane dimethyl sulfide (586 μL, 6.18 mmol) was then added dropwise over 2 min. After it was stirred at room temperature for 16 h, the reaction mixture was cooled to 0° C. and quenched with the slow addition of 1 M HCl solution. After the bubbling ceased, the reaction mixture was extracted into EtOAc (3×30 mL). The combined organic layers were washed with brine (30 mL), dried over MgSO$_4$, filtered, and concentrated under reduced pressure. The residue was purified by chromatography to afford pyridin-4-yl(2-(2,2,2-trifluoroethyl)thiazol-4-yl)methanol (209 mg, 51%) as a clear yellow oil. LCMS ESI-MS m/z: 198 [M+H]$^+$.

Step 2: 2-(2,2,2-Trifluoroethyl)thiazole-4-carbaldehyde. A vial was charged with (2-(2,2,2-trifluoroethyl)-1,3-thiazol-4-yl)methanol (202 mg, 1.02 mmol) and was dissolved in DCM (4 mL). The reaction mixture was rapidly stirred under argon and Dess-Martin periodinane (739 mg, 1.74 mmol) was added. After it was stirred at room temperature for 2 h, the reaction mixture was quenched with the addition of water (20 mL) and diluted with EtOAc (30 mL). The layers were separated and the aqueous layer was extracted into EtOAc (3×20 mL). The combined organic layers were washed with brine (30 mL) and dried over anhydrous MgSO$_4$, filtered, and concentrated under reduced pressure. The residue was purified by silica gel chromatography to afford 2-(2,2,2-trifluoroethyl)thiazole-4-carbaldehyde (113 mg, 56%) as a colorless oil. LCMS ESI-MS m/z: 196 [M+H]$^+$.

Step 3: Pyridin-4-yl(2-(2,2,2-trifluoroethyl)thiazol-4-yl)methanol. A flask was charged with 4-iodopyridine (1.28 mL, 256 μmol) and was dissolved in THF (1.4 mL). The solution was cooled to 0° C. and ethylmagnesium bromide (0.133 mL, 0.44 mmol) was added dropwise over 30 seconds. After the resulting mixture was stirred at room temperature for 30 min, 2-(2,2,2-trifluoroethyl)thiazole-4-carbaldehyde in THF (1 mL) was added slowly and it was stirred at room temperature for 1 h. The reaction mixture was quenched with the addition of water (20 mL) and diluted with EtOAc (30 mL). The layers were separated and the aqueous layer was extracted with EtOAc (3×20 mL). The combined organic layers were washed with brine (30 mL), dried over anhydrous MgSO$_4$, filtered, and concentrated under reduced pressure. The residue was purified by silica gel chromatography to afford pyridin-4-yl(2-(2,2,2-trifluoroethyl)thiazol-4-yl)methanol (54 mg, 59%) as an clear oil. $^1$H NMR (400 MHz, CDCl$_3$, ppm) δ 8.68-8.44 (m, 2H), 7.51-7.33 (m, 2H), 7.17 (s, 1H), 5.97 (s, 1H), 3.84 (q, J=10.1 Hz, 2H). LCMS ESI-MS m/z: 275 [M+H]$^+$.

Step 4: 4-(Pyridin-4-ylmethyl)-2-(2,2,2-trifluoroethyl)thiazole. A vial was charged with (pyridin-4-yl)(2-(2,2,2-trifluoroethyl)-1,3-thiazol-4-yl)methanol (39 mg, 0.142 mmol) and acetic acid (1.4 mL). Zinc (93 mg, 1.42 mmol) was then added and the reaction was heated to 80° C. for 18 h. Additional zinc (93 mg, 1.42 mmol) was added and the reaction stirred at 80° C. for 2 h. The reaction mixture was cooled to room temperature, filtered over celite, and rinsed with EtOAc (10 mL) and MeOH (10 mL). The filtrate was diluted with EtOAc (30 mL) and neutralized with sat. aq. NaHCO$_3$ solution (40 mL) and checked with pH paper to ~pH 7. The aqueous layer was extracted with EtOAc (3×30 mL). The combined organic layers were washed with brine (30 mL), dried over anhydrous MgSO$_4$, filtered, and concentrated under reduced pressure. The residue was purified by silica gel chromatography to afford 4-(pyridin-4-ylmethyl)-2-(2,2,2-trifluoroethyl)thiazole (18 mg, 49%) as a clear yellow oil. $^1$H NMR (400 MHz, CDCl$_3$, ppm) δ 8.72-8.40 (m, 2H), 7.21 (d, J=5.4 Hz, 2H), 6.97 (s, 1H), 4.15 (s, 2H), 3.84 (q, J=10.2 Hz, 2H). LCMS ESI-MS m/z: 259 [M+H]$^+$.

Example 11: (rac)-4-(1-(5-(2,2,2-Trifluoroethyl)-1H-pyrrol-2-yl)ethyl)pyridine

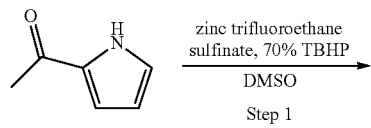

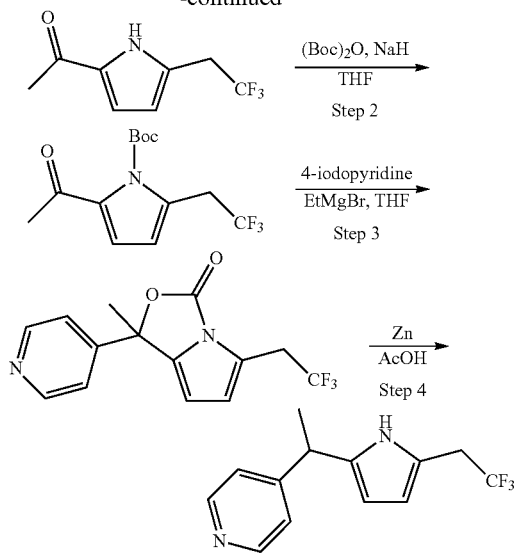

Step 1: 1-(5-(2,2,2-Trifluoroethyl)-1H-pyrrol-2-yl)ethan-1-one. To a stirred solution of 1-(1H-pyrrol-2-yl)ethan-1-one (100 mg, 0.916 mmol) and DMSO (2 mL) was added zinc trifluoroethane sulfinate (461 mg, 0.916 mmol), then tert-butyl-hydroperoxide (389 mg, 3.02 mmol, 70% aq). The reaction mixture was heated to 60° C. in a 4 mL reaction vial. After 2 h, the reaction mixture was purified directly by silica gel chromatography to yield 1-(5-(2,2,2-trifluoroethyl)-1H-pyrrol-2-yl)ethan-1-one (54 mg) as a white solid and was used in the next step without further purification. LCMS ESI-MS m/z: 192 [M+H]$^+$.

Step 2: tert-Butyl 2-acetyl-5-(2,2,2-trifluoroethyl)-1H-pyrrole-1-carboxylate. To a solution of 1-(5-(2,2,2-trifluoroethyl)-1H-pyrrol-2-yl)ethan-1-one (54 mg, 0.282 mmol) and THF (5 mL) was added 60% NaH (25 mg, 0.625 mmol) at 0° C. under an atmosphere of nitrogen. After 30 min, di-tert-butyl dicarbonate (93 mg, 0.424 mmol) was added. After 3 h, the reaction was quenched with the addition of water and extracted with EtOAc. The organic layer was washed with water and brine, dried over Na$_2$SO$_4$, filtered, and concentrated under reduced pressure. The crude product was purified by silica gel chromatography to yield tert-butyl 2-acetyl-5-(2,2,2-trifluoroethyl)-1H-pyrrole-1-carboxylate (37 mg, 45%). LCMS ESI-MS m/z: 236 [M-tBu]$^+$.

Step 3: 1-Methyl-1-(pyridine-4-yl)-5-(2,2,2-trifluoroethyl)-1H, 3H-pyrrol[1,2-c]oxazol-3-one. To a 5 mL round bottom flask under an atmosphere of nitrogen, was added 4-iodo-pyridine (6.35 mL, 1.27 mmol) and THF (3 mL). The solution was cooled to 0° C. and a solution of ethylmagnesium bromide (0.423 mL, 1.27 mmol) was added dropwise over 30 sec. The reaction was allowed to warm to room temperature and stirred for 30 min. tert-Butyl-acetyl-1H-pyrrole-1-carboxylate (200 mg, 0.956 mmol) in THF (2 mL) was added at 0° C. and the reaction was warmed to room temperature. After 1 h, the reaction was quenched with the addition of water and solid NH$_4$Cl was added to saturate the aqueous layer. The aqueous layer was separated, and the organic layer was dried over Na$_2$SO$_4$. The organic layer was filtered and concentrated under reduced pressure to yield the crude product. The crude product was purified by silica chromatography to yield 1-methyl-1-(pyridine-4-yl)-5-(2,2,2-trifluoroethyl)-1H, 3H-pyrrol[1,2-c]oxazol-3-one (23.7 mg, 69%) as a light yellow oil. LCMS ESI-MS m/z: 297 [M+H]$^+$.

Step 4: (rac)-4-(1-(5-(2,2,2-Trifluoroethyl)-1H-pyrrol-2-yl)ethyl)pyridine. To a solution of 1-methyl-1-(pyridine-4-yl)-5-(2,2,2-trifluoroethyl)-1H, 3H-pyrrol[1,2-c]oxazol-3-one (23.7 mg, 0.088 mmol) and acetic acid (1 mL) was added zinc powder (57.3 mg, 0.877 mmol), and the resulting mixture was heated in a 4 mL reaction vial at 125° C. for 2 h. The reaction mixture was filtered through celite and concentrated under reduced pressure to yield (rac)-4-(1-(5-(2,2,2-trifluoroethyl)-1H-pyrrol-2-yl)ethyl)pyridine (22 mg, 99%) as a yellow oil. $^1$H NMR (400 MHz, CDCl$_3$, ppm) δ 8.38 (br s, 2H), 7.15 (d, J=8.0 Hz, 2H), 6.11-6.08 (m, 2H), 4.14 (q, J=8.0 Hz, 1H), 3.26 (q, J=12.0 Hz, 2H), 1.59 (d, J=8.0 Hz, 3H). LCMS ESI-MS m/z: 255 [M+H]$^+$.

Example 12: 2,2,2-Trifluoro-1-(5-(pyridin-4-ylmethyl)-1H-imidazol-2-yl)ethan-1-one hydrochloride

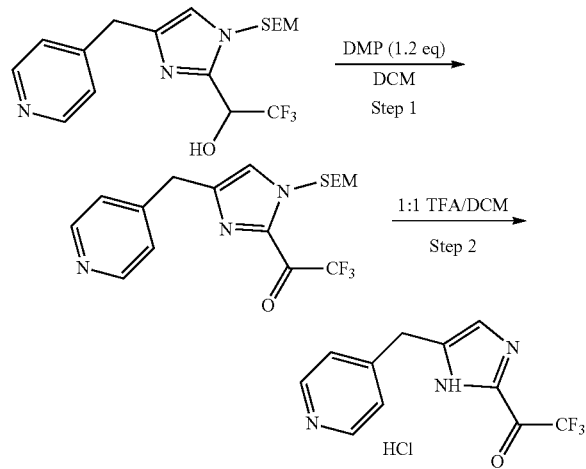

Step 1: 2,2,2-Trifluoro-1-(4-(pyridin-4-ylmethyl)-1-((2-(trimethylsilyl)ethoxy)methyl)-1H-imidazol-2-yl)ethan-1-one. A mixture of 2,2,2-trifluoro-1-(4-(pyridin-4-ylmethyl)-1-((2-(trimethylsilyl)ethoxy)methyl)-1H-imidazol-2-yl)ethanol (Example 7, step 1, 300 mg, 0.77 mmol) and DMP (394 mg, 0.93 mmol) in DCM (6 mL) was stirred for 2 h at room temperature under a nitrogen atmosphere. The reaction was quenched with sat aq. NaHCO$_3$ (10 mL) and sat. aq. Na$_2$S$_2$O$_3$ (10 mL) at room temperature. The resulting mixture was extracted with DCM (2×15 mL). The combined organic layers were washed with brine (2×10 mL), dried over anhydrous Na$_2$SO$_4$, filtered, and concentrated under reduced pressure to yield 2,2,2-trifluoro-1-(4-(pyridin-4-ylmethyl)-1-((2-(trimethylsilyl)ethoxy)methyl)-1H-imidazol-2-yl)ethan-1-one as a black oil (290 mg, 97%). LCMS ESI-MS m/z: 386 [M+H]$^+$.

Step 2: 2,2,2-Trifluoro-1-(5-(pyridin-4-ylmethyl)-1H-imidazol-2-yl)ethan-1-one hydrochloride. A mixture of 2,2,2-trifluoro-1-(4-(pyridin-4-ylmethyl)-1-((2-(trimethylsilyl)ethoxy)methyl)-1H-imidazol-2-yl)ethan-1-one (290 mg, 0.75 mmol), DCM (2.9 mL) and TFA (2.9 mL) was stirred overnight at room temperature under a nitrogen atmosphere. The resulting solution was concentrated under reduced pressure to yield yellow oil. The residue was dissolved in 4 M HCl in dioxane (10 mL) and then stirred overnight at room temperature. The resulting mixture was concentrated under reduced pressure to yield yellow oil. The crude product (200 mg) was purified via prep-HPLC to provide the crude product as a yellow solid (105 mg). The crude product was purified again via prep-HPLC. The combined product fractions (500 mL) were treated with conc. HCl (5 mL) and concentrated under reduced pressure to yield and purified by prep-HPLC to remove NH$_4$Cl salt to afford 2,2,2-trifluoro-1-(5-(pyridin-4-ylmethyl)-1H-imidazol-2-yl)ethan-1-one hydrochloride as a yellow solid (31 mg, 14%). $^1$H NMR (400 MHz, D$_2$O, ppm): δ 8.75-8.58 (m, 2H), 7.84 (d, J=6.3 Hz, 2H), 7.43 (s, 1H), 4.42 (s, 2H). LCMS ESI-MS m/z: 271 [M+H]$^+$.

Example 13: (E/Z)-2,2,2-Trifluoro-1-(5-(pyridin-4-ylmethyl)-1H-imidazol-2-yl)ethan-1-one oxime

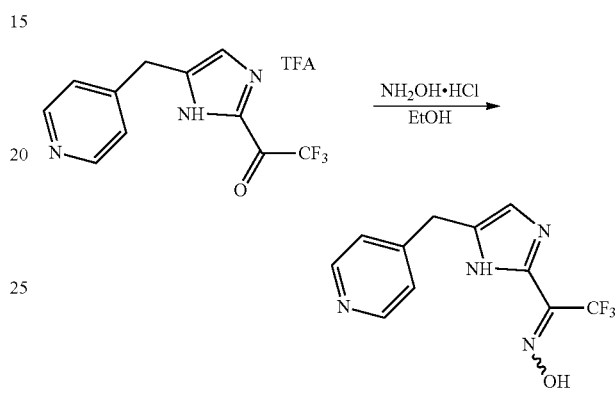

To a stirred solution of 2,2,2-trifluoro-1-(5-(pyridin-4-ylmethyl)-1H-imidazol-2-yl)ethan-1-one 2,2,2-trifluoroacetate (Example 12, 110 mg, 0.298 mmol) in EtOH (2 mL) was added NH$_2$OH·HCl (41 mg, 0.596 mmol) at room temperature under a nitrogen atmosphere. The resulting mixture was stirred for 3 h at 80° C. under a nitrogen atmosphere. The resulting mixture was basified to pH 8 with sat. aq. NaHCO$_3$. The crude product (100 mg) was purified by prep-HPLC to afford (E/Z)-2,2,2-trifluoro-1-(5-(pyridin-4-ylmethyl)-1H-imidazol-2-yl)ethan-1-one oxime (16 mg, 14%) as a white solid. $^1$H NMR (400 MHz, DMSO-d$_6$, ppm): δ 12.72 (s, 2H), 8.49-8.43 (m, 2H), 7.29-7.23 (m, 2H), 7.08 (s, 1H), 3.98 (s, 2H). LCMS ESI-MS m/z: 271 [M+H]$^+$.

Example 14: 4-((5-Methyl-2-(2,2,2-trifluoroethyl)-1H-imidazol-4-yl)methyl)pyridine

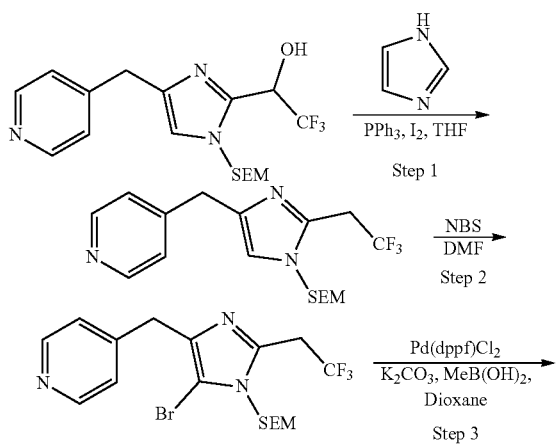

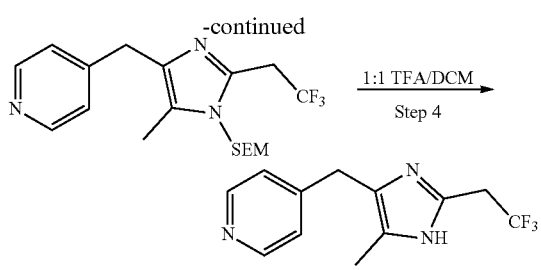

Step 1: 4-((2-(2,2,2-Trifluoroethyl)-1-((2-(trimethylsilyl)ethoxy)methyl)-1H-imidazol-4-yl)methyl)pyridine. 2,2,2-Trifluoro-1-(4-(pyridin-4-ylmethyl)-1-((2-(trimethylsilyl)ethoxy)methyl)-1H-imidazol-2-yl)ethan-1-ol (Example 7, step 1, 1.2 g), triphenylphosphine (0.97 g, 3.7 mmol), imidazole (0.25 g, 3.7 mmol), iodine (0.47 g, 1.8 mmol) and tetrahydrofuran (12 mL) were combined in a 20 mL vial at 25° C. The resulting mixture was stirred for 1 h at 70° C. under a nitrogen atmosphere. The resulting mixture was quenched with sat. aq. Na₂SO₃ at 0-10° C. and extracted with EtOAc (3×10 mL). The combined organic phase was washed with brine (1×20 mL), dried over anhydrous Na₂SO₄, filtered, and concentrated under reduced pressure. The residue was purified by reverse phase column chromatography to afford 4-((2-(2,2,2-trifluoroethyl)-1-((2-(trimethylsilyl)ethoxy)methyl)-1H-imidazol-4-yl)methyl)pyridine (0.56 g) as brown oil. LCMS ESI-MS m/z: 372 [M+H]⁺.

Step 2: 4-((5-Bromo-2-(2,2,2-trifluoroethyl)-1-((2-(trimethylsilyl)ethoxy)methyl)-1H-imidazol-4-yl)methyl)pyridine. A mixture of 4-((2-(2,2,2-trifluoroethyl)-1-((2-(trimethylsilyl)ethoxy)methyl)-1H-imidazol-4-yl)methyl) pyridine (520 mg, 1.4 mmol) and NBS (274 mg, 1.54 mmol) in DMF (6 mL) was stirred for 3 h at room temperature under nitrogen atmosphere. The reaction was quenched with sat. aq. Na₂SO₃ at 0-5° C. The resulting mixture was extracted with EtOAc (2×10 mL), and the combined organic layers were washed with brine (1×20 mL), dried over anhydrous Na₂SO₄, filtered, and concentrated under reduced pressure to provide a brown oil (300 mg). The crude material was purified by reverse phase column chromatography to afford 4-((5-bromo-2-(2,2,2-trifluoroethyl)-1-((2-(trimethylsilyl)ethoxy)methyl)-1H-imidazol-4-yl)methyl)pyridine (150 mg) as a brown solid. LCMS ESI-MS m/z: 450/452 [M+H]⁺.

Step 3: 4-((5-Methyl-2-(2,2,2-trifluoroethyl)-1-((2-(trimethylsilyl)ethoxy)methyl)-1H-imidazol-4-yl)methyl)pyridine. To a solution of 4-((5-bromo-2-(2,2,2-trifluoroethyl)-1-((2-(trimethylsilyl)ethoxy)methyl)-1H-imidazol-4-yl)methyl)pyridine (120 mg, 0.27 mmol) and methylboronic acid (24 mg, 0.40 mmol) in 1,4-dioxane (5 mL) were added K₂CO₃ (110 mg, 0.80 mmol) and Pd(dppf)Cl₂ (4 mg, 0.005 mmol). The mixture was bubbled with N₂ for 1 min. The resulting mixture was stirred overnight at 100° C. under nitrogen atmosphere. The reaction was cooled to room temperature, then quenched with cooled water at 0-5° C. The resulting mixture was extracted with EtOAc (2×5 mL). The combined organic layers were washed with brine (1×10 mL), dried over anhydrous Na₂SO₄. After filtration, the filtrate was concentrated under reduced pressure. The crude product 4-((5-methyl-2-(2,2,2-trifluoroethyl)-1-((2-(trimethylsilyl)ethoxy)methyl)-1H-imidazol-4-yl)methyl)pyridine (100 mg, brown oil) was used in the next step directly without further purification. LCMS ESI-MS m/z: 386 [M+H]⁺.

Step 4: 4-((5-Methyl-2-(2,2,2-trifluoroethyl)-1H-imidazol-4-yl)methyl)pyridine. To a stirred mixture of 4-((5-methyl-2-(2,2,2-trifluoroethyl)-1-((2-(trimethylsilyl)ethoxy)methyl)-1H-imidazol-4-yl)methyl)pyridine (100 mg, 0.21 mmol, ~81% purity) in DCM (1 mL) was added TFA (1 mL) dropwise at room temperature under nitrogen atmosphere. The resulting mixture was stirred overnight at 45° C. under nitrogen atmosphere. The resulting mixture was concentrated under reduced pressure and the residue was dissolved in EtOAc (5 mL) and H₂O (5 mL), then basified to pH 8 with sat. aq. NaHCO₃. The solution was extracted with EtOAc (3×5 mL). The combined organic layers were washed with brine (1×10 mL), dried over anhydrous Na₂SO₄, filtered and the filtrate was concentrated under reduced pressure to yield a brown oil (80 mg). The crude product was purified via prep-HPLC to afford 4-((5-methyl-2-(2,2,2-trifluoroethyl)-1H-imidazol-4-yl)methyl)pyridine (12 mg, 22%) as a white solid. ¹H NMR (400 MHz, DMSO-d₆, ppm): δ 11.78 (s, 1H), 8.49-8.38 (m, 2H), 7.21-7.12 (m, 2H), 3.92-3.70 (d, 2H), 3.58 (m, J=11.1, 3.2 Hz, 2H), 2.20-1.97 (d, 3H). LCMS ESI-MS m/z: 256 [M+H]⁺.

Example 15 and 15a: (S)-2,2,2-Trifluoro-1-(4-(pyridin-4-ylmethyl)-1H-imidazol-2-yl)ethan-1-amine and (R)-2,2,2-Trifluoro-1-(4-(pyridin-4-ylmethyl)-1H-imidazol-2-yl)ethan-1-amine

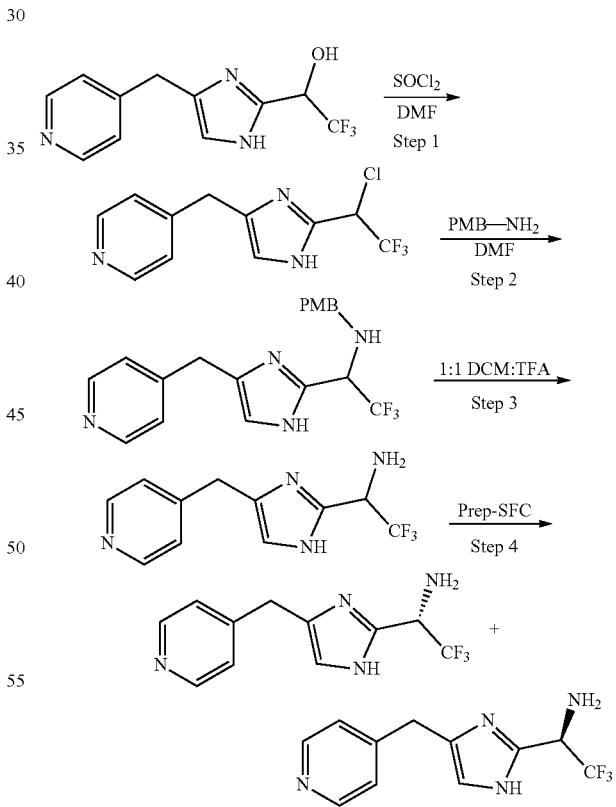

Step 1: (rac)-4-((2-(1-Chloro-2,2,2-trifluoroethyl)-1H-imidazol-4-yl)methyl)pyridine. A solution of SOCl₂ (3 mL) in DMF (8.5 mg, 0.117 mmol) was cooled to 0° C. (rac)-2,2,2-trifluoro-1-(4-(pyridin-4-ylmethyl)-1H-imidazol-2-yl)ethan-1-ol (Example 7, step 2, 300 mg, 1.2 mmol) was added in portions at 0° C. and then stirred overnight at room temperature. The resulting mixture was concentrated under reduced pressure to afford (rac)-4-([2-(1-chloro-2,2,2-trifluoroethyl)-1H-imidazol-4-yl]methyl)pyridine (300 mg) as a yellow solid. LCMS ESI-MS m/z: 276 [M+H]+.

Step 2: (rac)-2,2,2-Trifluoro-N-(4-methoxybenzyl)-1-(4-(pyridin-4-ylmethyl)-1H-imidazol-2-yl)ethan-1-amine. To a stirred solution of (rac)-4-([2-(1-chloro-2,2,2-trifluoroethyl)-1H-imidazol-4-yl]methyl)pyridine (300 mg, 1.1 mmol) in DMF (3 mL) was added 4-methoxy-benzene methanamine (1.5 g, 10.9 mmol) dropwise at 0° C. under a nitrogen atmosphere. The resulting mixture was stirred for 3 h at room temperature under a nitrogen atmosphere. The resulting mixture was concentrated under reduced pressure to yield a brown solid. The crude product (500 mg) was purified by reverse phase column chromatography to afford (rac)-2,2,2-trifluoro-N-(4-methoxybenzyl)-1-(4-(pyridin-4-ylmethyl)-1H-imidazol-2-yl)ethan-1-amine (200 mg, 49%) as a yellow solid. LCMS ESI-MS m/z: 377 [M+H]+.

Step 3: (rac)-2,2,2-Trifluoro-1-(4-(pyridin-4-ylmethyl)-1H-imidazol-2-yl)ethan-1-amine. To a stirred solution of (rac)-2,2,2-trifluoro-N-(4-methoxybenzyl)-1-(4-(pyridin-4-ylmethyl)-1H-imidazol-2-yl)ethan-1-amine (180 mg, 0.478 mmol) in DCM (2 mL) was added TFA (2 mL) at room temperature under a nitrogen atmosphere and stirred overnight. The resulting mixture was concentrated under reduced pressure to yield a yellow solid. The crude product (200 mg) was purified by prep-HPLC to afford (rac)-2,2,2-trifluoro-1-(4-(pyridin-4-ylmethyl)-1H-imidazol-2-yl)ethan-1-amine (80 mg, 65%) as yellow oil. LCMS ESI-MS m/z: 257 [M+H]+.

Step 4: (S)-2,2,2-trifluoro-1-(4-(pyridin-4-ylmethyl)-1H-imidazol-2-yl)ethan-1-amine and (R)-2,2,2-trifluoro-1-(4-(pyridin-4-ylmethyl)-1H-imidazol-2-yl)ethan-1-amine. (rac)-2,2,2-trifluoro-1-(4-(pyridin-4-ylmethyl)-1H-imidazol-2-yl)ethan-1-amine (100 mg) was purified by prep-SFC. Peak 1 was isolated as a white solid (22 mg, 28%) and Peak 2 was isolated as a white solid (17 mg, 21%).).

Peak 1. 1H NMR (400 MHz, DMSO-d6, ppm): δ 8.48-8.42 (m, 2H), 7.27-7.21 (m, 2H), 6.85 (s, 1H), 4.55-4.45 (m, 1H), 3.86 (s, 2H); LCMS ESI-MS m/z: 257 [M+H]+.

Peak 2. 1H NMR (400 MHz, DMSO-d6, ppm): δ 8.48-8.42 (m, 2H), 7.27-7.21 (m, 2H), 6.84 (s, 1H), 4.52-4.46 (m, 1H); LCMS ESI-MS m/z: 257 [M+H]+.

The absolute stereochemistry was assigned arbitrarily.

Example 16 and 16a: (S)-2,2,2-Trifluoro-N-methyl-1-(5-(pyridin-4-ylmethyl)-1H-imidazol-2-yl)ethan-1-amine and (R)-2,2,2-Trifluoro-N-methyl-1-(5-(pyridin-4-ylmethyl)-1H-imidazol-2-yl)ethan-1-amine

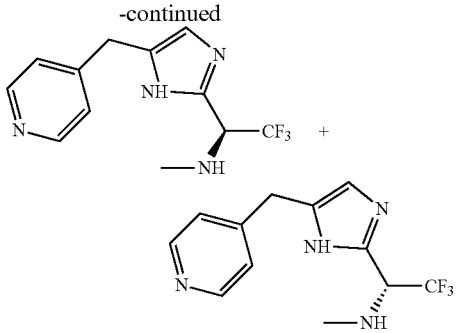

Step 1: (rac)-2,2,2-Trifluoro-N-methyl-1-(5-(pyridin-4-ylmethyl)-1H-imidazol-2-yl)ethan-1-amine. To a stirred solution 4-((2-(1-chloro-2,2,2-trifluoroethyl)-1H-imidazol-5-yl)methyl)pyridine (Example 15, step 1, 300 mg, 1.09 mmol) in EtOH (3 mL) was added CH3NH2 (1 mL, 30% in EtOH) dropwise at 0° C. under a nitrogen atmosphere. The resulting mixture was stirred for 2 h at room temperature and concentrated under reduced pressure to yield a brown oil. The crude product (100 mg) was purified by prep-HPLC to afford 2,2,2-trifluoro-N-methyl-1-(5-(pyridin-4-ylmethyl)-1H-imidazol-2-yl)ethan-1-amine (60 mg, 20%) as a yellow oil. LCMS ESI-MS m/z: 271 [M+H]+.

Step 2: (S)-2,2,2-Trifluoro-N-methyl-1-(5-(pyridin-4-ylmethyl)-1H-imidazol-2-yl)ethan-1-amine and (R)-2,2,2-trifluoro-N-methyl-1-(5-(pyridin-4-ylmethyl)-1H-imidazol-2-yl)ethan-1-amine. The racemic mixture (60 mg) was purified by prep-SFC. Peak 1 was isolated as a yellow semi-solid (23 mg, 38%) and Peak 2 was isolated as a yellow semi-solid (21 mg, 35%).

Peak 1. 1H NMR (400 MHz, DMSO-d6, ppm): δ 8.49-8.43 (m, 2H), 7.27-7.21 (m, 2H), 6.87 (s, 1H), 4.29 (q, J=7.8 Hz, 1H), 3.88 (s, 2H), 2.26 (s, 3H). LCMS ESI-MS m/z: 271 [M+H]+.

Peak 2. 1H NMR (400 MHz, DMSO-d6, ppm): δ 8.49-8.43 (m, 2H), 7.27-7.21 (m, 2H), 6.88 (s, 1H), 4.30 (q, J=7.9 Hz, 1H), 3.88 (s, 2H), 2.26 (s, 3H). LCMS ESI-MS m/z: 271 [M+H]+.

The absolute stereochemistry was assigned arbitrarily.

Example 17 and 17a: (S)-2,2,2-Trifluoro-N,N-dimethyl-1-(5-(pyridin-4-ylmethyl)-1H-imidazol-2-yl)ethan-1-amine and (R)-2,2,2-Trifluoro-N,N-dimethyl-1-(5-(pyridin-4-ylmethyl)-1H-imidazol-2-yl)ethan-1-amine

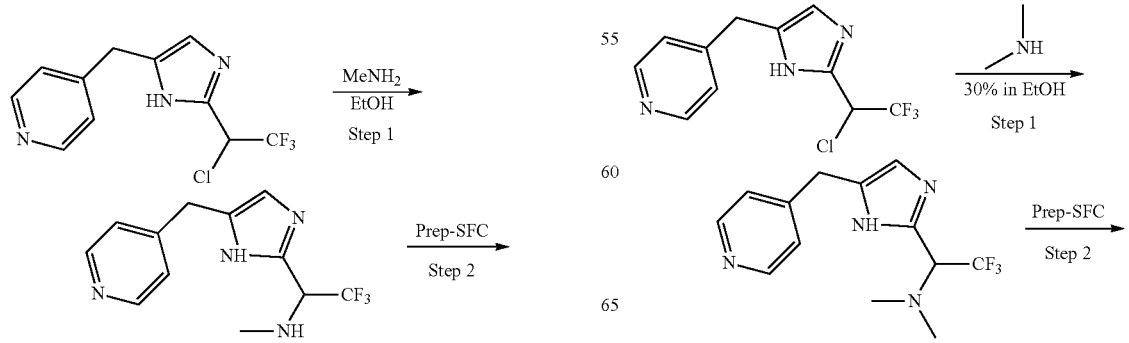

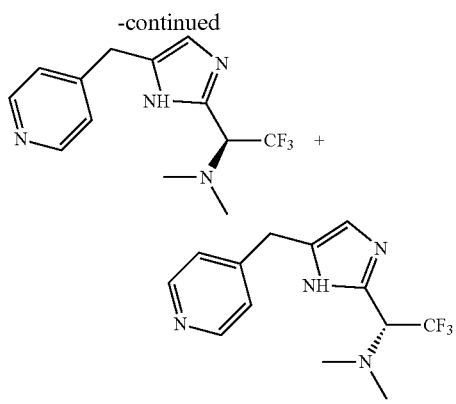

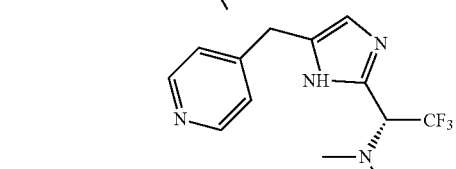

Step 1: (rac)-2,2,2-Trifluoro-N,N-dimethyl-1-(5-(pyridin-4-ylmethyl)-1H-imidazol-2-yl)ethan-1-amine. To a stirred solution of 4-((2-(1-chloro-2,2,2-trifluoroethyl)-1H-imidazol-5-yl)methyl)pyridine (Example 15, step 1, 300 mg, 1.1 mmol) in EtOH (3 mL) was added dimethylamine (30% in EtOH, 1 mL) dropwise at 0° C. under a nitrogen atmosphere. The resulting mixture was stirred for 2 h at room temperature under a nitrogen atmosphere. The resulting mixture was concentrated under reduced pressure to yield a yellow oil. The crude product (150 mg) was purified by prep-HPLC to afford (rac)-2,2,2-trifluoro-N,N-dimethyl-1-(5-(pyridin-4-ylmethyl)-1H-imidazol-2-yl)ethan-1-amine as a yellow oil (100 mg, 32.3%). LCMS ESI-MS m/z: 285 [M+H]+.

Step 2: (S)-2,2,2-Trifluoro-N,N-dimethyl-1-(5-(pyridin-4-ylmethyl)-1H-imidazol-2-yl)ethan-1-amine and (R)-2,2,2-Trifluoro-N,N-dimethyl-1-(5-(pyridin-4-ylmethyl)-1H-imidazol-2-yl)ethan-1-amine. (rac)-2,2,2-Trifluoro-N,N-dimethyl-1-(5-(pyridin-4-ylmethyl)-1H-imidazol-2-yl)ethan-1-amine (100 mg) was purified by prep-SFC. Peak 1 was isolated as a yellow oil (28 mg, 28%) and Peak 2 was isolated as a yellow oil (22 mg, 22%).

Peak 1. $^1$H NMR (400 MHz, DMSO-$d_6$, ppm): δ 11.98 (s, 1H), 8.48-8.42 (m, 2H), 7.26-7.20 (m, 2H), 6.86 (s, 1H), 4.48 (q, J=8.8 Hz, 1H), 3.89 (s, 2H), 2.29 (s, 6H). LCMS ESI-MS m/z: 285 [M+H]+.

Peak 2. $^1$H NMR (400 MHz, DMSO-$d_6$, ppm): δ 11.99 (s, 1H), 8.45 (s, 2H), 7.23 (d, J=5.0 Hz, 2H), 6.92 (s, 1H), 6.71 (s, OH), 4.48 (s, 1H), 3.95 (s, 1H), 3.86 (s, 1H), 2.29 (s, 6H). LCMS ESI-MS m/z: 285 [M+H]+.

The absolute stereochemistry was assigned arbitrarily.

Example 18: (E/Z)-2,2,2-Trifluoro-1-(4-(pyridin-4-ylmethyl)thiazol-2-yl)ethan-1-one oxime

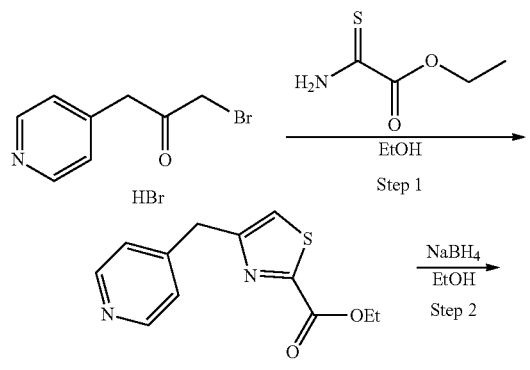

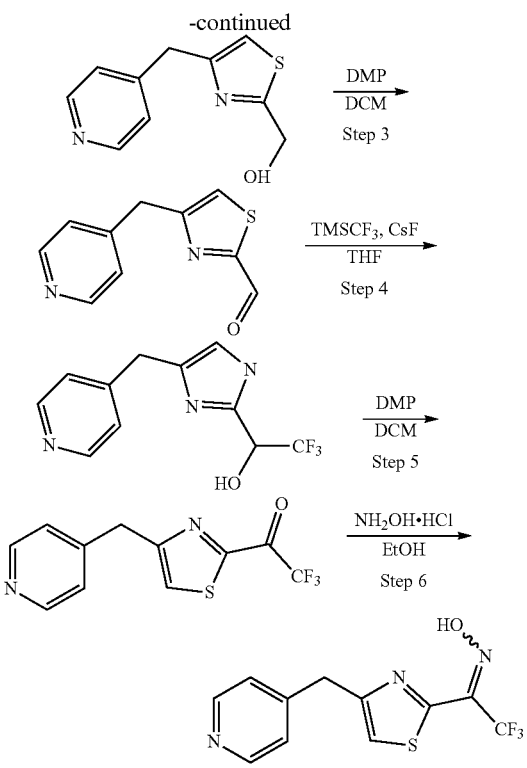

Step 1: Ethyl 4-(pyridin-4-ylmethyl)thiazole-2-carboxylate. A mixture of 1-bromo-3-(pyridin-4-yl)propan-2-one hydrobromide (13.7 g, 46.7 mmol) and ethyl 2-amino-2-thioxoacetate (6.8 g, 51.4 mmol) in EtOH (80 mL) was stirred for 4 h at 80° C. under a nitrogen atmosphere before being cooled to room temperature. The mixture was adjusted to pH 7 with sat. NaHCO$_3$ (aq), extracted with EtOAc (3×50 mL). The organic extracts were washed with brine (1×50 mL) and dried over anhydrous Na$_2$SO$_4$, filtered, and concentrated under reduced pressure. The resulting residue was purified by silica gel column chromatography to afford ethyl 4-(pyridin-4-ylmethyl)thiazole-2-carboxylate as a yellow oil (7.0 g, 60%). LCMS ESI-MS m/z: 249 [M+H]+.

Step 2: (4-(Pyridin-4-ylmethyl)thiazol-2-yl)methanol. A solution of ethyl 4-(pyridin-4-ylmethyl)thiazole-2-carboxylate (7.0 g, 28.2 mmol) in EtOH (100 mL) was treated with NaBH$_4$ (5.4 g, 141.0 mmol) for 4 h at room temperature under a nitrogen atmosphere. The reaction was quenched by the addition of sat. NH$_4$Cl (aq) (200 mL) at 0° C. and extracted with EtOAc (3×80 mL). The resulting organic extracts were concentrated under reduced pressure to afford (4-(pyridin-4-ylmethyl)thiazol-2-yl)methanol as a yellow oil (6.0 g). This compound was used in the next step without further purification. LCMS ESI-MS m/z: 207 [M+H]+.

Step 3: 4-(Pyridin-4-ylmethyl)thiazole-2-carbaldehyde. A solution of (4-(pyridin-4-ylmethyl)thiazol-2-yl)methanol (6.0 g, 22 mmol) in DCM (130 mL) was treated with DMP (10.2 g, 24 mmol) for 2 h at room temperature under a nitrogen atmosphere. The reaction was quenched by the addition of sat. aq. sodium thiosulfate (20 mL) at 0° C. The resulting mixture was basified to pH 7 with sat. aq. NaHCO$_3$. The aqueous layer was extracted with EtOAc (3×80 mL). The resulting mixture was concentrated under reduced pressure to afford 4-(pyridin-4-ylmethyl)thiazole-2-carbaldehyde (6.0 g) as a brown oil. This compound was used in the next step without further purification. LCMS ESI-MS m/z: 205 [M+H]+.

Step 4: 2,2,2-Trifluoro-1-(4-(pyridin-4-ylmethyl)thiazol-2-yl)ethan-1-ol. A solution of 4-(pyridin-4-ylmethyl)-1,3-thiazole-2-carbaldehyde (6.0 g, 14.7 mmol) in THF (100 mL) was treated with TMSCF₃ (2.5 g, 17.6 mmol) and stirred for 5 min at room temperature under a nitrogen atmosphere. CsF (2.7 g, 17.6 mmol) was then added in portions at 0° C. and the resulting mixture was stirred overnight at room temperature under a nitrogen atmosphere. The resulting mixture was concentrated under reduced pressure. The residue was purified by silica gel column chromatography to afford 2,2,2-trifluoro-1-(4-(pyridin-4-ylmethyl)thiazol-2-yl)ethan-1-ol (1.8 g, 44%) as a white solid. LCMS ESI-MS m/z: 275 [M+H]⁺.

Step 5: 2,2,2-Trifluoro-1-(4-(pyridine-4-ylmethyl)thiazol-2-yl)ethan-1-one. A mixture of 2,2,2-trifluoro-1-(4-(pyridin-4-ylmethyl) thiazol-2-yl)ethan-1-ol (500 mg, 1.8 mmol) in DCM (15 mL) was added DMP (850 mg, 2.0 mmol) in portions at room temperature under a nitrogen atmosphere. The resulting mixture was stirred 1 h at room temperature. The reaction was quenched by the addition of sat. aq. sodium thiosulfate (10 mL) at 0° C. The resulting mixture was basified to pH 7 with sat. aq. NaHCO₃. The aqueous layer was extracted with EtOAc (3×20 mL). The resulting mixture was concentrated under reduced pressure. The crude product was purified by silica gel column chromatography to yield 2,2,2-trifluoro-1-(4-(pyridin-4-ylmethyl)thiazol-2-yl)ethan-1-one (400 mg, 80%) as a white solid. LCMS ESI-MS m/z: 273 [M+H]⁺.

Step 6: (E/Z)-2,2,2-Trifluoro-1-(4-(pyridin-4-ylmethyl)thiazol-2-yl)ethan-1-one oxime. A mixture of 2,2,2-trifluoro-1-(4-(pyridin-4-ylmethyl)thiazol-2-yl)ethan-1-one (400 mg, 1.5 mmol) and NH₂OH·HCl (204 mg, 2.9 mmol) in EtOH (15 mL) was stirred overnight at 80° C. under a nitrogen atmosphere. The mixture was allowed to cool down to room temperature. The mixture was basified to pH 7 with sat. aq. NaHCO₃. The aqueous layer was extracted with EtOAc (3×20 mL). The resulting mixture was concentrated under reduced pressure to yield a yellow solid. The solid was triturated with EtOAc (20 mL) and filtered off to yield a yellow solid which was purified by prep-HPLC to yield (E/Z)-2,2,2-trifluoro-1-(4-(pyridin-4-ylmethyl)thiazol-2-yl)ethan-1-one oxime (31 mg, 7%) as a white solid. ¹H NMR (400 MHz, DMSO-d₆, ppm): δ 8.47 (s, 2H), 7.30 (s, 2H), 7.16 (s, 1H), 4.15 (s, 2H); LCMS ESI-MS m/z: 288 [M+H]⁺.

Example 19 and 19a: (S)-2,2,2-Trifluoro-1-(5-(pyridin-4-ylmethyl)thiazol-2-yl)ethan-1-amine and (R)-2,2,2-Trifluoro-1-(5-(pyridin-4-ylmethyl)thiazol-2-yl)ethan-1-amine

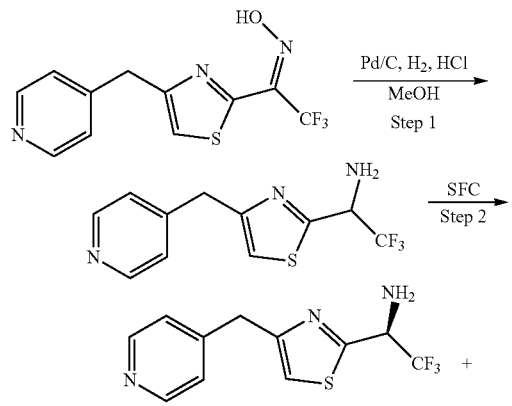

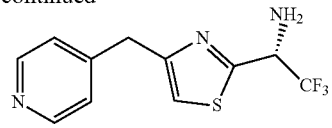

Step 1: 2,2,2-Trifluoro-1-(4-(pyridin-4-ylmethyl)thiazol-2-yl)ethan-1-amine. A solution of (E/Z)-2,2,2-trifluoro-1-(4-(pyridin-4-ylmethyl)thiazol-2-yl)ethan-1-one oxime (Example 18, step 6, 400 mg, 1.4 mmol) in MeOH (8 mL) was treated with 6 M HCl (20 mg, 0.5 mmol) for 2 min at room temperature followed by the addition of Pd/C (160 mg, 40 wt %) in portions at room temperature and stirred overnight at room temperature under a hydrogen atmosphere. The resulting mixture was filtered, and the filtrate was concentrated under reduced pressure to yield a yellow solid. The crude material (180 mg) was purified via prep-HPLC to afford 2,2,2-trifluoro-1-(4-(pyridin-4-ylmethyl)thiazol-2-yl)ethan-1-amine as a white solid (100 mg, 26%). LCMS ESI-MS m/z: 274 [M+H]⁺.

Step 2: (S)-2,2,2-Trifluoro-1-(5-(pyridin-4-ylmethyl)thiazol-2-yl)ethan-1-amine and (R)-2,2,2-trifluoro-1-(5-(pyridin-4-ylmethyl)thiazol-2-yl)ethan-1-amine. The racemic mixture of 2,2,2-trifluoro-1-(4-(pyridin-4-ylmethyl)thiazol-2-yl)ethan-1-amine (100 mg) was purified by prep-SFC. Peak 1 was isolated as a white solid (23 mg, 6%) and Peak 2 was isolated as a white solid (23 mg, 6%).

Peak 1. ¹H NMR (400 MHz, DMSO-d₆, ppm): δ 8.45-8.51 (m, 2H), 7.45 (s, 1H), 7.24-7.3 (m, 2H), 4.90 (q, J=7.9 Hz, 1H), 4.11 (s, 2H), 2.86 (s, 2H). LCMS ESI-MS m/z: 274 [M+H]⁺.

Peak 2. ¹H NMR (400 MHz, DMSO-d₆, ppm): δ 8.42-8.55 (m, 2H), 7.45 (s, 1H), 7.2-7.33 (m, 2H), 4.91 (s, 1H), 4.11 (s, 2H), 2.84 (s, 2H). LCMS ESI-MS m/z: 274 [M+H]⁺.

The absolute stereochemistry was assigned arbitrarily.

Example 20 and 20a: (S)-(4-(Pyridin-4-ylmethyl)-1H-imidazol-2-yl)(thiazol-5-yl)methanol and (R)-(4-(Pyridin-4-ylmethyl)-1H-imidazol-2-yl)(thiazol-5-yl)methanol

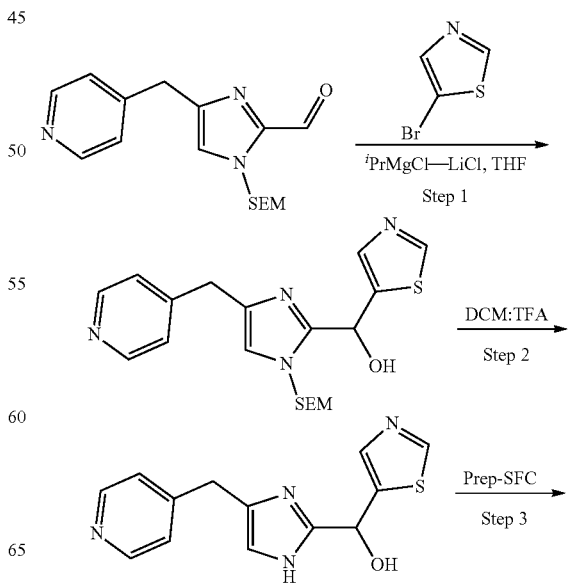

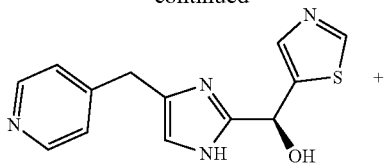

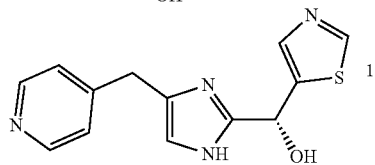

Step 1: (rac)-(4-(Pyridin-4-ylmethyl)-1-((2-(trimethylsilyl)ethoxy)methyl)-1H-imidazol-2-yl)(thiazol-5-yl)methanol. A solution of 5-bromothiazole (310 mg, 1.9 mmol) in THF (15 mL) was treated with iPrMgCl LiCl (1.6 mL, 2.1 mmol) for 30 min at 0° C. under a nitrogen atmosphere followed by the addition of 4-(pyridin-4-ylmethyl)-1-((2-(trimethylsilyl)ethoxy)methyl)-1H-imidazole-2-carbaldehyde (Example 3, step 4, 500 mg, 1.6 mmol) dropwise at 0° C. The resulting mixture was stirred for 1 h at room temperature under a nitrogen atmosphere. The reaction was quenched by the addition of water/ice (10 mL) at 0° C. and extracted with EtOAc (3×10 mL). The combined organic extracts were concentrated under reduced pressure. The residue was purified via reverse phase chromatography to yield (rac)-(4-(pyridin-4-ylmethyl)-1-((2-(trimethylsilyl)ethoxy)methyl)-1H-imidazol-2-yl)(thiazol-5-yl)methanol (200 mg, 31%) as a yellow oil. LCMS ESI-MS m/z: 403 [M+H]⁺.

Step 2: (rac)-(4-(Pyridin-4-ylmethyl)-1H-imidazol-2-yl)(thiazol-5-yl)methanol. A solution of (4-(pyridin-4-ylmethyl)-1-((2-(trimethylsilyl)ethoxy)methyl)-1H-imidazol-2-yl)(thiazol-5-yl)methanol (200 mg, 0.5 mmol) in DCM (8.0 mL) was treated with TFA (8.0 mL) overnight at room temperature under a nitrogen atmosphere. The resulting mixture was concentrated under reduced pressure and then treated with ethane-1,2-diamine (0.5 mL) at 0° C. The resulting mixture was concentrated under reduced pressure to yield a yellow solid. The residue was purified first via reverse phase chromatography to yield (rac)-(4-(pyridin-4-ylmethyl)-1H-imidazol-2-yl)(thiazol-5-yl)methanol (180 mg, 60%) as a yellow solid. The crude product was purified, second via prep-HPLC to yield (rac)-(4-(pyridin-4-ylmethyl)-1H-imidazol-2-yl)(thiazol-5-yl)methanol (100 mg, 74%) as a white solid.

Step 3: (S)-(4-(Pyridin-4-ylmethyl)-1H-imidazol-2-yl)(thiazol-5-yl)methanol and (R)-(4-(Pyridin-4-ylmethyl)-1H-imidazol-2-yl)(thiazol-5-yl)methanol. (rac)-(4-(Pyridin-4-ylmethyl)-1H-imidazol-2-yl)(thiazol-5-yl)methanol (100 mg) was purified by prep-SFC. Peak 1 was isolated as a white solid (29 mg, 22%) and Peak 2 was isolated as a white solid (29 mg, 21%).

Peak 1. ¹H NMR (400 MHz, DMSO-$d_6$, ppm): δ 11.95 (s, 1H), 9.00 (s, 1H), 8.50-8.36 (m, 2H), 7.74 (s, 1H), 7.29-7.18 (m, 2H), 6.77 (s, 1H), 6.60 (dd, J=4.5, 1.9 Hz, 1H), 6.02 (d, J=4.5 Hz, 1H), 3.82 (s, 2H). LCMS ESI-MS m/z: 273 [M+H]⁺.

Peak 2. ¹H NMR (400 MHz, DMSO-$d_6$, ppm): δ 12.00 (d, J=62.8 Hz, 1H), 9.00 (s, 1H), 8.44 (d, J=5.0 Hz, 2H), 7.74 (s, 1H), 7.31-7.14 (m, 2H), 6.82 (s, 1H), 6.63-6.50 (m, 1H), 6.02 (d, J=4.4 Hz, 1H), 3.80 (s, 2H). LCMS ESI-MS m/z: 273 [M+H]⁺.

The absolute stereochemistry was assigned arbitrarily.

Example 21: (rac)-(5-((3-Methylpyridin-4-yl)methyl)-1H-imidazol-2-yl)(thiazol-5-yl)methanol

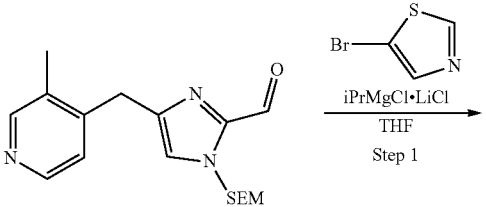

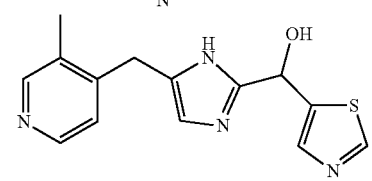

Step 1: (5-((3-Methylpyridin-4-yl)methyl)-1-((2-(trimethylsilyl)ethoxy)methyl)-1H-imidazol-2-yl)(thiazol-5-yl)methanol. To a stirred solution of 5-bromo-1,3-thiazole (430 mg, 2.62 mmol) in THF (25 mL) was added iPrMgCl·LiCl (1.92 mL, 2.49 mmol, 1.3 M solution in THF) dropwise over 10 min at 0° C. under a nitrogen atmosphere. The reaction mixture was stirred for 10 min and a solution of (rac)-4-((3-methylpyridin-4-yl)methyl)-1-((2-(trimethylsilyl)ethoxy)methyl)-1H-imidazole-2-carbaldehyde (Example 25, step 4, 435 mg, 1.31 mmol) in 1 mL THF was added dropwise into the reaction system. The resulting mixture was stirred for 1 h. This material was combined with another 50 mg batch and the resulting mixture was quenched with sat. NH₄Cl (50 mL) at 0° C. The organics were then extracted with EtOAc (2×30 mL). The combined organic layers were dried over anhydrous Na₂SO₄, filtered, concentrated under reduced pressure. The crude product was purified via silica gel column chromatography to afford (4-((3-methylpyridin-4-yl)methyl)-1-((2-(trimethylsilyl)ethoxy)methyl)-1H-imidazol-2-yl)(thiazol-5-yl)methanol (423 mg, 63%) as a light brown oil. LCMS ESI-MS m/z: =417 [M+H]⁺.

Step 2: (rac)-(4-((3-Methylpyridin-4-yl)methyl)-1-((2-(trimethylsilyl)ethoxy)methyl)-1H-imidazol-2-yl)(thiazol-5-yl)methanol. To a stirred solution of (5-((3-methylpyridin-4-yl)methyl)-1-((2-(trimethylsilyl)ethoxy)methyl)-1H-imidazol-2-yl)(thiazol-5-yl)methanol (373 mg, 0.89 mmol) in DCM (4 mL) was added TFA (4 mL) dropwise at 0° C. The resulting mixture was warmed to room temperature and stirred for 12 h. This mixture was combined with another 50.0 mg batch and the resulting mixture was concentrated under reduced pressure. The residue was basified to pH 8-9 with sat. NaHCO₃, and the organics were extracted with DCM (3×20 mL). The combined organic layers were dried over anhydrous MgSO₄, filtered, and concentrated under reduced pressure. The crude product was purified by reverse phase chromatography to afford (rac)-(5-((3-methylpyridin-4-yl)methyl)-1H-imidazol-2-yl)(thiazol-5-yl)methanol (101 mg, 34%) as a light-yellow solid. ¹H NMR (400 MHz, DMSO-d$_6$, ppm): δ 8.98 (s, 1H), 8.32-8.24 (m, 2H), 7.73 (s, 1H), 7.08 (d, J=4.9 Hz, 1H), 6.67 (s, 1H), 6.01 (s, 2H), 3.79 (s, 2H), 2.27 (s, 3H). LCMS ESI-MS m/z: =287 [M+H]$^+$.

Example 22: 3,5-Dichloro-4-((2-(2,2,2-trifluoroethyl)-1H-imidazol-5-yl)methyl)pyridine

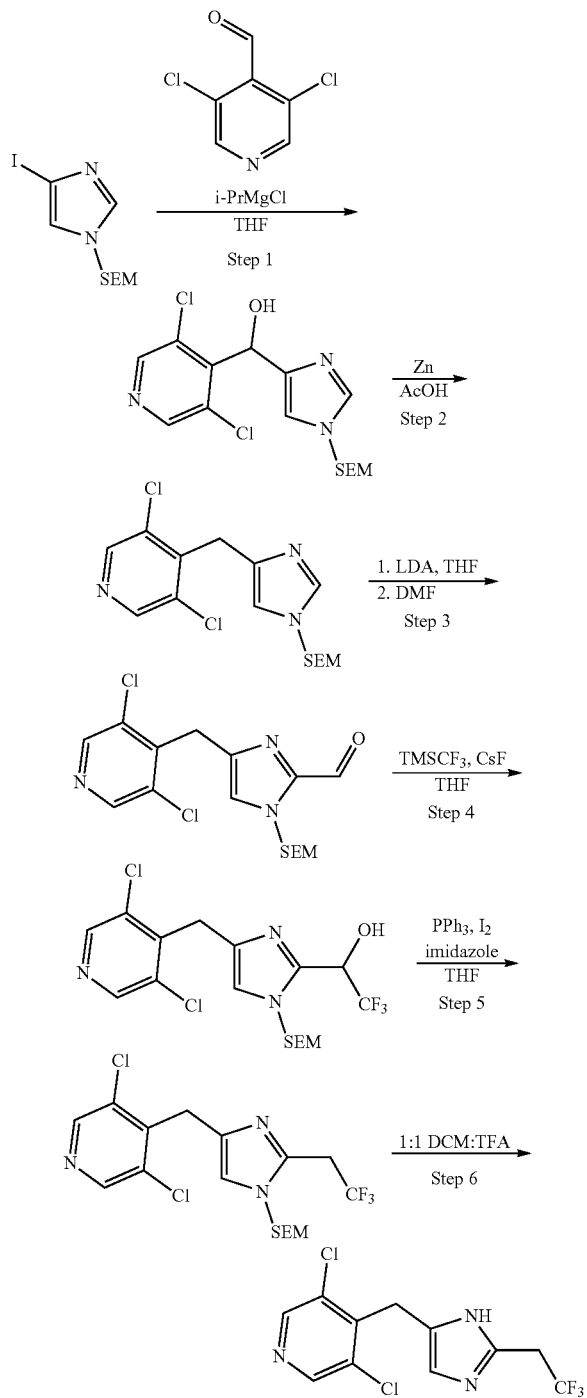

Step 1: (3,5-Dichloropyridin-4-yl)(1-((2-(trimethylsilyl)ethoxy)methyl)-1H-imidazol-4-yl)methanol. To a solution of 4-iodo-1-((2-(trimethylsilyl)ethoxy)methyl)-1H-imidazole (6.0 g, 18.5 mmol) in tetrahydrofuran (60 mL) was added bromo(isopropyl)magnesium (22.2 mL, 22.2 mmol) dropwise over 10 min at −15° C. under a nitrogen atmosphere and stirred for 30 min. To the resulting mixture was added 3,5-dichloroisonicotinaldehyde (3.9 g, 22.2 mmol) in portions and stirred for additional 30 min. This mixture was combined with another 500 mg batch and the resulting mixture was quenched with the addition of sat. NH$_4$Cl (200 mL) at 0° C. The organics were extracted with EtOAc (2×50 mL). The combined organic layers were dried over anhydrous Na$_2$SO$_4$, filtered, and concentrated under reduced pressure to yield a light yellow oil. The crude product was purified via silica gel column chromatography to afford (3,5-dichloropyridin-4-yl)(1-((2-(trimethylsilyl)ethoxy)methyl)-1H-imidazol-4-yl)methanol (6.40 g, 85%) as a light-yellow solid. LCMS ESI-MS m/z: =374 [M+H]$^+$.

Step 2: 3,5-Dichloro-4-((1-((2-(trimethylsilyl)ethoxy)methyl)-1H-imidazol-4-yl)methyl)pyridine. A solution of (3,5-dichloropyridin-4-yl)(1-((2-(trimethylsilyl)ethoxy)methyl)-1H-imidazol-4-yl)methanol (5.80 g, 15.5 mmol) in acetic acid (58 mL) was treated with zinc (12.1 g, 186 mmol) at room temperature under nitrogen atmosphere. The resulting mixture was heated to 80° C. and stirred for 1 h. The resulting mixture was then cooled to room temperature and combined with another 500 mg batch. The precipitated solids were filtered, and the filter cake was rinsed with DCM (2×30 mL). The filtrate was concentrated under reduced pressure. The residue was basified to pH 8-9 with sat. Na$_2$CO$_3$ and the organics were extracted with DCM (2×30 mL). The combined organic layers were dried over anhydrous MgSO$_4$, filtered, and concentrated under reduced pressure. The crude product was purified via silica gel column chromatography to afford 3,5-dichloro-4-((1-((2-(trimethylsilyl)ethoxy)methyl)-1H-imidazol-4-yl)methyl)pyridine (4.98 g, 80%) as a light yellow oil. LCMS ESI-MS m/z: =357, 358 [M+H]$^+$.

Step 3: 4-((3,5-Dichloropyridin-4-yl)methyl)-1-((2-(trimethylsilyl)ethoxy)methyl)-1H-imidazole-2-carbaldehyde. A solution of 3,5-dichloro-4-((1-((2-(trimethylsilyl)ethoxy)methyl)-1H-imidazol-4-yl)methyl)pyridine (3.9 g, 10.9 mmol) in tetrahydrofuran (78 mL) was treated with LDA (16.3 mL, 32.7 mmol, 2 M solution in THF) at −78° C. under a nitrogen atmosphere. The resulting mixture was stirred for additional 5 min and DMF (1.59 g, 21.8 mmol) was added dropwise. The resulting mixture was stirred for additional 0.5 h. This mixture was combined with another 500 mg batch and the resulting mixture was quenched with the addition of sat. NH$_4$Cl (aq) (100 mL) at 0° C. The organics were extracted with EtOAc (3×100 mL). The combined organic layers were dried over anhydrous Na$_2$SO$_4$, filtered, and concentrated under reduced pressure. The crude product was purified via silica gel column chromatography to afford 4-((3,5-dichloropyridin-4-yl)methyl)-1-((2-(trimethylsilyl)ethoxy)methyl)-1H-imidazole-2-carbaldehyde (2.9 g, 54%) as a light yellow oil. LCMS ESI-MS m/z: =386 [M+H]$^+$.

Step 4: 1-(4-((3,5-Dichloropyridin-4-yl)methyl)-1-((2-(trimethylsilyl)ethoxy)methyl)-1H-imidazol-2-yl)-2,2,2-trifluoroethan-1-ol. A solution of 4-((3,5-dichloropyridin-4-yl)methyl)-1-((2-(trimethylsilyl)ethoxy)methyl)-1H-imidazole-2-carbaldehyde (2.40 g, 6.21 mmol) in tetrahydrofuran (48 mL) was treated with trifluoromethyltrimethylsilane (1.32 g, 9.32 mmol) at room temperature under a nitrogen atmosphere. The reaction was cooled to 0° C. and CsF (1.42 g, 9.32 mmol) was added in portions. The reaction was then warmed to room temperature and stirred for 2 h. This mixture was combined with another 500 mg batch was combined and the resulting mixture was concentrated under reduced pressure. The crude product was purified via silica gel column chromatography to afford 1-(4-((3,5-dichloropyridin-4-yl)methyl)-1-((2-(trimethylsilyl)ethoxy)methyl)-1H-imidazol-2-yl)-2,2,2-trifluoroethan-1-ol (2.9 g, 85%) as a light yellow oil. LCMS ESI-MS m/z: =456 [M+H]⁺.

Step 5: 3,5-Dichloro-4-((2-(2,2,2-trifluoroethyl)-1-((2-(trimethylsilyl)ethoxy)methyl)-1H-imidazol-4-yl)methyl)pyridine. A solution of 1-(4-((3,5-dichloropyridin-4-yl)methyl)-1-((2-(trimethylsilyl)ethoxy)methyl)-1H-imidazol-2-yl)-2,2,2-trifluoroethan-1-ol (2.40 g, 5.26 mmol) in tetrahydrofuran (24 mL) was treated with triphenylphosphine (1.66 g, 6.31 mmol), imidazole (0.43 g, 6.31 mmol) and iodine (0.80 g, 3.16 mmol) under a nitrogen atmosphere. The reaction was heated to 70° C. and stirred for 1 h. This mixture was combined with another 500 mg batch and the resulting mixture was quenched with the addition of sat. aq. Na₂SO₃ (100 mL) at 0° C. The organics were extracted with EtOAc (3×50 mL). The combined organic layers were dried over anhydrous Na₂SO₄, filtered, and concentrated under reduced pressure. The crude product was purified by reverse phase chromatography to afford 3,5-dichloro-4-((2-(2,2,2-trifluoroethyl)-1-((2-(trimethylsilyl)ethoxy)methyl)-1H-imidazol-4-yl)methyl)pyridine (2.40 g, 85%) as a light yellow oil. LCMS ESI-MS m/z: =440 [M+H]⁺.

Step 6: 3,5-Dichloro-4-((2-(2,2,2-trifluoroethyl)-1H-imidazol-5-yl)methyl)pyridine. A solution of 3,5-dichloro-4-((2-(2,2,2-trifluoroethyl)-1-((2-(trimethylsilyl)ethoxy)methyl)-1H-imidazol-4-yl)methyl)pyridine (500 mg, 1.14 mmol) in DCM (2.5 mL) was treated with trifluoroacetic acid (2.5 mL) dropwise at 0° C. under nitrogen atmosphere. The reaction was warmed to room temperature and stirred for 12 h. The resulting mixture was concentrated under vacuum. The residue was basified to pH 7-8 with saturated NaHCO₃, upon which the product precipitated from the solution. The precipitate was collected by filtration and rinsed with water (2×4 mL) to afford 3,5-dichloro-4-((2-(2,2,2-trifluoroethyl)-1H-imidazol-5-yl)methyl)pyridine (63 mg, 17%) as an off-white solid. ¹H NMR (400 MHz, DMSO-d₆, ppm): δ 11.99 (s, 1H), 8.61 (s, 2H), 6.76 (s, 1H), 4.11 (s, 2H), 3.65 (q, J=11.2 Hz, 2H); ¹⁹F NMR (376 MHz, DMSO-d₆, ppm): δ−63.63, −63.66, −63.71; LCMS ESI-MS m/z: =310 [M+H]⁺.

Example 23: (rac)-1-(4-((3-Chloropyridin-4-yl)methyl)-1H-imidazol-2-yl)-2,2,2-trifluoroethan-1-ol

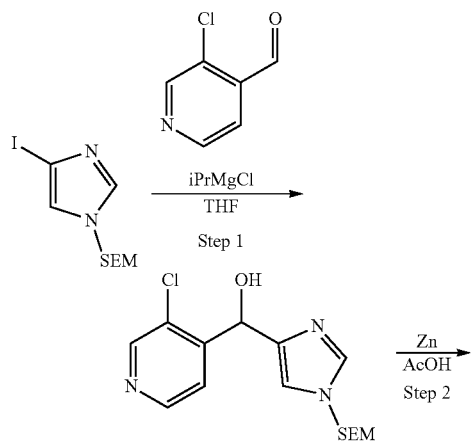

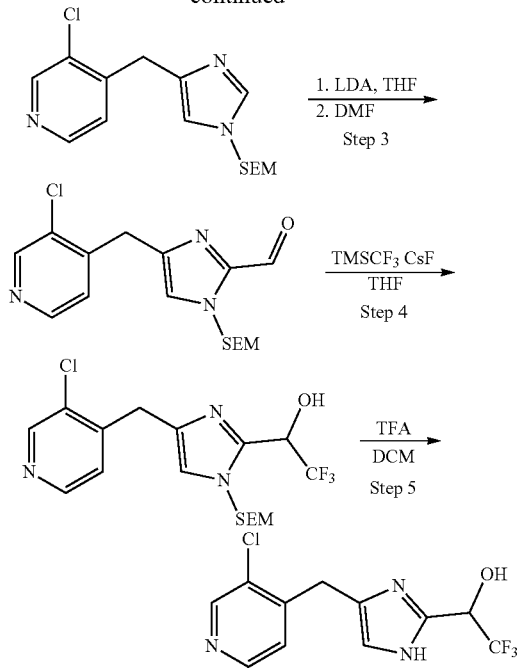

Step 1: (3-Chloropyridin-4-yl)(1-((2-(trimethylsilyl)ethoxy)methyl)-1H-imidazol-4-yl)methanol. To a solution of 4-iodo-1-((2-(trimethylsilyl)ethoxy)methyl)-1H-imidazole (Example 3, step 1, 10 g, 31 mmol) in THF (100 mL) was added isopropylmagnesium bromide (37 mL, 37.0 mmol, 1 M solution in THF) dropwise over 20 min at 0° C. under a nitrogen atmosphere. The resulting mixture was stirred for 0.5 h, and 3-chloroisonicotinaldehyde (5.2 g, 37 mmol) was added dropwise over 10 min. The resulting mixture was stirred for 1 h at 0° C. Upon the completion of the reaction, it was quenched by the addition of sat. aq. NH₄Cl (200 mL) at 0° C. The aqueous layer was extracted with EtOAc (3×100 mL). The combined organic layers were dried over anhydrous Na₂SO₄, filtered, and concentrated under reduced pressure to yield a light yellow oil. The crude product was purified via silica gel column chromatography to afford (3-chloropyridin-4-yl)(1-((2-(trimethylsilyl)ethoxy)methyl)-1H-imidazol-4-yl)methanol (2.5 g, 24%) as a light yellow oil. LCMS ESI-MS m/z: 340 [M+H]⁺.

Step 2: 3-Chloro-4-((1-((2-(trimethylsilyl)ethoxy)methyl)-1H-imidazol-4-yl)methyl)pyridine. To a solution of (3-chloropyridin-4-yl)(1-((2-(trimethylsilyl)ethoxy)methyl)-1H-imidazol-4-yl)methanol (1.3 g, 3.8 mmol) in acetic acid (13 mL) was added zinc (3 g, 46.0 mmol) at room temperature under a nitrogen atmosphere. The resulting mixture was heated to 80° C. and stirred for 2 h. Upon the completion of the reaction, the precipitated solids were filtered, and the solids were rinsed with DCM (2×30 mL). Another 200 mg batch was combined with this mixture and the filtrate was concentrated under reduced pressure. This residue was dissolved in DCM (30 mL) and washed with sat. Na₂CO₃ (2×15 mL). The organic layer was dried over anhydrous MgSO₄, filtered, and concentrated under reduced pressure to yield a light yellow oil. The crude product was purified via silica gel column chromatography to afford 3-chloro-4-((1-((2-(trimethylsilyl)ethoxy)methyl)-1H-imidazol-4-yl)methyl)pyridine (1.1 g, 78%) as a light yellow oil. LCMS ESI-MS m/z: 324 [M+H]⁺.

Step 3: 4-((3-Chloropyridin-4-yl)methyl)-1-((2-(trimethylsilyl)ethoxy)methyl)-1H-imidazole-2-carbaldehyde. To a solution of 3-chloro-4-((1-((2-(trimethylsilyl)ethoxy)methyl)-1H-imidazol-4-yl)methyl)pyridine (400 mg, 1.2 mmol) in tetrahydrofuran (8 mL) was added LDA (1.49 mL, 34.9 mmol, 2 M solution in THF) dropwise at −78° C. and stirred for 5 min. To the above mixture was added DMF (180 mg, 2.5 mmol) dropwise at −78° C. and stirred for 30 min. The reaction was then quenched with the addition of sat. NH$_4$Cl (30 mL) at 0° C. The resulting mixture was extracted with EtOAc (2×30 mL). The combined organic layers were dried over anhydrous Na$_2$SO$_4$, filtered, and concentrated under reduced pressure to yield a light yellow oil. The crude product was purified via silica gel column chromatography to afford 4-((3-chloropyridin-4-yl)methyl)-1-((2-(trimethylsilyl)ethoxy)methyl)-1H-imidazole-2-carbaldehyde (143 mg, 32%) as a light yellow oil. LCMS ESI-MS m/z: 352 [M+H]$^+$.

Step 4: 1-(4-((3-Chloropyridin-4-yl)methyl)-1-((2-(trimethylsilyl)ethoxy)methyl)-1H-imidazol-2-yl)-2,2,2-trifluoroethan-1-ol. To a solution of 4-((3-chloropyridin-4-yl)methyl)-1-((2-(trimethylsilyl)ethoxy)methyl)-1H-imidazole-2-carbaldehyde (120 mg, 0.341 mmol) in tetrahydrofuran (2.4 mL) was added trifluoromethyltrimethylsilane (72.7 mg, 0.512 mmol) at 25° C. under a nitrogen atmosphere. The reaction was cooled to 0° C. and CsF (77.7 mg, 0.512 mmol) was added in portions. The resulting mixture was warmed to room temperature and stirred for 2 h. The resulting mixture was combined with another 20.0 mg batch and concentrated under reduced pressure. The crude product was purified by reverse phase chromatography to afford 1-(4-((3-chloropyridin-4-yl)methyl)-1-((2-(trimethylsilyl)ethoxy)methyl)-1H-imidazol-2-yl)-2,2,2-trifluoroethan-1-ol (124 mg, 74%) as a light yellow oil. LCMS ESI-MS m/z: =422 [M+H]$^+$.

Step 5: 1-(4-((3-Chloropyridin-4-yl)methyl)-1H-imidazol-2-yl)-2,2,2-trifluoroethan-1-ol. To a solution of 1-(4-((3-chloropyridin-4-yl)methyl)-1-((2-(trimethylsilyl)ethoxy)methyl)-1H-imidazol-2-yl)-2,2,2-trifluoroethan-1-ol (80.0 mg, 0.190 mmol) in DCM (0.4 mL) was added TFA (0.4 mL) dropwise at 0° C. The reaction was warmed to room temperature and stirred for 12 h. The resulting mixture was then concentrated under reduced pressure. The residue was basified to pH 7-8 with sat. NaHCO$_3$ and extracted with DCM (3×15 mL). The combined organic layers dried over anhydrous MgSO$_4$, filtered, and concentrated under reduced pressure. The crude product was purified by prep-HPLC to afford 1-(4-((3-chloropyridin-4-yl)methyl)-1H-imidazol-2-yl)-2,2,2-trifluoroethan-1-ol (14 mg, 25%) as off-white solid. $^1$H NMR: (400 MHz, DMSO-d$_6$, ppm): δ 12.24 (d, J=50.4 Hz, 1H), 8.58 (d, J=13.4 Hz, 1H), 8.43 (dd, J=17.9, 4.9 Hz, 1H), 7.27 (dd, J=19.0, 4.9 Hz, 1H), 7.11 (dd, J=15.6, 5.8 Hz, 1H), 6.95-6.59 (m, 1H), 5.13 (p, J=6.8 Hz, 1H), 3.98 (d, J=39.2 Hz, 2H). LCMS ESI-MS m/z: =402 [M+H]$^+$.

Example 24, 24a, 24b, 24c: (S)-2,2,2-Trifluoro-1-(4-((S)-1-(pyridin-4-yl)ethyl)-1H-imidazol-2-yl)ethan-1-ol, (R)-2,2,2-Trifluoro-1-(4-((R)-1-(pyridin-4-yl)ethyl)-1H-imidazol-2-yl)ethan-1-ol, (S)-2,2,2-Trifluoro-1-(4-((R)-1-(pyridin-4-yl)ethyl)-1H-imidazol-2-yl)ethan-1-ol, and (R)-2,2,2-Trifluoro-1-(4-((S)-1-(pyridin-4-yl)ethyl)-1H-imidazol-2-yl)ethan-1-ol

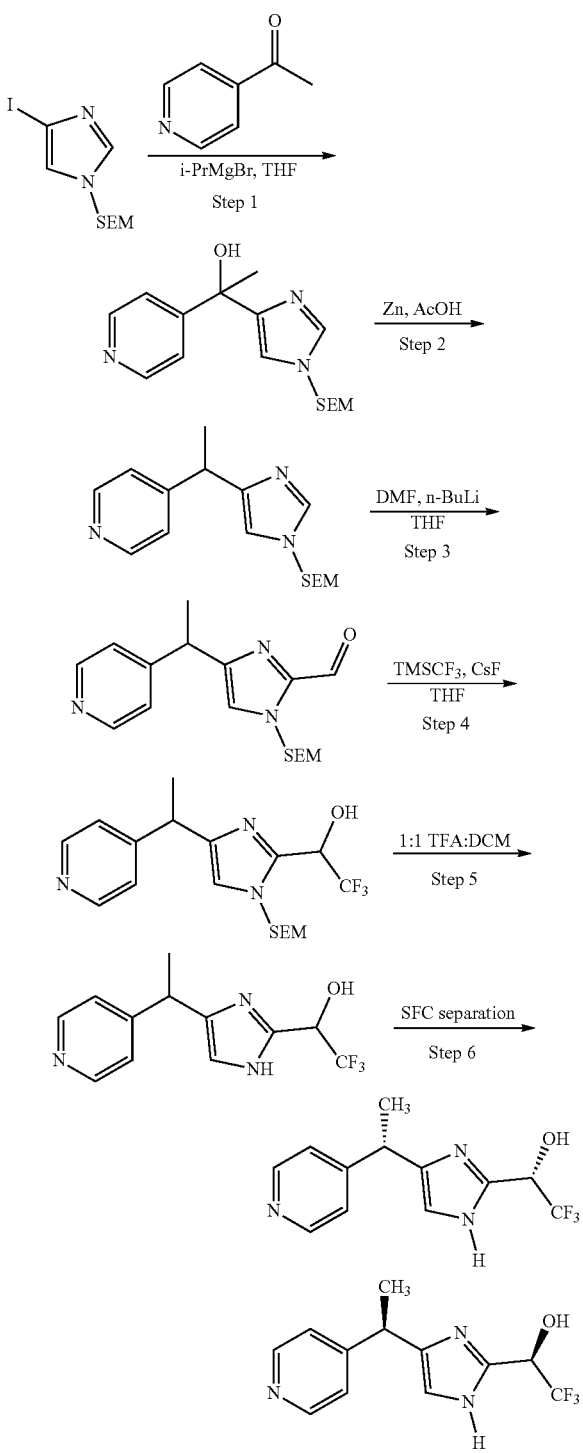

-continued

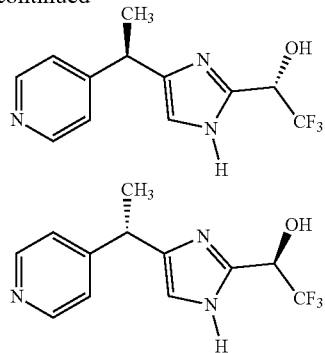

Step 1: 1-(Pyridin-4-yl)-1-(1-((2-(trimethylsilyl)ethoxy)methyl)-1H-imidazol-4-yl)ethan-1-ol. To a stirred solution of 4-iodo-1-((2-(trimethylsilyl)ethoxy)methyl)-1H-imidazole (5.0 g, 15.4 mmol) in THF (50 mL) was added 1 M i-PrMgBr (16.9 mL, 16.9 mmol) dropwise at 0° C. under a nitrogen atmosphere. The reaction mixture was stirred at 0° C. for 30 min. Then, 1-(pyridin-4-yl)ethan-1-one (2.05 g, 16.9 mmol) was added dropwise and the resulting mixture was warmed to room temperature and stirred for 2 h. The reaction mixture was poured to ice water (50 mL) and the organics were extracted with EtOAc (2×50 mL). The combined organic layer was washed with brine (100 mL), dried over anhydrous $Na_2SO_4$, filtered, and concentrated under reduced pressure. The crude product was purified by reverse phase chromatography to afford 1-(pyridin-4-yl)-1-(1-((2-(trimethylsilyl)ethoxy)methyl)-1H-imidazol-4-yl)ethan-1-ol (3.7 g, 75%) as a light yellow oil. LCMS ESI-MS m/z: =320 $[M+H]^+$.

Step 2: 4-(1-(1-((2-(Trimethylsilyl)ethoxy)methyl)-1H-imidazol-4-yl)ethyl)pyridine. A mixture of 1-(pyridin-4-yl)-1-(1-((2-(trimethylsilyl)ethoxy)methyl)-1H-imidazol-4-yl)ethan-1-ol (3.7 g, 11.5 mmol) and Zn (9.09 g, 139 mmol) in AcOH (37 mL) was stirred overnight at 80° C. under a nitrogen atmosphere. The resulting mixture was cooled to room temperature. The resulting mixture was filtered, and the filter cake was washed with MeOH (30 mL). The filtrate was concentrated under reduced pressure. The crude product was purified by reverse phase chromatography to afford 4-(1-(1-((2-(trimethylsilyl)ethoxy)methyl)-1H-imidazol-4-yl)ethyl)pyridine (3 g, 81%) as a yellow oil. LCMS ESI-MS m/z: =304 $[M+H]^+$.

Step 3: 4-(1-(Pyridin-4-yl)ethyl)-1-((2-(trimethylsilyl)ethoxy)methyl)-1H-imidazole-2-carbaldehyde. To a stirred solution of 4-(1-(1-((2-(trimethylsilyl)ethoxy)methyl)-1H-imidazol-4-yl)ethyl)pyridine (2.6 g, 8.56 mmol) in THF (50 mL) was added 2.5 M n-BuLi (10.2 mL, 25.7 mmol) dropwise at −78° C. under nitrogen atmosphere. The reaction mixture was stirred for 30 min. Then, DMF (1.25 g, 17.1 mmol) was added dropwise to the mixture and the reaction warmed to room temperature. The resulting mixture was stirred for 5 h. The reaction mixture was then poured to sat. $NH_4Cl$ (60 mL) at 0-5° C. The organics were extracted with EtOAc (2×50 mL). The combined organic phase was washed with brine (80 mL), dried over anhydrous $Na_2SO_4$, filtered, and concentrated under reduced pressure. The crude product was purified by reverse phase chromatography to afford 4-(1-(pyridin-4-yl)ethyl)-1-((2-(trimethylsilyl)ethoxy)methyl)-1H-imidazole-2-carbaldehyde (1.2 g, 41%) as a light yellow oil. LCMS ESI-MS m/z: =332 $[M+H]^+$.

Step 4: 2,2,2-Trifluoro-1-(4-(1-(pyridin-4-yl)ethyl)-1-((2-(trimethylsilyl)ethoxy)methyl)-1H-imidazol-2-yl)ethan-1-ol. To a stirred mixture of 4-(1-(pyridin-4-yl)ethyl)-1-((2-(trimethylsilyl)ethoxy)methyl)-1H-imidazole-2-carbaldehyde (1.10 g, 3.31 mmol) and $TMSCF_3$ (0.71 g, 4.97 mmol) in THF (20 mL) was added CsF (0.76 g, 4.97 mmol) in portions at 5-10° C. The resulting mixture was warmed to room temperature and stirred for 2 h under a nitrogen atmosphere. The reaction mixture was poured to ice water (30 mL) and the organics were extracted with EtOAc (3×20 mL). The combined organic layers were washed with brine (50 mL), dried over anhydrous $Na_2SO_4$, filtered, and concentrated under reduced pressure. The crude product was used in the next step directly without further purification. LCMS ESI-MS m/z: =402 $[M+H]^+$.

Step 5: 2,2,2-Trifluoro-1-(4-(1-(pyridin-4-yl)ethyl)-1H-imidazol-2-yl)ethan-1-ol. To a mixture of 2,2,2-trifluoro-1-(4-(1-(pyridin-4-yl)ethyl)-1-((2-(trimethylsilyl)ethoxy)methyl)-1H-imidazol-2-yl)ethan-1-ol (1.2 g, 2.98 mmol) in DCM (12 mL) was added TFA (12 mL) dropwise at 5-10° C. under a nitrogen atmosphere. The resulting mixture was stirred overnight at room temperature and concentrated under reduced pressure. The residue was dissolved in EtOAc (10 mL) and $H_2O$ (10 mL), the resulting mixture was basified to pH 10 with sat. $Na_2CO_3$ (aq). The organics were extracted with EtOAc (3×10 mL). The combined organic layers were washed with brine (30 mL), dried over anhydrous $Na_2SO_4$, filtered, and concentrated under reduced pressure. The crude product was purified by reverse phase chromatography to afford 2,2,2-trifluoro-1-(4-(1-(pyridin-4-yl)ethyl)-1H-imidazol-2-yl)ethan-1-ol (0.50 g, 51% over 2 steps) as a yellow solid. LCMS ESI-MS m/z: =272 $[M+H]^+$.

Step 6: (S)-2,2,2-Trifluoro-1-(4-((S)-1-(pyridin-4-yl)ethyl)-1H-imidazol-2-yl)ethan-1-ol, (R)-2,2,2-Trifluoro-1-(4-((R)-1-(pyridin-4-yl)ethyl)-1H-imidazol-2-yl)ethan-1-ol, (S)-2,2,2-Trifluoro-1-(4-((R)-1-(pyridin-4-yl)ethyl)-1H-imidazol-2-yl)ethan-1-ol, and (R)-2,2,2-Trifluoro-1-(4-((S)-1-(pyridin-4-yl)ethyl)-1H-imidazol-2-yl)ethan-1-ol. rac-2,2,2-Trifluoro-1-(4-[1-(pyridin-4-yl)ethyl]-1H-imidazol-2-yl)ethanol (350 mg) was separated by Prep-SFC to afford Peak 1 (57 mg, 16.3%, de=100%) as a white solid and Peak 2 (150 mg), a mixture of other 3 stereoisomers as a white solid. Peak 2 was further purified by Prep-SFC to afford Peak 3 (15.3 mg, 10%, de=98.6%) as a white solid and Peak 4 (50 mg), a mixture remaining 2 stereoisomers as a white solid. Peak 4 was subjected to further purification by Prep-SFC to afford Peak 5 (11.2 mg, 22%, de=99.8%) as a white solid and Peak 6 (8.8 mg, 18%) as a white solid.

Peak 1. $^1H$ NMR: (400 MHz, DMSO-$d_6$, ppm): δ 12.12 (s, 1H), 8.44 (d, 2H), 7.24 (d, 2H), 7.06 (d, J=5.9 Hz, 1H), 6.91 (s, 1H), 5.16-5.04 (m, 1H), 4.04 (s, 1H), 1.50 (d, J=7.2 Hz, 3H). LCMS ESI-MS m/z: =272 $[M+H]^+$.

Peak 3. $^1H$ NMR: (400 MHz, DMSO-$d_6$, ppm): δ 12.10 (s, 1H), 8.44 (d, J=5.1 Hz, 2H), 7.25 (d, J=5.1 Hz, 2H), 7.15-6.65 (m, 2H), 5.10 (q, J=7.3 Hz, 1H), 4.03 (s, 1H), 1.50 (d, J=7.1 Hz, 3H). LCMS ESI-MS m/z: =272 $[M+H]^+$.

Peak 5. $^1H$ NMR: (400 MHz, DMSO-$d_6$, ppm): δ 12.25-12.03 (m, 1H), 8.51-8.41 (m, 2H), 7.28-7.21 (m, 2H), 7.10-6.70 (m, 2H), 5.17-5.05 (m, 1H), 4.17-3.97 (m, 1H), 1.56-1.46 (m, 3H). LCMS ESI-MS m/z: =272 $[M+H]^+$.

Peak 6. $^1H$ NMR: (400 MHz, DMSO-$d_6$, ppm): δ 12.25-12.00 (m, 1H), 8.51-8.39 (m, 2H), 7.27-7.20 (m, 2H), 7.12-6.66 (m, 2H), 5.16-5.03 (m, 1H), 4.20-3.95 (m, 1H), 1.58-1.40 (m, 3H). LCMS ESI-MS m/z: =272 $[M+H]^+$.

The absolute stereochemistry was arbitrarily assigned.

Example 25: 3-Methyl-4-((2-(2,2,2-trifluoroethyl)-1H-imidazol-4-yl)methyl)pyridine

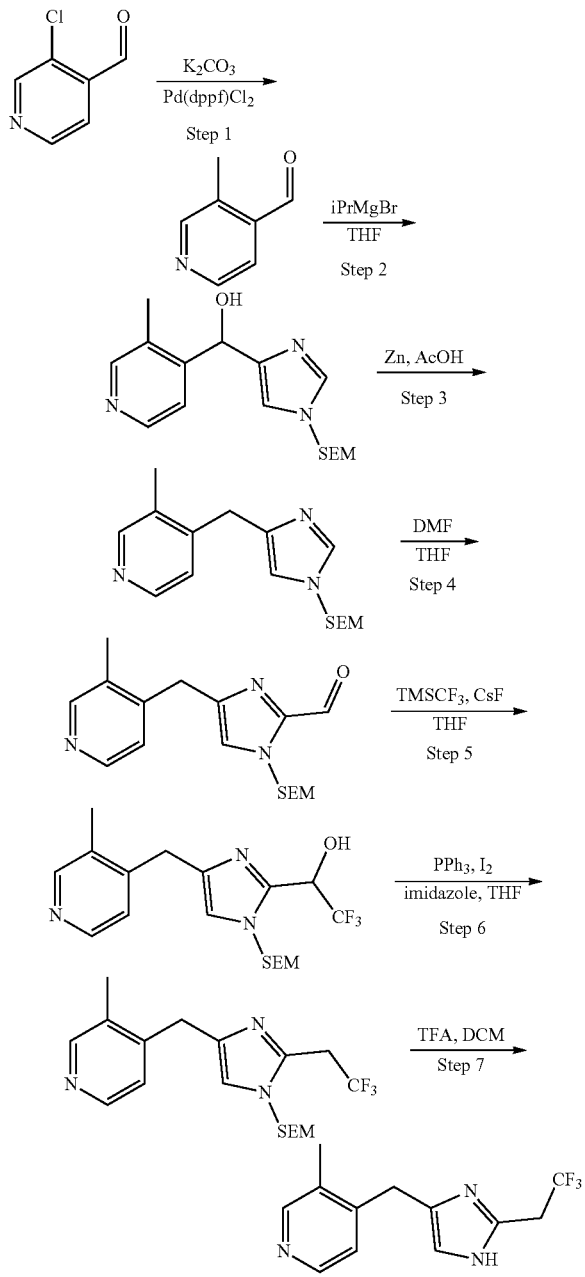

Step 1: 3-Methylisonicotinaldehyde. To a solution of 3-chloropyridine-4-carbaldehyde (7.0 g, 49.5 mmol) and trimethyl-1,3,5,2,4,6-trioxatriborinane (24.8 g, 98.9 mmol, 50% in THF) in dioxane (94.5 mL) and H$_2$O (10.5 mL) were added K$_2$CO$_3$ (13.7 g, 98.9 mmol) and Pd(dppf)Cl$_2$CH$_2$Cl$_2$ (2.0 g, 2.5 mmol). After stirring for 0.5 h at 100° C. under a nitrogen atmosphere, the precipitated solids were removed by filtration. The filtrate was concentrated under reduced pressure. The residue was purified by silica gel column to afford 3-methylisonicotinaldehyde (4.2 g, 70%) as a light-yellow oil. LCMS ESI-MS m/z: 122 [M+H]$^+$.

Step 2: (3-Methylpyridin-4-yl)(1-((2-(trimethylsilyl)ethoxy)methyl)-1H-imidazol-4-yl)methanol. A solution of 4-iodo-1-([2-(trimethylsilyl)ethoxy]methyl)imidazole (10.7 g, 33 mmol) in THF (107 mL) was treated with isopropylmagnesium bromide solution (39.6 mL, 39.6 mmol, 1 M solution in THF) for 20 min at 0° C. under nitrogen atmosphere. The resulted mixture was stirred for additional 0.5 h at 0° C. To the above mixture was added 3-methylisonicotinaldehyde (3.6 g, 29.7 mmol) dropwise over 10 min at 0° C. The resulted mixture was stirred for additional 1 h at 0° C. The reaction was quenched by saturated ammonium chloride solution (200 mL) at 0° C. The aqueous layer was extracted with EtOAc (3×100 mL) and dried over anhydrous Na$_2$SO$_4$. The solids were collected by filtration and the filter cake was rinsed with EtOAc (2×30 mL). The combined organic solutions were concentrated under reduced pressure. The residue was purified by silica gel chromatography to afford (3-methylpyridin-4-yl)(1-((2-(trimethylsilyl)ethoxy)methyl)-1H-imidazol-4-yl)methanol (6.6 g, 70%) as a light yellow oil. LCMS ESI-MS m/z: 320 [M+H]$^+$.

Step 3: 3-Methyl-4-((1-((2-(trimethylsilyl)ethoxy)methyl)-1H-imidazol-4-yl)methyl)pyridine. To a stirred solution of (3-methylpyridin-4-yl)(1-((2-(trimethylsilyl)ethoxy)methyl)-1H-imidazol-4-yl)methanol (6.95 g, 21.8 mmol) in acetic acid (70 mL) was added zinc (17.1 g, 261 mmol) at room temperature under nitrogen atmosphere. The resulted mixture was stirred for 2 h at 80° C. The precipitated solids were collected by filtration and the filter cake was rinsed with DCM (2×30 mL). The resulted organic solution was concentrated under reduced pressure. The residue was dissolved in DCM (30 mL). The organic layer was washed with saturated Na$_2$CO$_3$ (2×15 mL). The organic layer was dried over anhydrous MgSO$_4$, filtered, concentrated under reduced pressure, and purified by silica gel chromatography to afford 3-methyl-4-((1-((2-(trimethylsilyl)ethoxy)methyl)-1H-imidazol-4-yl)methyl)pyridine (4.7 g, 71%) as a light yellow oil. LCMS ESI-MS m/z: 304 [M+H]$^+$.

Step 4: 4-((3-Ethylpyridin-4-yl)methyl)-1-((2-(trimethylsilyl)ethoxy)methyl)-1H-imidazole-2-carbaldehyde. To a solution of 3-methyl-4-((1-((2-(trimethylsilyl)ethoxy)methyl)-1H-imidazol-4-yl)methyl)pyridine (4.70 g, 15.5 mmol) in THF (94 mL) was added LDA (23.2 mL, 46.5 mmol, 2 M solution in THF) dropwise at −78° C. The resulted mixture was stirred for 0.5 h at −78° C. To the above mixture was added dimethylformamide (2.26 g, 31.0 mmol) dropwise and then stirred for 0.5 h at −78° C. The reaction was quenched by saturated NH$_4$Cl solution (150 mL) at 0° C. The resulted mixture was extracted with EtOAc (2×50 mL). The combined organic layers were dried over anhydrous Na$_2$SO$_4$. The precipitated solids were extracted funnel with DCM (2×30 mL). The combined organic solutions were concentrated under reduced pressure and the residue was purified by silica gel chromatography to afford 4-((3-methylpyridin-4-yl)methyl)-1-((2-(trimethylsilyl)ethoxy)methyl)-1H-imidazole-2-carbaldehyde (3.45 g, 67%) as a light yellow oil. LCMS ESI-MS m/z: 332 [M+H]$^+$.

Step 5: 2,2,2-Trifluoro-1-(4-((3-methylpyridin-4-yl)methyl)-1-((2-(trimethylsilyl)ethoxy)methyl)-1H-imidazol-2-yl)ethan-1-ol. A solution of 4-((3-methylpyridin-4-yl)methyl)-1-((2-(trimethylsilyl)ethoxy)methyl)-1H-imidazole-2-carbaldehyde (3.15 g, 9.5 mmol) in tetrahydrofuran (60 mL) was treated with trifluoromethyltrimethylsilane (2.03 g, 14.3 mmol) at room temperature under nitrogen atmosphere followed by addition of cesium fluoride (2.17 g, 14.3 mmol) in portions at 0° C. The resulted mixture was stirred for additional 2 h at room temperature. The reaction mixture was concentrated under vacuum and the residue was purified by silica gel chromatography to afford 2,2,2-trifluoro-1-(4-((3-methylpyridin-4-yl)methyl)-1-((2-(trimethylsilyl)ethoxy)methyl)-1H-imidazol-2-yl)ethan-1-ol (3.26 g, 78%) as a light yellow solid. LCMS ESI-MS m/z: 402 [M+H]+.

Step 6: 3-Methyl-4-((2-(2,2,2-trifluoroethyl)-1-((2-(trimethylsilyl)ethoxy)methyl)-1H-imidazol-4-yl)methyl)pyridine. To a stirred solution of 2,2,2-trifluoro-1-(4-((3-methylpyridin-4-yl)methyl)-1-((2-(trimethylsilyl)ethoxy)methyl)-1H-imidazol-2-yl)ethan-1-ol (2.0 g, 4.98 mmol) in tetrahydrofuran (34 mL) was added triphenylphosphine (1.57 g, 5.98 mmol), imidazole (0.41 g, 5.98 mmol) and iodine (0.76 g, 2.99 mmol) at room temperature under nitrogen atmosphere. The resulted mixture was stirred for 1 h at 70° C. The reaction was quenched with saturated Na$_2$SO$_3$ solution at 0° C. The resulted mixture was extracted with EtOAc (2×15 mL). The precipitated solids were extracted with EtOAc (2×15 mL). The combined organic layers were dried over anhydrous Na$_2$SO$_4$, filtered, and concentrated under reduced pressure. The residue was purified by reverse phase chromatography to afford 3-methyl-4-((2-(2,2,2-trifluoroethyl)-1-((2-(trimethylsilyl)ethoxy)methyl)-1H-imidazol-4-yl)methyl)pyridine (1.46 g, 630%) as a light yellow oil. LCMS ESI-MS m/z: 386 [M+H]+.

Step 7: 3-Methyl-4-((2-(2,2,2-trifluoroethyl)-1H-imidazol-4-yl)methyl)pyridine. To a solution of 3-methyl-4-((2-(2,2,2-trifluoroethyl)-1-((2-(trimethylsilyl)ethoxy)methyl)-1H-imidazol-4-yl)methyl)pyridine (500 mg, 1.3 mmol) in DCM (2.5 mL) was added TFA (2.5 mL) dropwise at 0° C. under nitrogen atmosphere. The mixture was warmed to room temperature and stirred for 12 h. Upon completion, the reaction was concentrated under reduced pressure. The residue was basified to pH 7-8 with sat. NaHCO$_3$ (aq) and the organics were extracted with DCM (3×10 mL). The combined organic layers were dried over anhydrous MgSO$_4$, filtered, and concentrated under reduced pressure. The residue was purified by reverse phase chromatography to afford 3-methyl-4-((2-(2,2,2-trifluoroethyl)-1H-imidazol-4-yl)methyl)pyridine (190 mg, 57%) as an off-white solid. $^1$H NMR (400 MHz, DMSO-d$_6$, ppm): δ 11.98 (d, J=30.2 Hz, 1H), 8.36-8.24 (m, 2H), 7.06 (dd, J=24.3, 5.0 Hz, 1H), 6.86-6.57 (m, 1H), 3.84 (d, J=44.3 Hz, 2H), 3.65 (qd, J=11.1, 5.6 Hz, 2H), 2.26 (d, J=4.5 Hz, 3H). LCMS ESI-MS m/z: 256 [M+H]+.

Example 26 and 26a: (R)-2,2,2-Trifluoro-1-(4-(pyridin-4-ylmethyl)-1H-imidazol-2-yl)-1-(thiazol-5-yl)ethan-1-ol and (S)-2,2,2-Trifluoro-1-(4-(pyridin-4-ylmethyl)-1H-imidazol-2-yl)-1-(thiazol-5-yl)ethan-1-ol

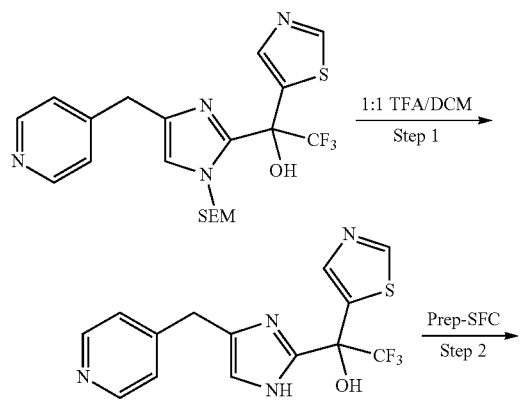

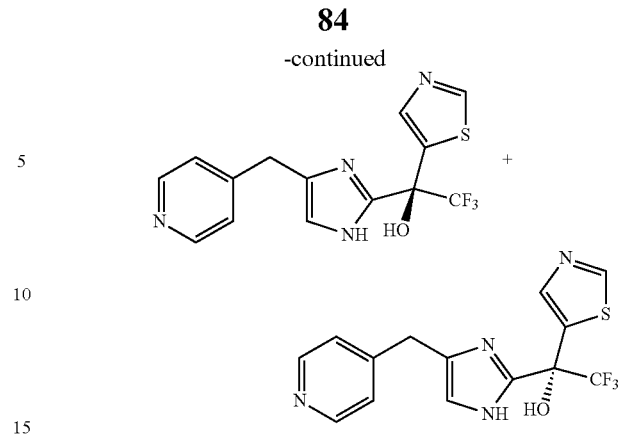

Step 1: 2,2,2-Trifluoro-1-(4-(pyridin-4-ylmethyl)-1H-imidazol-2-yl)-1-(thiazol-5-yl)ethan-1-ol. A solution of 2,2,2-trifluoro-1-[4-(pyridine-4-ylmethyl)-1-([2-(trimethylsilyl)ethoxy]methyl)imidazole-2-yl]-1-(1,3-thiazol-5-yl)ethanol (100 mg, 0.21 mmol) in DCM (1 mL) and TFA (1 mL) was stirred overnight at room temperature. The mixture was concentrated under reduced pressure and purified by reverse phase chromatography to afford 2,2,2-trifluoro-1-[4-(pyridine-4-ylmethyl)-1H-imidazol-2-yl]-1-1(1,3-thiazol-5-yl) ethanol (50 mg, 69%) as a yellow solid.

Step 2: (R)-2,2,2-Trifluoro-1-(4-(pyridin-4-ylmethyl)-1H-imidazol-2-yl)-1-(thiazol-5-yl)ethan-1-ol and (S)-2,2,2-Trifluoro-1-(4-(pyridin-4-ylmethyl)-1H-imidazol-2-yl)-1-(thiazol-5-yl)ethan-1-ol. The racemic mixture (50 mg) was separated by prep-SFC. Peak 1 was collected as a white solid (4.6 mg, 9%) and Peak 2 was collected as white solids (7.4 mg, 14%).

Peak 1. $^1$H NMR (400 MHz, DMSO-d$_6$, ppm): δ 12.41 (s, 1H), 9.14 (d, J=1.8 Hz, 1H), 8.65-8.27 (m, 2H), 8.09 (d, J=2.3 Hz, 1H), 7.27 (d, J=5.0 Hz, 2H), 6.92 (s, 2H), 3.91 (s, 2H). LCMS ESI-MS m/z: 341 [M+H]+.

Peak 2. $^1$H NMR (400 MHz, DMSO-d$_6$, ppm): δ 12.40 (d, J=66.4 Hz, 1H), 9.14 (s, 1H), 8.46 (ddd, J=9.2, 4.4, 1.6 Hz, 2H), 8.27 (d, J=10.0 Hz, 1H), 8.08 (s, 1H), 7.38-7.15 (m, 2H), 6.86 (d, J=73.0 Hz, 1H), 3.91 (d, J=27.0 Hz, 2H). LCMS ESI-MS m/z: 341 [M+H]+.

The absolute stereochemistry was arbitrarily assigned and rotamers are observed.

Example 27: 3-Chloro-4-((2-(2,2,2-trifluoroethyl)-1H-imidazol-4-yl)methyl)pyridine

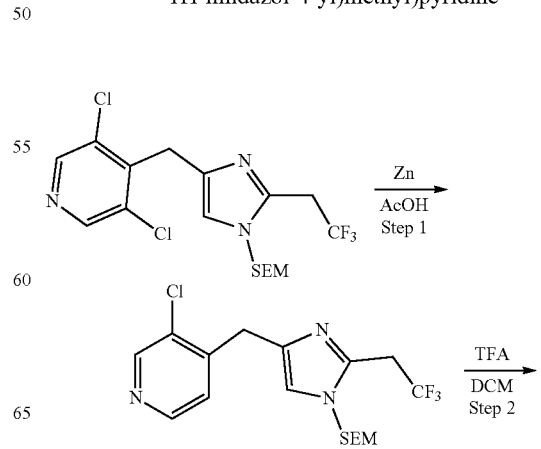

-continued

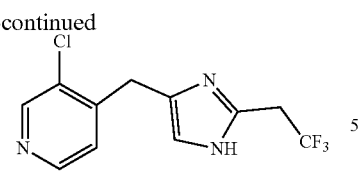

Step 1: 3-Chloro-4-((2-(2,2,2-trifluoroethyl)-1-((2-(trimethylsilyl)ethoxy)methyl)-1H-imidazol-4-yl)methyl)pyridine. To a stirred solution of 3,5-dichloro-4-((2-(2,2,2-trifluoroethyl)-1-((2-(trimethylsilyl)ethoxy)methyl)-1H-imidazol-4-yl)methyl)pyridine (1 g, 2.2 mmol, Example 22, step 5) in AcOH (10 mL) was treated with zinc (1.78 g, 27.2 mmol) at 25° C. under nitrogen atmosphere. The resulting mixture was stirred for 12 h at 80° C. The resulting mixture was allowed to cool down to room temperature and the solids were removed by filtration and the filter cake was rinsed with AcOH (2×5 mL). To the resulting mixture was added zinc (1.78 g, 27.2 mmol) at 25° C. The resulting mixture was stirred for additional 12 h at 80° C. Repeated this operation (filter and add zinc) for additional 2 times. The solids were removed by filtration and the filter cake was rinsed with DCM (2×30 mL). The resulting organic solution was concentrated under reduced pressure to yield a light brown oil. The crude product (2.2 g) was used in the next step directly without further purification. LCMS ESI-MS m/z: =406 [M+H]$^+$.

Step 2: 3-Chloro-4-((2-(2,2,2-trifluoroethyl)-1H-imidazol-4-yl)methyl)pyridine. To a stirred solution of 3-chloro-4-((2-(2,2,2-trifluoroethyl)-1-((2-(trimethylsilyl)ethoxy)methyl)-1H-imidazol-4-yl)methyl)pyridine (2.2 g, 1.3 mmol) in DCM (11 mL) was added TFA (11 mL) dropwise at 0° C. under nitrogen atmosphere. The resulting mixture was stirred for 12 h at 25° C. The resulting mixture was concentrated under reduced pressure. The residue was dissolved in DCM (10 mL) and H$_2$O (10 mL), the mixture was basified to pH 8-9 with sat. NaHCO$_3$. The resulting mixture was extracted with DCM (3×30 mL). The organic layers dried over anhydrous MgSO$_4$. The solids were removed by filtration and the filter cake was rinsed in the funnel with DCM (2×20 mL). The resulting organic solution was concentrated under reduced pressure. The residue was purified by reverse phase flash chromatography to afford 3-chloro-4-((2-(2,2,2-trifluoroethyl)-1H-imidazol-4-yl)methyl)pyridine (120 mg, 19% over 2 steps) as an off-white solid. $^1$H NMR (400 MHz, DMSO-d$_6$, ppm): δ 8.58 (d, J=16.1 Hz, 1H), 8.49-8.38 (m, 1H), 7.31 (d, J=4.9 Hz, 1H), 6.92 (s, 1H), 3.99 (d, J=43.4 Hz, 2H), 3.67 (q, J=11.1 Hz, 2H). LCMS ESI-MS m/z: =276 [M+H]$^+$.

Example 28: 2-Chloro-4-((2-(2,2,2-trifluoroethyl)-1H-imidazol-4-yl)methyl)pyridine

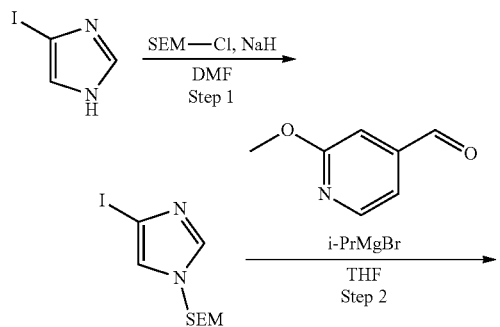

-continued

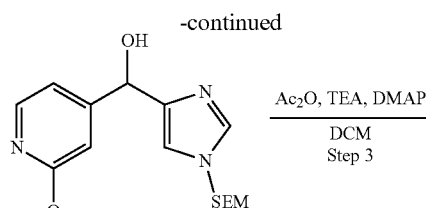

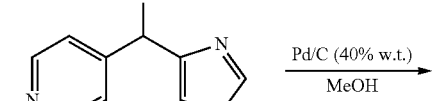

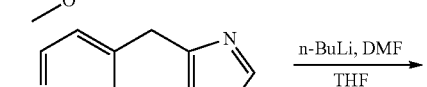

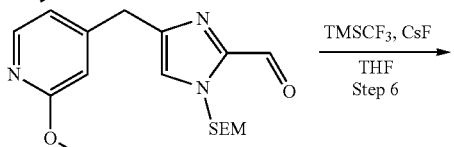

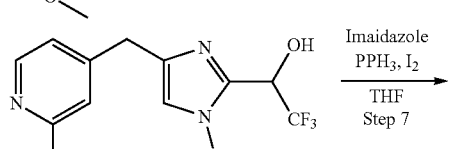

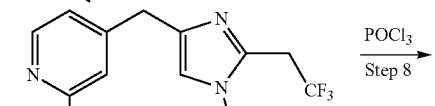

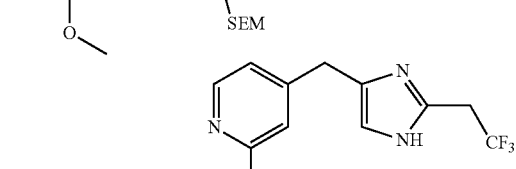

Step 1: 4-Iodo-1-((2-(trimethylsilyl)ethoxy)methyl)imidazole. A solution of 4-iodo-1H-imidazole (20 g, 103.1 mmol) in DMF (200 mL) was treated with NaH (60%, 3 g, 124 mmol) for 1 h at 0° C. under a nitrogen atmosphere followed by the addition of SEM-Cl (20.6 g, 124 mmol) dropwise at 0° C. The resulting mixture was stirred overnight at room temperature under a nitrogen atmosphere. The reaction was quenched by the addition of water/ice (600 mL) at 0° C. The aqueous layer was extracted with EtOAc (3×200 mL). The organic layers were combined and washed with brine (1×200 mL), dried over anhydrous Na$_2$SO$_4$. The resulting mixture was filtered, and concentrated under reduced pressure. The residue was purified by silica gel column chromatography, eluted with PE/EA (10:1) to afford 4-iodo-1-((2-(trimethylsilyl)ethoxy)methyl)imidazole (25 g, 75%) as a yellow oil. LCMS ESI-MS m/z: 325 [M+H]$^+$.

Step 2: (2-Methoxypyridin-4-yl)(1-((2-(trimethylsilyl)ethoxy)methyl)imidazol-4-yl)methanol. A solution of 4-iodo-1-((2-(trimethylsilyl)ethoxy)methyl)imidazole (10 g, 30.8 mmol) in THF (60 mL) was treated with bromo (propan-2-yl)magnesium (33.7 mL, 33.6 mmol, 1 M) for 1 h at −10° C. under a nitrogen atmosphere followed by the addition of 2-methoxypyridine-4-carbaldehyde (3.9 g, 28 mmol) dropwise at −10° C. The resulting mixture was stirred for 2 h at room temperature under a nitrogen atmosphere. The resulting mixture was diluted with EtOAc (30 mL). The reaction was quenched by the addition of $Na_2SO_4 \cdot 10H_2O$ (10 g) at room temperature. The precipitated solids were filtered, and the filter cake was rinsed with EtOAc (2×20 mL). The ethyl acetate washes were collected and concentrated under reduced pressure. The residue was purified by silica gel column chromatography to afford (2-methoxypyridin-4-yl)(1-((2-(trimethylsilyl)ethoxy)methyl)imidazol-4-yl)methanol (5 g, 53%) as a yellow oil. LCMS ESI-MS m/z: 336 [M+H]$^+$.

Step 3: (2-Methoxypyridin-4-yl)(1-((2-(trimethylsilyl)ethoxy)methyl)imidazol-4-yl)methyl acetate. A solution of (2-methoxypyridin-4-yl)(1-((2-(trimethylsilyl)ethoxy)methyl)imidazol-4-yl)methanol (4.5 g, 13.4 mmol) in DCM (90 mL) was treated with TEA (2.7 g, 26.8 mmol), DMAP (0.2 g, 1.3 mmol), $Ac_2O$ (1.4 g, 13.4 mmol) for 1 h at room temperature under a nitrogen atmosphere. The resulting mixture was washed with 30 mL of water. The resulting mixture was concentrated under reduced pressure. The residue was purified by reverse phase flash chromatography to afford (2-methoxypyridin-4-yl)(1-((2-(trimethylsilyl)ethoxy)methyl)imidazol-4-yl)methyl acetate (4.8 g, 95%) as a yellow oil. LCMS ESI-MS m/z: 377 [M+H]$^+$.

Step 4: 2-Methoxy-4-((1-((2-(trimethylsilyl)ethoxy) methyl)imidazol-4-yl)methyl)pyridine. A mixture of (2-methoxypyridin-4-yl)(1-((2-(trimethylsilyl)ethoxy) methyl)imidazol-4-yl)methyl acetate (4.8 g, 12.7 mmol) and Pd/C (2.4 g, 22.5 mmol) in MeOH (95 mL) was stirred overnight at room temperature under a hydrogen atmosphere. The resulting mixture was filtered, and the filter cake was washed with EtOAc (2×30 mL). The filtrate was concentrated under reduced pressure. The residue was purified by reverse phase flash chromatography to afford 2-methoxy-4-((1-((2-(trimethylsilyl)ethoxy)methyl)imidazol-4-yl) methyl)pyridine (3.5 g, 86%) as a yellow oil. LCMS ESI-MS m/z: 320 [M+H]$^+$.

Step 5: 4-((2-Methoxypyridin-4-yl)methyl]-1-((2-(trimethylsilyl)ethoxy]methyl) imidazole-2-carbaldehyde. A solution of 22-methoxy-4-((1-((2-(trimethylsilyl)ethoxy) methyl)imidazol-4-yl)methyl)pyridine (3 g, 9.4 mmol) in THF (60 mL) was treated with n-BuLi (7.5 mL, 18.8 mmol, 2.5 M) for 2 h at −78° C. under a nitrogen atmosphere followed by the addition of DMF (1.4 g, 18.8 mmol) dropwise at −78° C. The reaction was quenched by the addition of water/ice (20 mL) at −20° C. The aqueous layer was extracted with EtOAc (3×20 mL). The organic layer was combined and concentrated under reduced pressure. The residue was purified by reverse phase flash chromatography to afford 5-((2-methoxypyridin-4-yl)methyl]-1-((2-(trimethylsilyl)ethoxy]methyl)imidazole-2-carbaldehyde (2.2 g, 67%) as a yellow oil. LCMS ESI-MS m/z: 348 [M+H]$^+$.

Step 6: 2,2,2-Trifluoro-1-(4-((2-methoxypyridin-4-yl) methyl]-1-((2-(trimethylsilyl)ethoxy]methyl)imidazol-2-yl) ethanol. A solution of 5-((2-methoxypyridin-4-yl)methyl]-1-((2-(trimethylsilyl)ethoxy]methyl)imidazole-2-carbaldehyde (2 g, 5.8 mmol) in THF (40 mL) was treated with $TMSCF_3$ (1 g, 6.9 mmol) for 5 min at 0° C. under a nitrogen atmosphere followed by the addition of CsF (1.1 g, 6.9 mmol) in portions at 0° C. The resulting mixture was stirred overnight at room temperature under a nitrogen atmosphere. The resulting mixture was concentrated under reduced pressure. The residue was purified by reverse phase flash chromatography to afford 2,2,2-trifluoro-1-(5-((2-methoxypyridin-4-yl)methyl]-1-((2-(trimethylsilyl)ethoxy] methyl)imidazol-2-yl)ethanol (2.1 g, 87%) as a yellow oil. LCMS ESI-MS m/z: 418 [M+H]$^+$.

Step 7: 2-Methoxy-4-((2-(2,2,2-trifluoroethyl)-1-((2-(trimethylsilyl)ethoxy]methyl)imidazol-4-yl]methyl)pyridine. A solution of 2,2,2-trifluoro-1-(5-((2-methoxypyridin-4-yl)methyl]-1-((2-(trimethylsilyl)ethoxy]methyl)imidazol-2-yl)ethanol (1.9 g, 4.6 mmol) in THF (19 mL) was treated with imidazole (0.3 g, 4.6 mmol), $PPh_3$ (1.4 g, 5.5 mmol), $I_2$ (0.7 g, 2.7 mmol) overnight at 65° C. under a nitrogen atmosphere. The resulting mixture was concentrated under reduced pressure. The residue was purified by reverse phase flash chromatography to afford 2-methoxy-4-((2-(2,2,2-trifluoroethyl)-3-((2-(trimethylsilyl)ethoxy]methyl)imidazol-4-yl]methyl)pyridine (1.2 g, 66%) as a yellow oil. LCMS ESI-MS m/z: 402 [M+H]$^+$.

Step 8: 2-Chloro-4-((2-(2,2,2-trifluoroethyl)-1H-imidazol-4-yl)methyl)pyridine. A solution of 2-methoxy-4-((2-(2, 2,2-trifluoroethyl)-3-((2-(trimethylsilyl)ethoxy]methyl)imidazol-4-yl]methyl)pyridine (0.3 g, 0.7 mmol) in $POCl_3$ (6 mL) was stirred overnight at 100° C. under a nitrogen atmosphere. The resulting mixture was concentrated under reduced pressure. The residue was basified to pH 7 with NaOH aqueous solution (1 M). The resulting mixture was concentrated under reduced pressure. The residue was purified by reverse phase flash chromatography to afford crude product as a white solid. The crude product was further purified by prep-HPLC to afford 2-chloro-4-((2-(2, 2,2-trifluoroethyl)-3H-imidazol-4-yl]methyl)pyridine (75 mg, 36%) as a white solid. $^1$H NMR (400 MHz, Methanol-$d_4$, ppm): δ 8.26 (d, J=5.2 Hz, 1H), 7.34 (d, J=1.3 Hz, 1H), 7.26 (dd, J=5.2, 1.5 Hz, 1H), 6.97 (s, 1H), 3.98 (s, 2H), 3.64 (q, J=10.6 Hz, 2H). LCMS ESI-MS m/z: 276 [M+H]$^+$.

Example 29: 2-Fluoro-4-((2-(2,2,2-trifluoroethyl)-3H-imidazol-4-yl)methyl)pyridine

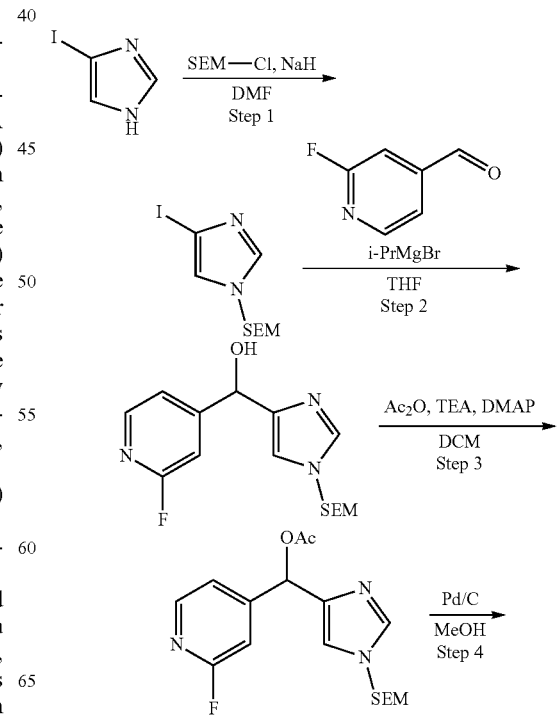

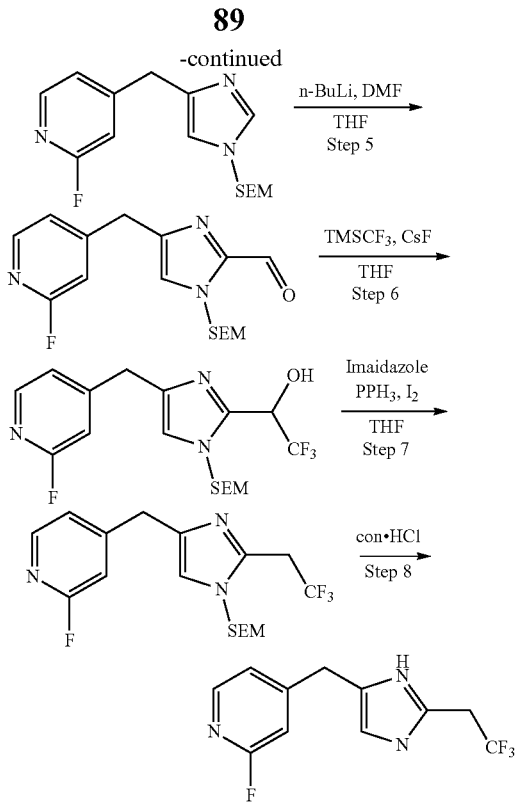

Step 1: 4-Iodo-1-((2-(trimethylsilyl)ethoxy]methyl)imidazole. A solution of 4-iodo-1H-imidazole (20 g, 103 mmol) in DMF (200 mL) was treated with NaH (60%, 3 g, 124 mmol) for 1 h at 0° C. under a nitrogen atmosphere followed by the addition of SEM-Cl (20.6 g, 124 mmol) dropwise at 0° C. The resulting mixture was stirred overnight at room temperature under a nitrogen atmosphere. The reaction was quenched by the addition of water/ice (600 mL) at 0° C. The aqueous layer was extracted with EtOAc (3×200 mL). The organic layers were combined and washed with brine (1×200 mL), dried over anhydrous $Na_2SO_4$. The resulting mixture was concentrated under reduced pressure. The residue was purified by silica gel column chromatography to afford 4-iodo-1-((2-(trimethylsilyl)ethoxy]methyl)imidazole (25 g, 75%) as a yellow oil. LCMS ESI-MS m/z: 325 [M+H]$^+$.

Step 2: (2-Fluoropyridin-4-yl)(1-((2-(trimethylsilyl) ethoxy]methyl)imidazol-4-yl)methanol. A solution of 4-iodo-1-((2-(trimethylsilyl)ethoxy]methyl)imidazole (5 g, 15.4 mmol) in THF (30 mL) was treated with i-PrMgBr (18.5 mL, 18.5 mmol, 1 M) for 1 h at −10° C. under a nitrogen atmosphere followed by the addition of 2-fluoropyridine-4-carbaldehyde (1.9 g, 15.4 mmol) dropwise at −10° C. The resulting mixture was stirred for 2 h at room temperature under a nitrogen atmosphere. The reaction was quenched by the addition of $Na_2SO_4 \cdot 10H_2O$ (5 g) solid at room temperature. The resulting mixture was filtered, and the filter cake was rinsed in the funnel with EtOAc (2×20 mL). The filtrate was collected and concentrated under reduced pressure. The residue was purified by reverse flash chromatography to afford (2-fluoropyridin-4-yl)(1-((2-(trimethylsilyl) ethoxy]methyl)imidazol-4-yl)methanol (3.5 g, 70%) as a brown oil. LCMS ESI-MS m/z: 324 [M+H]$^+$.

Step 3: (2-Fluoropyridin-4-yl) (1-((2-(trimethylsilyl) ethoxy]methyl)imidazol-4-yl)methyl acetate. To a stirred solution of (2-fluoropyridin-4-yl)(1-((2-(trimethylsilyl) ethoxy]methyl)imidazol-4-yl)methanol (3.3 g, 10.2 mmol) in DCM (66 mL) was added TEA (2.1 g, 20.4 mmol), DMAP (0.12 g, 1 mmol), $Ac_2O$ (1 g, 10.2 mmol) at room temperature under a nitrogen atmosphere. The resulting mixture was stirred for 1 h at room temperature under nitrogen atmosphere. The resulting mixture was concentrated under reduced pressure. The resulting mixture was diluted with EtOAc (30 mL). The resulting mixture was washed with of water (2×20 mL) and brine (20 mL). The resulting mixture was concentrated under reduced pressure. The residue was purified by reverse flash chromatography to afford (2-fluoropyridin-4-yl)(1-((2-(trimethylsilyl) ethoxy] methyl)imidazol-4-yl)methyl acetate (3.5 g, 85%) as a yellow oil. LCMS ESI-MS m/z: 366 [M+H]$^+$.

Step 4: 2-Fluoro-4-((1-((2-(trimethylsilyl)ethoxy]methyl) imidazol-4-yl)methyl]pyridine. A mixture of (2-fluoropyridin-4-yl)(1-((2-(trimethylsilyl)ethoxy]methyl)imidazol-4-yl)methyl acetate (3.5 g, 9.1 mmol) and Pd/C (1.7 g, 15.6 mmol) in MeOH (70 mL) was stirred overnight at room temperature under a hydrogen atmosphere. The resulting mixture was filtered, and the filter cake was washed with EtOAc (2×20 mL). The filtrate was collected and concentrated under reduced pressure. The residue was purified by silica gel column chromatography to afford 2-fluoro-4-((1-((2-(trimethylsilyl)ethoxy]methyl)imidazol-4-yl)methyl] pyridine (2.7 g, 97%) as a yellow oil. LCMS ESI-MS m/z: 308 [M+H]$^+$.

Step 5: 4-((2-Fluoropyridin-4-yl)methyl]-1-((2-(trimethylsilyl)ethoxy]methyl)imidazole-2-carbaldehyde. A solution of 2-fluoro-4-((1-((2-(trimethylsilyl)ethoxy]methyl)imidazol-4-yl)methyl]pyridine (2.7 g, 8.8 mmol) in THF (54 mL) was treated with n-BuLi (7 mL, 17.6 mmol, 2.5 M) for 2 h at −78° C. under a nitrogen atmosphere followed by the addition of DMF (1.3 g, 17.6 mmol) dropwise at −78° C. The resulting mixture was stirred for 30 min at −78° C. under a nitrogen atmosphere. The reaction was quenched by the addition of water/ice (10 mL) at −20° C. The aqueous layer was extracted with EtOAc (3×20 mL). The resulting mixture was concentrated under reduced pressure. The residue was purified by reverse flash chromatography to afford 4-((2-fluoropyridin-4-yl)methyl]-1-((2-(trimethylsilyl) ethoxy]methyl)imidazole-2-carbaldehyde (1.5 g, 51%) as a yellow oil. LCMS ESI-MS m/z: 336 [M+H]$^+$.

Step 6: 2,2,2-Trifluoro-1-(4-((2-fluoropyridin-4-yl) methyl]-1-((2-(trimethylsilyl)ethoxy]methyl)imidazol-2-yl) ethanol. A solution of 4-((2-fluoropyridin-4-yl)methyl]-1-((2-(trimethylsilyl)ethoxy]methyl)imidazole-2-carbaldehyde (1.4 g, 4.2 mmol) in THF (28 mL) was treated with $TMSCF_3$ (0.7 g, 5 mmol) for 5 min at 0° C. under a nitrogen atmosphere followed by the addition of CsF (0.8 g, 5 mmol) in portions at 0° C. The resulting mixture was stirred at room temperature under a nitrogen atmosphere. The resulting mixture was concentrated under reduced pressure. The residue was purified by reverse flash chromatography to afford 2,2,2-trifluoro-1-(4-((2-fluoropyridin-4-yl)methyl)-1-((2-(trimethylsilyl)ethoxy]methyl) imidazol-2-yl)ethanol (1.4 g, 83%) as a yellow oil. LCMS ESI-MS m/z: 406 [M+H]$^+$.

Step 7: 2-Fluoro-4-((2-(2,2,2-trifluoroethyl)-3-((2-(trimethylsilyl)ethoxy]methyl)imidazol-4-yl)methyl)pyridine. A solution of 2,2,2-trifluoro-1-(4-((2-fluoropyridin-4-yl) methyl]-1-((2-(trimethylsilyl)ethoxy]methyl)imidazol-2-yl) ethanol (400 mg, 1 mmol) in THF (4 mL) was treated with imidazole (67.2 mg, 1 mmol), $PPh_3$ (310 mg, 1.2 mmol), and $I_2$ (150 mg, 0.6 mmol) overnight at 65° C. under a nitrogen atmosphere. The resulting mixture was diluted with EtOAc (10 mL). The reaction was quenched by the addition of Na₂S₂O₃ (aq., 10 mL) at room temperature. The aqueous layer was extracted with EtOAc (2×10 mL). The resulting mixture was concentrated under reduced pressure. The residue was purified by reverse flash chromatography to afford 2-fluoro-4-((2-(2,2,2-trifluoroethyl)-3-((2-(trimethylsilyl)ethoxy]methyl)imidazol-4-yl]methyl)pyridine (300 mg, 78%) as a light yellow oil. LCMS ESI-MS m/z: 390 [M+H]⁺.

Step 8: 2-Fluoro-4-((2-(2,2,2-trifluoroethyl)-3H-imidazol-4-yl)methyl)pyridine. A solution of 2-fluoro-4-((2-(2,2,2-trifluoroethyl)-3-((2-(trimethylsilyl)ethoxy]methyl)imidazol-4-yl]methyl)pyridine (240 mg, 0.6 mmol) in DCM (4.8 mL) was treated with CF₃COOH (4.8 mL) overnight at room temperature under a nitrogen atmosphere. The resulting mixture was concentrated under reduced pressure. The residue was dissolved in MeOH (3 mL). The reaction was quenched by the addition of ethylenediamine (1 mL) at room temperature. The resulting mixture was concentrated under reduced pressure. The residue was purified by reverse phase flash chromatography to afford crude material as a white solid. The crude material was further purified by prep-HPLC to afford 2-fluoro-4-((2-(2,2,2-trifluoroethyl)-3H-imidazol-4-yl)methyl)pyridine (146 mg, 92%) as a white solid. ¹H NMR (400 MHz, Methanol-d₄, ppm): δ 8.10 (d, J=5.2 Hz, 1H), 7.20 (dt, J=5.3, 1.8 Hz, 1H), 6.95 (d, J=12.4 Hz, 2H), 4.02 (s, 2H), 3.63 (q, J=10.6 Hz, 2H). LCMS ESI-MS m/z: 260 [M+H]⁺.

Example 30 and 30a: (S)-(5-((3-Methylpyridin-4-yl)methyl)-1H-imidazol-2-yl)(thiazol-5-yl)methanol and (R)-(5-((3-methylpyridin-4-yl)methyl)-1H-imidazol-2-yl)(thiazol-5-yl)methanol

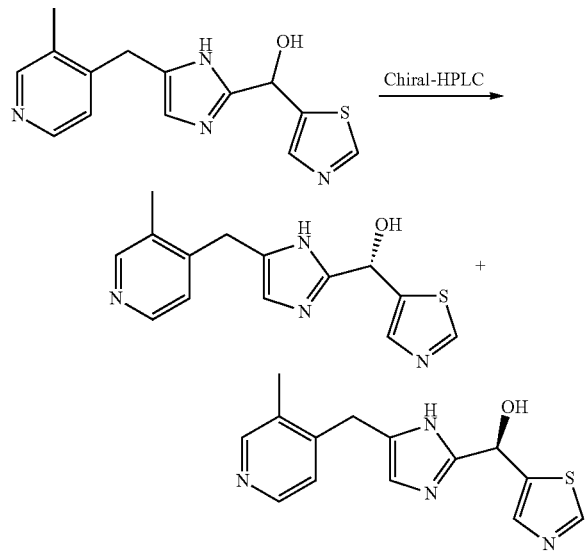

rac-(5-((3-Methylpyridin-4-yl)methyl)-1H-imidazol-2-yl)(thiazol-5-yl)methanol (96.6 mg, Example 21) was separated by prep-Chiral-HPLC to afford Peak 1 (22.3 mg, 23%) as a light yellow solid and Peak 2 (24.3 mg, 25%) as a light yellow solid.

Peak 1. ¹H NMR (400 MHz, DMSO-d₆, ppm): δ 11.95 (d, J=57.8 Hz, 1H), 8.99 (d, J=0.8 Hz, 1H), 8.34-8.23 (m, 2H), 7.73 (s, 1H), 7.09 (d, J=5.0 Hz, 1H), 6.81-6.44 (m, 2H), 6.01 (dd, J=4.6, 1.0 Hz, 1H), 3.82 (d, J=42.2 Hz, 2H), 2.27 (s, 3H). LCMS ESI-MS m/z: =287 [M+H]⁺.

Peak 2. ¹H NMR (400 MHz, DMSO-d₆, ppm): δ 11.98 (d, J=59.6 Hz, 1H), 8.99 (s, 1H), 8.31-8.23 (m, 2H), 7.73 (s, 1H), 7.09 (d, J=5.1 Hz, 1H), 6.81-6.48 (m, 2H), 6.01 (s, 1H), 3.82 (d, J=41.6 Hz, 2H), 2.27 (s, 3H). LCMS ESI-MS m/z: =287 [M+H]⁺.

The absolute stereochemistry was arbitrarily assigned.

Example 31 and 31a: (R)-(5-(pyridin-4-ylmethyl)-1H-imidazol-2-yl)(thiazol-2-yl)methanol and (S)-(5-(pyridin-4-ylmethyl)-1H-imidazol-2-yl)(thiazol-2-yl)methanol

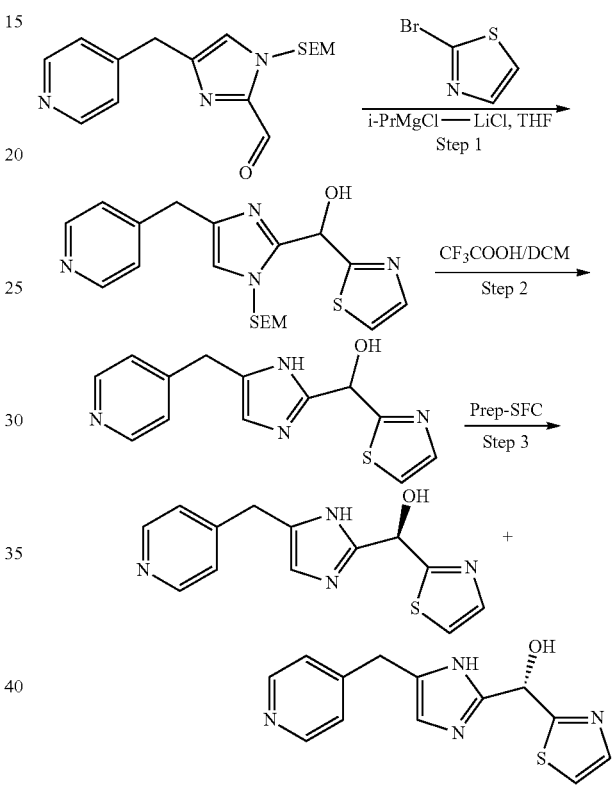

Step 1: (5-(Pyridin-4-ylmethyl)-1-((2-(trimethylsilyl)ethoxy]methyl)imidazol-2-yl](1,3-thiazol-2-yl)methanol.

To a stirred solution of 2-bromothiazole (248 mg, 1.51 mmol) in THF (8 mL) was added i-PrMgCl—LiCl (1.3 M in THF) (1.16 mL, 1.51 mmol) dropwise at 0° C. under a nitrogen atmosphere. The resulting mixture was stirred for 30 min at room temperature. To the above mixture was added 4-(pyridin-4-ylmethyl)-1-((2-(trimethylsilyl)ethoxy)methyl)-1H-imidazole-2-carbaldehyde (400 mg, 1.26 mmol, Example 3, step 4) dropwise at 0° C. The resulting mixture was stirred for additional 1 h at room temperature. The reaction was quenched by the addition of sat. NH₄Cl (aq) (20 mL) at 0° C. The resulting mixture was extracted with EtOAc (2×20 mL). The combined organic layers were washed with brine (1×20 mL), dried over anhydrous Na₂SO₄. After filtration, the filtrate was concentrated under reduced pressure to yield crude product as yellow oil. The crude product was purified by reverse phase flash chromatography to afford (4-(pyridin-4-ylmethyl)-1-((2-(trimethylsilyl)ethoxy)methyl)-1H-imidazol-2-yl)(thiazol-2-yl)methanol (200 mg, 39%) as a yellow solid. LCMS ESI-MS m/z: 403 [M+H]⁺.

Step 2: (5-(pyridin-4-ylmethyl)-1H-imidazol-2-yl)(thiazol-2-yl)methanol. A solution of (4-(pyridin-4-ylmethyl)-1-((2-(trimethylsilyl)ethoxy)methyl)-1H-imidazol-2-yl)(thiazol-2-yl)methanol (200 mg, 0.5 mmol) in DCM (2 mL) and CF$_3$COOH (2 mL) was stirred overnight at room temperature under a nitrogen atmosphere. The resulting mixture was concentrated under reduced pressure. The residue was dissolved in MeOH (2 mL) and quenched with ethylenediamine (1 mL). The resulting mixture was purified by prep-HPLC to (5-(pyridin-4-ylmethyl)-1H-imidazol-2-yl)(thiazol-2-yl)methanol (80 mg, 59%) as a white solid. LCMS ESI-MS m/z: 273 [M+H]$^+$.

Step 3: (R)-(5-(Pyridin-4-ylmethyl)-1H-imidazol-2-yl)(thiazol-2-yl)methanol and (S)-(5-(pyridin-4-ylmethyl)-1H-imidazol-2-yl)(thiazol-2-yl)methanol. rac-(5-(pyridin-4-ylmethyl)-1H-imidazol-2-yl)(thiazol-2-yl)methanol mixture (80 mg) was purified by prep-SFC to afford Peak 1 (14.4 mg, 18%) as a white solid and Peak 2 (16.7 mg, 21%) as a white solid.

Peak 1. $^1$H NMR (400 MHz, DMSO-d$_6$, ppm) δ 11.93 (s, 1H), 8.53-8.24 (m, 2H), 7.80-7.49 (m, 2H), 7.37-7.06 (m, 2H), 6.94-6.60 (m, 2H), 5.91 (d, J=4.6 Hz, 1H), 3.82 (s, 2H). LCMS ESI-MS m/z: 273 [M+H]$^+$.

Peak 2. $^1$H NMR (400 MHz, DMSO-d$_6$, ppm): δ 11.97 (d, J=65.9 Hz, 1H), 8.43 (d, J=5.3 Hz, 2H), 7.80-7.64 (m, 2H), 7.24 (d, J=5.6 Hz, 2H), 7.04-6.44 (m, 2H), 5.91 (d, J=4.7 Hz, 1H), 3.84 (d, J=41.5 Hz, 2H). LCMS ESI-MS m/z: 273 [M+H]$^+$.

The absolute stereochemistry was arbitrarily assigned.

Example 32 and 32a: (R)-1,1,1-Trifluoro-2-(5-(pyridin-4-ylmethyl)-1H-imidazol-2-yl)propan-2-ol and (S)-1,1,1-trifluoro-2-(5-(pyridin-4-ylmethyl)-1H-imidazol-2-yl)propan-2-ol

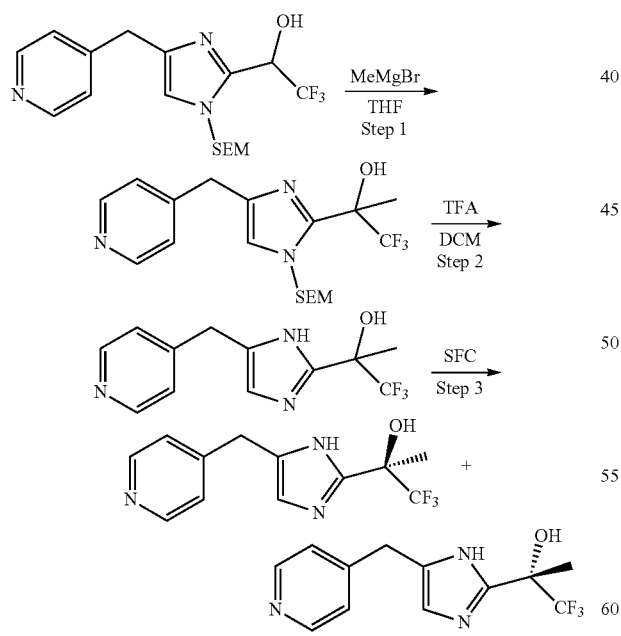

Step 1: 1,1,1-Trifluoro-2-(4-(pyridin-4-ylmethyl)-1-((2-(trimethylsilyl)ethoxy)methyl)-1H-imidazol-2-yl)propan-2-ol. To a stirred solution of 2,2,2-trifluoro-1-(4-(pyridin-4-ylmethyl)-1-((2-(trimethylsilyl)ethoxy)methyl)-1H-imidazol-2-yl)ethan-1-one (600 mg, 1.55 mmol, Example 12, step 1) in THF (6 mL) was added bromo(methyl)magnesium (1M in THF, 0.75 mL, 1.86 mmol) dropwise at −78° C. under a nitrogen atmosphere. The resulting mixture was stirred for 2 h at 0° C. under a nitrogen atmosphere. The reaction was quenched with water/ice (20 mL) at 0° C. The resulting mixture was extracted with EtOAc (3×10 mL). The combined organic layers were washed with brine (1×50 mL), dried over anhydrous Na$_2$SO$_4$. After filtration, the filtrate was concentrated under reduced pressure to afford 1,1,1-trifluoro-2-(4-(pyridin-4-ylmethyl)-1-((2-(trimethylsilyl)ethoxy)methyl)-1H-imidazol-2-yl)propan-2-ol (500 mg, 80%) as a brown oil. LCMS ESI-MS m/z: 402 [M+H]$^+$.

Step 2: 1,1,1-Trifluoro-2-(5-(pyridin-4-ylmethyl)-1H-imidazol-2-yl)propan-2-ol. To a stirred solution of 1,1,1-trifluoro-2-(4-(pyridin-4-ylmethyl)-1-((2-(trimethylsilyl)ethoxy)methyl)-1H-imidazol-2-yl)propan-2-ol (500 mg, 1.24 mmol) in DCM (2.5 mL) was added TFA (2.5 mL) dropwise at 0° C. under a nitrogen atmosphere. The resulting mixture was stirred overnight at room temperature under a nitrogen atmosphere. The resulting mixture was concentrated under reduced pressure to yield a yellow solid. The crude product (300 mg) was dissolved in 2 mL MeOH and quenched with 1 mL ethylenediamine. The resulting mixture was purified by prep-HPLC to afford 1,1,1-trifluoro-2-(5-(pyridin-4-ylmethyl)-1H-imidazol-2-yl)propan-2-ol (65 mg, 19%) as a white solid. LCMS ESI-MS m/z: 272 [M+H]$^+$.

Step 3: (R)-1,1,1-Trifluoro-2-(5-(pyridin-4-ylmethyl)-1H-imidazol-2-yl)propan-2-ol and (S)-1,1,1-trifluoro-2-(5-(pyridin-4-ylmethyl)-1H-imidazol-2-yl)propan-2-ol. rac-1,1,1-Trifluoro-2-(5-(pyridin-4-ylmethyl)-1H-imidazol-2-yl)propan-2-ol (65 mg) was purified by SFC to afford Peak 1 (6 mg, 9.2%) as a white solid and Peak 2 (7.9 mg, 12%) as a white solid.

Peak 1. $^1$H NMR (400 MHz, DMSO-d$_6$, ppm) δ 8.47-8.41 (m, 2H), 7.27-7.21 (m, 2H), 6.77 (s, 1H), 6.04 (s, 1H), 3.85 (s, 2H), 1.66 (d, J=1.1 Hz, 3H). LCMS ESI-MS m/z: 272 [M+H]$^+$.

Peak 2. $^1$H NMR (400 MHz, DMSO-d$_6$, ppm) δ 8.41 (d, J=5.1 Hz, 2H), 7.21 (d, J=5.1 Hz, 2H), 6.74 (s, 1H), 6.63 (s, 1H), 3.84 (s, 2H), 1.64 (s, 3H). LCMS ESI-MS m/z: 272 [M+H]$^+$.

The absolute stereochemistry was arbitrarily assigned.

Example 33 and 33a: (S)-4-((2-(2,2,2-trifluoro-1-methoxyethyl)-1H-imidazol-5-yl)methyl)pyridine and (R)-4-((2-(2,2,2-trifluoro-1-methoxyethyl)-1H-imidazol-5-yl)methyl)pyridine

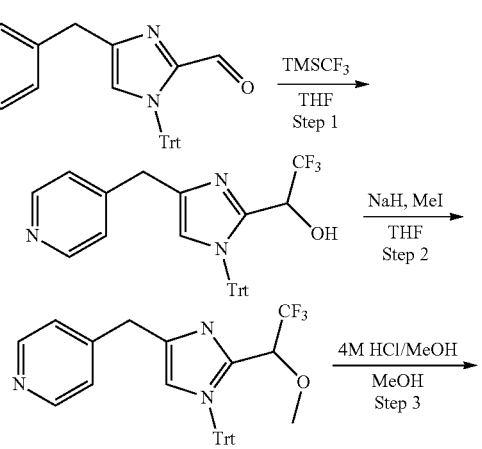

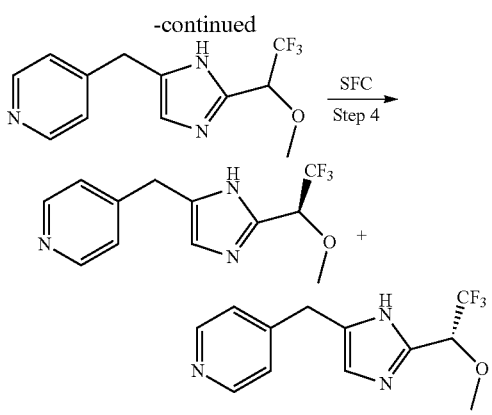

Step 1: 2,2,2-Trifluoro-1-(4-(pyridin-4-ylmethyl)-1-trityl-1H-imidazol-2-yl)ethan-1-ol. To a stirred mixture solution of 4-(pyridin-4-ylmethyl)-1-trityl-1H-imidazole-2-carbaldehyde (1.5 g, 3.5 mmol, according to Example 3, step 3) and TMSCF₃ (0.74 g, 5.2 mmol) in THF (15 mL) was added CsF (0.8 g, 5.2 mmol) in portions at 0° C. under a nitrogen atmosphere. The resulting mixture was stirred for 2 h at room temperature under a nitrogen atmosphere. The reaction mixture was poured to cooled water (20 mL) and extracted with EtOAc (2×20 mL). The combined organic layers were washed with brine (20 mL), dried over anhydrous Na₂SO₄. After filtration, the filtrate was concentrated under reduced pressure. The crude product (1.40 g) was used in the next step directly without further purification. LCMS ESI-MS m/z: =500 [M+H]⁺.

Step 2: 4-((2-(2,2,2-Trifluoro-1-methoxyethyl)-1-trityl-1H-imidazol-5-yl)methyl)pyridine. A solution of 2,2,2-trifluoro-1-(4-(pyridin-4-ylmethyl)-1-trityl-1H-imidazol-2-yl)ethan-1-ol (1.3 g, 2.6 mmol) in THF (13 mL) under a nitrogen atmosphere followed by the addition of NaH (0.21 g, 5.2 mmol, 60% wt) in portions at 0° C. The resulting mixture was stirred for 30 min at 0° C. under a nitrogen atmosphere. To the above mixture was added CH₃I (0.74 g, 5.2 mmol) dropwise at 0° C. The resulting mixture was stirred for 16 h at room temperature. The reaction mixture was poured to cooled water (15 mL) and extracted with EtOAc (3×10 mL). The combined organic layers were washed with brine (15 mL), dried over anhydrous Na₂SO₄. After filtration, the filtrate was concentrated under reduced pressure. The crude product (0.8 g) was used in the next step directly without further purification. LCMS ESI-MS m/z: =514 [M+H]⁺.

Step 3: 4-((2-(2,2,2-Trifluoro-1-methoxyethyl)-1H-imidazol-5-yl)methyl)pyridine. A solution of 4-((2-(2,2,2-trifluoro-1-methoxyethyl)-1-trityl-1H-imidazol-5-yl)methyl)pyridine (0.8 g, 1.56 mmol) in MeOH (4 mL) was added 4 M HCl/MeOH (4 mL) dropwise at 10° C. under a nitrogen atmosphere. The reaction was stirred for 2 h at room temperature. The resulting mixture was concentrated under vacuum. The residue was dissolved in EtOAc (10 mL), and H₂O (10 mL) and the mixture were extracted with EtOAc (10 mL×2). The aqueous phase was basified to pH ~10 with sat. Na₂CO₃ (aq). The resulting mixture was extracted with EtOAc (4×10 mL). The combined organic layers were washed with brine (20 mL), dried over anhydrous Na₂SO₄. After filtration, the filtrate was concentrated under reduced pressure. The crude product was purified by reverse phase flash chromatography to afford 4-((2-(2,2,2-trifluoro-1-methoxyethyl)-1H-imidazol-5-yl)methyl)pyridine (0.2 g, 29% over 3 steps) as a white solid. LCMS ESI-MS m/z: = 272 [M+H]⁺.

Step 4: (S)-4-((2-(2,2,2-Trifluoro-1-methoxyethyl)-1H-imidazol-5-yl)methyl)pyridine and (R)-4-((2-(2,2,2-trifluoro-1-methoxyethyl)-1H-imidazol-5-yl)methyl)pyridine. rac-4-((2-(2,2,2-trifluoro-1-methoxyethyl)-1H-imidazol-5-yl)methyl)pyridine (100 mg) was purified by Prep-SFC to afford Peak 1 (33 mg, 33%, ee=100%) as a white solid and Peak 2 (32 mg, 32%, ee=100%) as a white solid.

Peak 1. ¹H NMR: (400 MHz, DMSO-d₆, ppm): δ 12.50-12.15 (m, 1H), 8.52-8.40 (m, 2H), 7.27-7.19 (m, 2H), 7.02-6.68 (m, 1H), 5.11-4.99 (m, 1H), 3.98-3.81 (m, 2H), 3.34 (s, 3H). LCMS ESI-MS m/z: =272 [M+H]⁺.

Peak 2. ¹H NMR: (400 MHz, DMSO-d₆, ppm): δ 12.50-12.15 (m, 1H), 8.52-8.40 (m, 2H), 7.27-7.19 (m, 2H), 7.02-6.68 (m, 1H), 5.11-4.99 (m, 1H), 3.98-3.80 (m, 2H), 3.37-3.33 (m, 3H). LCMS ESI-MS m/z: =272 [M+H]⁺. The absolute stereochemistry was arbitrarily assigned.

Example 34 and 34a: (R)-2,2,2-Trifluoro-1-(5-((2-fluoropyridin-4-yl)methyl)-1H-imidazol-2-yl)ethan-1-ol and (S)-2,2,2-trifluoro-1-(5-((2-fluoropyridin-4-yl)methyl)-1H-imidazol-2-yl)ethan-1-ol

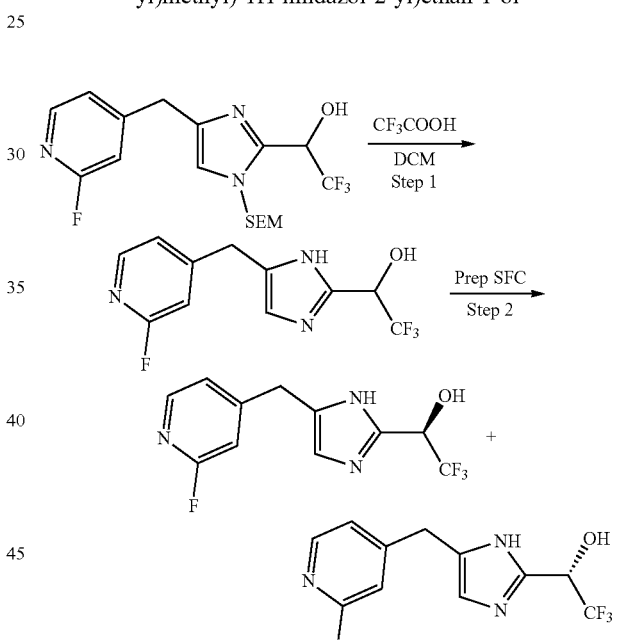

Step 1: 2,2,2-Trifluoro-1-(5-((2-fluoropyridin-4-yl)methyl)-1H-imidazol-2-yl)ethan-1-ol. To a stirred solution of 2,2,2-trifluoro-1-(4-((2-fluoropyridin-4-yl)methyl)-1-((2-(trimethylsilyl)ethoxy)methyl)-1H-imidazol-2-yl)ethan-1-ol (200 mg, 0.5 mmol, Example 29, step 6) in DCM (4 mL) was added CF₃COOH (4 mL) dropwise at room temperature under a nitrogen atmosphere. The resulting mixture was stirred overnight at room temperature under a nitrogen atmosphere. The mixture was concentrated under reduced pressure and dissolved in MeOH (2 mL). The resulting mixture was quenched by the addition of ethylenediamine (1 mL) at room temperature and purified by reverse phase flash chromatography to afford 2,2,2-trifluoro-1-(5-((2-fluoropyridin-4-yl)methyl)-1H-imidazol-2-yl)ethan-1-ol (80 mg, 59%) as a white solid. LCMS ESI-MS m/z: 276 [M+H]⁺.

Step 2: (S)-2,2,2-Trifluoro-1-(5-((2-fluoropyridin-4-yl)methyl)-1H-imidazol-2-yl)ethan-1-ol and (R)-2,2,2-trifluoro-1-(5-((2-fluoropyridin-4-yl)methyl)-1H-imidazol-2-yl)ethan-1-ol. rac-2,2,2-Trifluoro-1-(5-((2-fluoropyridin-4-yl)methyl)-1H-imidazol-2-yl)ethan-1-ol (80 mg) was purified by prep-SFC to afford Peak 1 (21.5 mg, 16%) as a white solid and Peak 2 (13.1 mg, 10%) as a white solid.

Peak 1. $^1$H NMR (400 MHz, DMSO-d$_6$, ppm): δ 8.13 (d, J=5.1 Hz, 1H), 7.22 (dd, J=5.2, 1.3 Hz, 1H), 7.02 (d, J=1.5 Hz, 1H), 6.90 (s, 1H), 5.99 (s, 1H), 5.13 (q, J=7.3 Hz, 1H), 3.92 (s, 2H). LCMS ESI-MS m/z: 276 [M+H]$^+$.

Peak 2. $^1$H NMR (400 MHz, DMSO-d$_6$, ppm): δ 12.23 (d, J=49.6 Hz, 1H), 8.12 (d, J=5.2 Hz, 1H), 7.22 (d, J=5.1 Hz, 1H), 7.10 (d, J=5.8 Hz, 1H), 7.01 (s, 1H), 6.96 (s, 1H), 5.12 (dd, J=10.0, 4.1 Hz, 1H), 3.90 (s, 2H). LCMS ESI-MS m/z: 276 [M+H]$^+$.

The absolute stereochemistry was arbitrarily assigned.

Example 35: (rac)-Pyridin-2-yl(5-(pyridin-4-ylmethyl)-1H-imidazol-2-yl)methanol

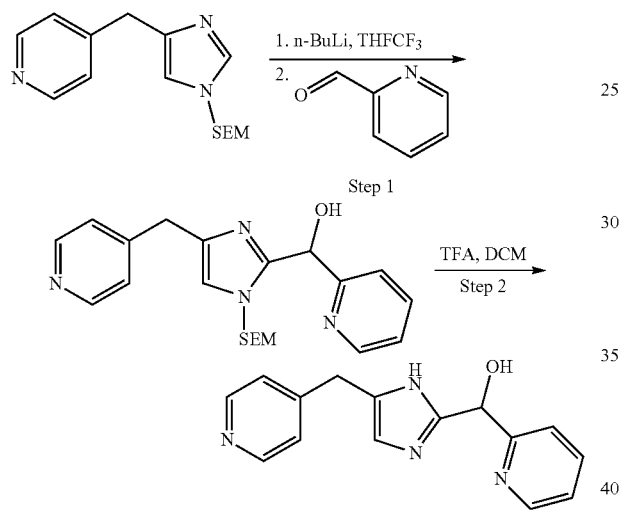

Step 1: Pyridin-2-yl(5-(pyridin-4-ylmethyl)-1-((2-(trimethylsilyl)ethoxy)methyl)-1H-imidazol-2-yl)methanol. To a stirred solution of 4-((1-((2-(trimethylsilyl)ethoxy)methyl)-1H-imidazol-4-yl)methyl)pyridine (500 mg, 1.73 mmol, Example 3, step 3) in THF (10 mL) was added n-BuLi (2.1 mL, 5.19 mmol, 2.5M) dropwise at −60° C. under a nitrogen atmosphere. The resulting mixture was stirred for 1 h at −60° C. under a nitrogen atmosphere. Then 2-formylpyridine (462.5 mg, 4.32 mmol) was added dropwise at −60° C. and the resulting mixture was stirred for another 1 h at −60° C. under a nitrogen atmosphere. The reaction was quenched with sat. NH$_4$Cl (aq) (20 mL) at −60° C. The resulting mixture was extracted with EtOAc (3×10 mL). The combined organic layers were washed with brine (1×10 mL), dried over anhydrous Mg$_2$SO$_4$. After filtration, the filtrate was concentrated under reduced pressure. The residue was purified by reverse phase flash chromatography and then further purified by prep-HPLC to afford pyridin-2-yl(4-(pyridin-4-ylmethyl)-1-((2-(trimethylsilyl)ethoxy)methyl)-1H-imidazol-2-yl)methanol (352 mg, 48%) as a light yellow oil. LCMS ESI-MS m/z: =397 [M+H]$^+$.

Step 2: Pyridin-2-yl(5-(pyridin-4-ylmethyl)-1H-imidazol-2-yl)methanol. To a stirred solution of pyridin-2-yl(4-(pyridin-4-ylmethyl)-1-((2-(trimethylsilyl)ethoxy)methyl)-1H-imidazol-2-yl)methanol (352 mg, 0.825 mmol) in DCM (1.5 mL) was added TFA (1.5 mL) dropwise at 0° C. under a nitrogen atmosphere. The resulting mixture was stirred overnight at 30° C. The resulting mixture was concentrated under reduced pressure. The residue was dissolved in DCM (10 mL) and H$_2$O (10 mL), the mixture was basified to pH 9-10 with sat. Na$_2$CO$_3$. The resulting mixture was extracted with DCM (5×20 mL). The organic layers were combined and dried over anhydrous MgSO$_4$. The solids were removed by filtration and the filter cake was rinsed with DCM (2×20 mL). The resulting organic solution was concentrated under reduced pressure. The residue was purified by prep-HPLC to afford pyridin-2-yl(5-(pyridin-4-ylmethyl)-1H-imidazol-2-yl)methanol (3.1 mg, 1.4%) as an off-white solid. $^1$H NMR (400 MHz, DMSO-d$_6$ ppm): δ 11.83 (d, J=70.9 Hz, 1H), 8.43 (dd, J=13.7, 4.7 Hz, 3H), 7.79 (t, J=7.7 Hz, 1H), 7.36-7.14 (m, 3H), 6.63 (d, J=92.6 Hz, 1H), 6.16 (d, J=4.2 Hz, 1H), 5.65 (t, J=4.0 Hz, 1H), 3.81 (d, J=50.1 Hz, 2H). LCMS ESI-MS m/z: =267 [M+H]$^+$.

Example 36: 3-Fluoro-4-((2-(2,2,2-trifluoroethyl)-1H-imidazol-4-yl)methyl)pyridine

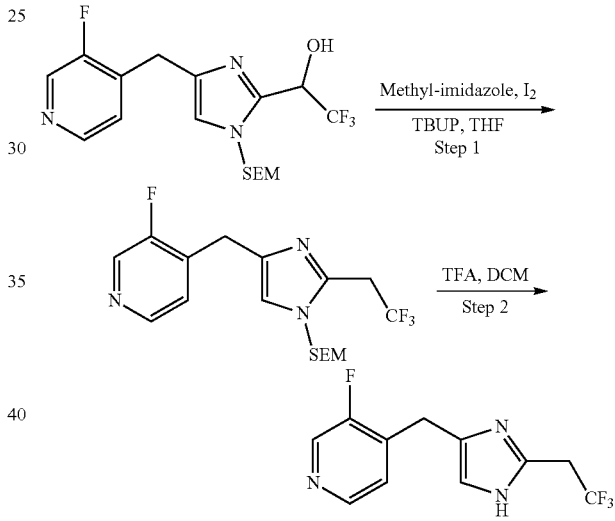

Step 1: 3-Fluoro-4-((2-(2,2,2-trifluoroethyl)-1-((2-(trimethylsilyl)ethoxy)methyl)-1H-imidazol-4-yl)methyl)pyridine. A solution of 2,2,2-trifluoro-1-(5-((3-fluoropyridin-4-yl)methyl)-1-((2-(trimethylsilyl)ethoxy]methyl)imidazol-2-yl)ethanol (400 mg, 1 mmol, Example 38, Step 5) in THF (3.6 mL) was treated with methyl-imidazole (98.5 mg, 1.20 mmol), tributylphosphine (607 mg, 3.00 mmol), and I$_2$ (241 mg, 0.95 mmol) for 5 h at 25° C. under a nitrogen atmosphere. The resulting mixture was diluted with EtOAc (10 mL). The reaction was quenched by the addition of aq. Na$_2$S$_2$O$_3$ (10 mL) at room temperature. The aqueous layer was extracted with EtOAc (2×10 mL). The combined organic layers were dried over Na$_2$SO$_4$, filtered, and concentrated under reduced pressure. The residue was purified by reverse phase flash chromatography to afford 3-fluoro-4-((2-(2,2,2-trifluoroethyl)-1-((2-(trimethylsilyl)ethoxy)methyl)-1H-imidazol-4-yl)methyl)pyridine (230 mg, 57%) as a yellow oil. LCMS ESI-MS m/z: 390 [M+H]$^+$.

Step 2: 3-Fluoro-4-((2-(2,2,2-trifluoroethyl)-1H-imidazol-4-yl)methyl)pyridine. To a stirred solution of 3-fluoro-4-((2-(2,2,2-trifluoroethyl)-1-((2-(trimethylsilyl)ethoxy)methyl)-1H-imidazol-4-yl)methyl)pyridine (230 mg, 0.56 mmol) in DCM (2.3 mL) was added TFA (2.3 mL) dropwise at 0° C. under a nitrogen atmosphere. The resulting mixture was stirred for 3 h at room temperature. The resulting mixture was concentrated under reduced pressure. The residue was dissolved in DCM (10 mL) and H$_2$O (10 mL), the mixture was basified to pH 9-10 with sat. Na$_2$CO$_3$. The resulting mixture was extracted with DCM (5×20 mL). The organic layers were combined and dried over anhydrous MgSO$_4$. The solids were removed by filtration and the filter cake was rinsed in the funnel with DCM (2×20 mL). The resulting organic solution was concentrated under reduced pressure. The residue was purified by prep-HPLC to afford 3-fluoro-4-((2-(2,2,2-trifluoroethyl)-1H-imidazol-4-yl)methyl)pyridine (94.4 mg, 65%) as a white solid. $^1$H NMR (400 MHz, DMSO-d$_6$ ppm): δ 12.01 (s, 1H), 8.48 (d, J=1.7 Hz, 1H), 8.32 (d, J=4.9 Hz, 1H), 7.30 (t, J=5.8 Hz, 1H), 6.91 (s, 1H), 3.89 (s, 2H), 3.66 (q, J 11.1 Hz, 2H). LCMS ESI-MS m/z: =260 [M+H]$^+$.

Example 37 and 37a: (S)-2,2,2-Trifluoro-1-(4-((3-methylpyridin-4-yl)methyl)-1H-imidazol-2-yl)ethan-1-ol and (R)-2,2,2-trifluoro-1-(4-((3-methylpyridin-4-yl)methyl)-1H-imidazol-2-yl)ethan-1-ol

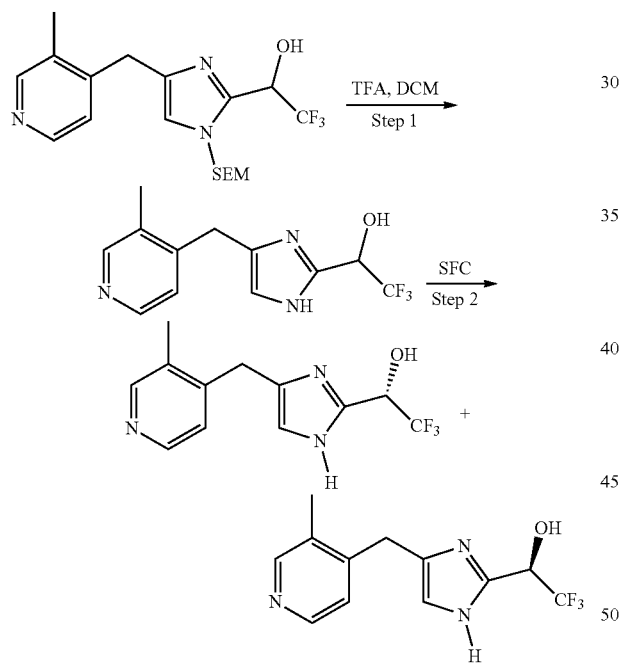

Step 1: (rac)-2,2,2-Trifluoro-1-(4-((3-methylpyridin-4-yl)methyl)-1H-imidazol-2-yl)ethan-1-ol. To a stirred solution of 2,2,2-trifluoro-1-(4-((3-methylpyridin-4-yl)methyl]-1-((2-(trimethylsilyl)ethoxy]methyl)imidazol-2-yl)ethanol (250 mg, 0.623 mmol, Example 25, step 5) in DCM (2 mL) was added TFA (2 mL) dropwise at 0° C. under nitrogen atmosphere. The resulting mixture was stirred overnight at room temperature under nitrogen atmosphere. The resulting mixture was concentrated under vacuum to yield yellow oil. The residue was dissolved in DCM (10 mL) and H$_2$O (10 mL), the resulting mixture was basified to pH 8 with sat. Na$_2$CO$_3$ (aq). The resulting mixture was extracted with DCM (10 mL×3). The combined organic layers were washed with brine (30 mL), dried over anhydrous Na$_2$SO$_4$. After filtration, the filtrate was concentrated under reduced pressure. The crude product was purified by reverse phase flash chromatography to afford 2,2,2-trifluoro-1-(4-((3-methylpyridin-4-yl)methyl)-1H-imidazol-2-yl)ethanol (150 mg, 89%) as a yellow oil. LCMS ESI-MS m/z: =272 [M+H]$^+$.

Step 2: (S)-2,2,2-Trifluoro-1-(4-((3-methylpyridin-4-yl)methyl)-1H-imidazol-2-yl)ethan-1-ol and (R)-2,2,2-trifluoro-1-(4-((3-methylpyridin-4-yl)methyl)-1H-imidazol-2-yl)ethan-1-ol. (rac)-2,2,2-Trifluoro-1-(4-((3-methylpyridin-4-yl)methyl)-1H-imidazol-2-yl)ethanol (100 mg) was separated by Prep-SFC to afford Peak 1 (32 mg, crude) as a yellow solid and Peak 2 (27 mg, crude) as a yellow solid.

Peak 1 crude product (32 mg) was further purified by reverse phase flash chromatography to afford pure isomer (27 mg) as an off-white solid.

Peak 2 crude product (27 mg) was further purified by reverse phase flash chromatography to afford pure isomer (19.5 mg) as an off-white solid.

Peak 1. $^1$H NMR: (400 MHz, DMSO-d$_6$, ppm): δ 8.33-8.25 (m, 2H), 7.08 (d, J=4.8 Hz, 1H), 6.76 (s, 1H), 5.94 (s, OH), 5.11 (q, J=7.2 Hz, 1H), 3.82 (s, 2H), 2.53-2.47 (m, 2H), 2.26 (s, 3H).

Peak 2. $^1$H NMR (400 MHz, DMSO-d$_6$, ppm): δ 12.23-12.10 (d, 1H), 8.35-8.24 (m, 2H), 7.12-7.01 (m, 2H), 6.85-6.55 (m, 1H), 5.17-5.04 (m, 1H), 3.89 (s, 1H), 3.80 (s, 1H), 2.29-2.23 (d, J=3.6 Hz, 3H).

The absolute stereochemistry was arbitrarily assigned.

Example 38 and 38a: (S)-2,2,2-Trifluoro-1-(4-((3-fluoropyridin-4-yl)methyl)-1H-imidazol-2-yl)ethan-1-ol and (R)-2,2,2-trifluoro-1-(4-((3-fluoropyridin-4-yl)methyl)-1H-imidazol-2-yl)ethan-1-ol

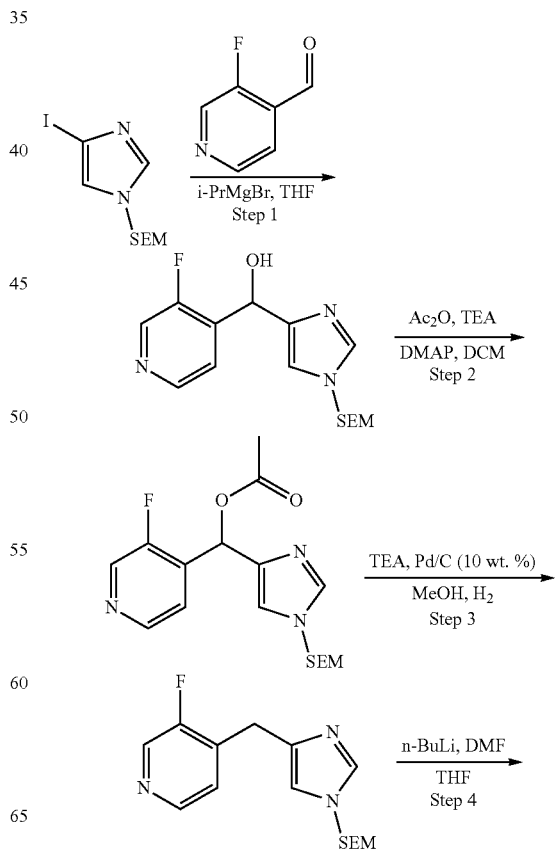

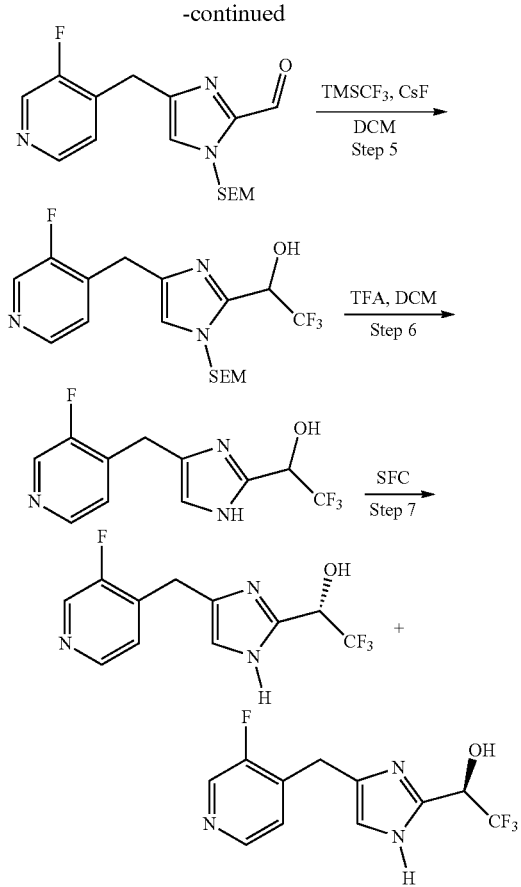

Step 1: (3-Fluoropyridin-4-yl)(1-((2-(trimethylsilyl)ethoxy)methyl)-1H-imidazol-4-yl)methanol. A solution of 4-iodo-1-((2-(trimethylsilyl)ethoxy)methyl)imidazole (5 g, 15.4 mmol) in THF (10 mL) was treated with i-PrMgBr (18.5 mL, 18.5 mmol, 1 M) for 1 h at −15° C. under a nitrogen atmosphere followed by the addition of 3-fluoropyridine-4-carbaldehyde (2.3 g, 18.5 mmol) dropwise at −15° C. The resulting mixture was stirred for 1 h at −15° C. under a nitrogen atmosphere. The reaction was quenched by the addition of Na$_2$SO$_4$.10H$_2$O (5 g) solid at room temperature. The resulting mixture was filtered, and the filter cake was rinsed with EtOAc (2×20 mL). The filtrate was collected and concentrated under reduced pressure. The residue was purified by reverse phase flash chromatography to afford (3-fluoropyridin-4-yl)(1-((2-(trimethylsilyl)ethoxy)methyl)-1H-imidazol-4-yl)methanol (3.9 g, 77%) as a yellow oil. LCMS ESI-MS m/z: 324 [M+H]$^+$.

Step 2: (3-Fluoropyridin-4-yl)(1-((2-(trimethylsilyl)ethoxy)methyl)-1H-imidazol-4-yl)methyl acetate. To a stirred solution of (3-fluoropyridin-4-yl)(3-((2-(trimethylsilyl)ethoxy)methyl)imidazol-4-yl)methanol (3.9 g, 11.9 mmol) in DCM (40 mL) was added TEA (2.4 g, 23.8 mmol), DMAP (0.15 g, 1.2 mmol) and Ac$_2$O (1.2 g, 11.9 mmol) at room temperature under a nitrogen atmosphere. The resulting mixture was stirred for 3 h at room temperature under a nitrogen atmosphere. The resulting mixture was concentrated under reduced pressure. The resulting mixture was diluted with EtOAc (30 mL). The resulting mixture was washed with water (2×20 mL) and brine (20 mL). The resulting mixture was concentrated under. The residue was purified by reverse phase flash chromatography to afford (3-fluoropyridin-4-yl)(1-((2-(trimethylsilyl)ethoxy)methyl)-1H-imidazol-4-yl)methyl acetate (4 g, 87%) as a brown oil. LCMS ESI-MS m/z: 366 [M+H]$^+$.

Step 3: 3-Fluoro-4-((1-((2-(trimethylsilyl)ethoxy)methyl)-1H-imidazol-4-yl)methyl)pyridine. A mixture of (3-fluoropyridin-4-yl)(3-((2-(trimethylsilyl)ethoxy)methyl)imidazol-4-yl)methyl acetate (4 g, 10.4 mmol), TEA (1.1 g, 10.9 mmol) and Pd/C (0.4 g, 10 wt. %) in MeOH (40 mL) was stirred overnight at room temperature under a hydrogen atmosphere. The resulting mixture was filtered, and the filter cake was washed with EtOAc (2×20 mL). The filtrate was collected and concentrated under reduced pressure. The residue was purified by reverse phase flash chromatography to afford 3-fluoro-4-((1-((2-(trimethylsilyl)ethoxy)methyl)-1H-imidazol-4-yl)methyl)pyridine (1.9 g, 56%) as a brown oil. LCMS ESI-MS m/z: 308 [M+H]$^+$.

Step 4: 4-((3-Fluoropyridin-4-yl)methyl)-1-((2-(trimethylsilyl)ethoxy)methyl)-1H-imidazole-2-carbaldehyde. A solution of 3-fluoro-4-((1-((2-(trimethylsilyl)ethoxy)methyl)imidazol-4-yl)methyl)pyridine (2.1 g, 6.4 mmol) in THF (30 mL) was treated with n-BuLi (8.2 mL, 19.2 mmol, 2.5 M) for 2 h at −40~−30° C. under a nitrogen atmosphere followed by the addition of DMF (4.7 g, 64 mmol) dropwise at −40~−30° C. The resulting mixture was stirred for 4 h at −40~−30° C. under a nitrogen atmosphere. The reaction was quenched by the addition of water/ice (10 mL) at −60° C. The aqueous layer was extracted with EtOAc (3×20 mL). The resulting mixture was concentrated under reduced pressure. The residue was purified by reverse phase flash chromatography to afford 4-((3-fluoropyridin-4-yl)methyl)-1-((2-(trimethylsilyl)ethoxy)methyl)-1H-imidazole-2-carbaldehyde (1.1 g, 50%) as a yellow oil. LCMS ESI-MS m/z: 336 [M+H]$^+$.

Step 5: 2,2,2-Trifluoro-1-(4-((3-fluoropyridin-4-yl)methyl)-1-((2-(trimethylsilyl)ethoxy)methyl)-1H-imidazol-2-yl)ethan-1-ol. A solution of 4-((3-fluoropyridin-4-yl)methyl)-1-((2-(trimethylsilyl)ethoxy)methyl)imidazole-2-carbaldehyde (1.1 g, 3.2 mmol) in DCM (22 mL) was treated with TMSCF$_3$ (0.7 g, 4.8 mmol) for 5 min at −10° C. under a nitrogen atmosphere followed by the addition of CsF (0.7 g, 4.8 mmol) in portions at −10° C. The resulting mixture was stirred for 3 h at −10° C. under a nitrogen atmosphere. The resulting mixture was concentrated under reduced pressure. The residue was purified by reverse phase flash chromatography to afford 2,2,2-trifluoro-1-(4-((3-fluoropyridin-4-yl)methyl)-1-((2-(trimethylsilyl)ethoxy)methyl)-1H-imidazol-2-yl)ethan-1-ol (602 mg, 42%) as a yellow oil. LCMS ESI-MS m/z: 406 [M+H]$^+$.

Step 6: 2,2,2-Trifluoro-1-(4-((3-fluoropyridin-4-yl)methyl)-1H-imidazol-2-yl)ethan-1-ol. A solution of 2,2,2-trifluoro-1-(4-((3-fluoropyridin-4-yl)methyl)-1-((2-(trimethylsilyl)ethoxy)methyl)imidazol-2-yl)ethanol (200 mg, 0.49 mmol) in DCM (2 mL) was treated with TFA (2 mL) for 3 h at room temperature under a nitrogen atmosphere. The resulting mixture was concentrated under reduced pressure. The residue was dissolved in DCM (5 mL) and H$_2$O (10 mL), the mixture was basified to pH 9-10 with sat. Na$_2$CO$_3$. The resulting mixture was extracted with DCM (5×5 mL). The organic layers were combined and dried over anhydrous MgSO$_4$. The solids were removed by filtration and the filter cake was rinsed with DCM (2×5 mL). The filtrate was concentrated under reduced pressure. The residue was purified by reverse phase flash chromatography to afford 2,2,2-trifluoro-1-(4-((3-fluoropyridin-4-yl)methyl)-1H-imidazol-2-yl)ethanol (107 mg, 75%) as yellow oil. LCMS ESI-MS m/z: 276 [M+H]$^+$.

Step 7: (S)-2,2,2-Trifluoro-1-(4-((3-fluoropyridin-4-yl)methyl)-1H-imidazol-2-yl)ethan-1-ol and (R)-2,2,2-trifluoro-1-(4-((3-fluoropyridin-4-yl)methyl)-1H-imidazol-2-yl)ethan-1-ol. 2,2,2-trifluoro-1-(4-((3-fluoropyridin-4-yl)methyl)-1H-imidazol-2-yl)ethanol (100 mg) was separated by prep-SFC to afford Peak 1 (27 mg) as a white solid and Peak 2 (23 mg) as a white solid.

Peak 1. $^1$H NMR: (400 MHz, DMSO-$d_6$, ppm): δ 12.23 (d, J=58.7 Hz, 1H), 8.49 (dd, J=14.4, 1.7 Hz, 1H), 8.38-8.29 (m, 1H), 7.28 (ddd, J=22.9, 6.6, 4.8 Hz, 1H), 7.10 (dd, J=15.1, 5.7 Hz, 1H), 6.94-6.61 (m, 1H), 5.11 (dt, J=12.0, 6.1 Hz, 1H), 3.93 (d, J=42.9 Hz, 2H). LCMS ESI-MS m/z: =276 [M+H]$^+$.

Peak 2. $^1$H NMR: (400 MHz, DMSO-$d_6$, ppm): δ 12.23 (d, J=58.5 Hz, 1H), 8.49 (dd, J=14.4, 1.7 Hz, 1H), 8.39-8.28 (m, 1H), 7.28 (ddd, J=22.9, 6.6, 4.9 Hz, 1H), 7.10 (dd, J=15.4, 5.8 Hz, 1H), 6.78 (dd, J=111.9, 1.7 Hz, 1H), 5.20-5.03 (m, 1H), 3.99 (s, 2H). LCMS ESI-MS m/z: =276 [M+H]$^+$.

The absolute stereochemistry was arbitrarily assigned.

Example 39: 1,1,1,3,3,3-Hexafluoro-2-(4-(pyridin-4-ylmethyl)-1H-imidazol-2-yl)propan-2-ol

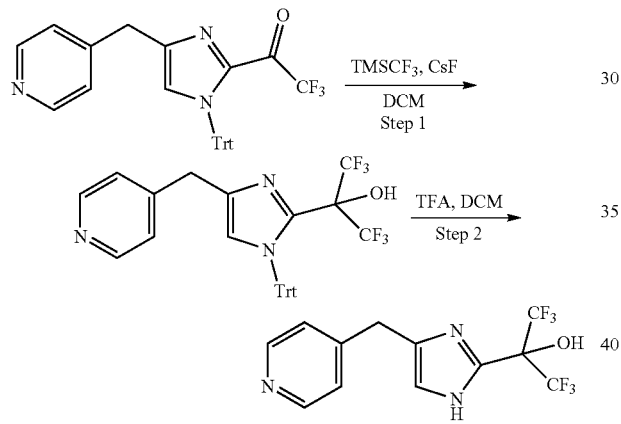

Step 1: 1,1,1,3,3,3-Hexafluoro-2-(4-(pyridin-4-ylmethyl)-1-trityl-1H-imidazol-2-yl)propan-2-ol. A solution of 2,2,2-trifluoro-1-(4-(pyridin-4-ylmethyl)-1-(triphenylmethyl)imidazol-2-yl)ethanone (500 mg, 1.0 mmol, according to Example 12) in DCM (2.5 mL) was treated with TMSCF$_3$ (214 mg, 1.5 mmol) for 5 min at −10° C. under a nitrogen atmosphere followed by the addition of CsF (15.2 mg, 0.1 mmol) in portions at −10° C. The resulting mixture was stirred for 3 h at −10° C. under a nitrogen atmosphere. The reaction was quenched with sat. NH$_4$Cl (aq) (10 mL) at room temperature. The resulting mixture was extracted with EtOAc (3×10 mL). The combined organic layers were washed with brine (1×10 mL), dried over anhydrous Na$_2$SO$_4$. After filtration, the filtrate was concentrated under reduced pressure. The residue was purified by prep-HPLC to afford 1,1,1,3,3,3-hexafluoro-2-(4-(pyridin-4-ylmethyl)-1-trityl-1H-imidazol-2-yl)propan-2-ol (228 mg, 40%) as a white solid. LCMS ESI-MS m/z: =568 [M+H]$^+$.

Step 2: 1,1,1,3,3,3-Hexafluoro-2-(4-(pyridin-4-ylmethyl)-1H-imidazol-2-yl)propan-2-ol. To a stirred solution of 1,1,1,3,3,3-hexafluoro-2-(4-(pyridin-4-ylmethyl)-1-(triphenylmethyl)imidazol-2-yl)propan-2-ol (228.0 mg, 0.4 mmol) in DCM (2.5 mL) was added TFA (2.5 mL) dropwise at 0° C. under a nitrogen atmosphere. The resulting mixture was stirred overnight at 30° C. The resulting mixture was concentrated under reduced pressure. The residue was dissolved in DCM (5 mL) and H$_2$O (5 mL), the mixture was basified to pH 9-10 with sat. Na$_2$CO$_3$. The resulting mixture was extracted with DCM (5×10 mL). The organic layers were combined and dried over anhydrous Na$_2$SO$_4$. The solids were removed by filtration and the filter cake was rinsed in the funnel with DCM (2×5 mL). The resulting organic solution was concentrated under reduced pressure. The residue was purified by prep-HPLC to afford 1,1,1,3,3,3-hexafluoro-2-(4-(pyridin-4-ylmethyl)-1H-imidazol-2-yl)propan-2-ol (13.8 mg, 11%) as a white solid. $^1$H NMR (400 MHz, DMSO-$d_6$ ppm): δ 8.46 (d, J=5.1 Hz, 2H), 7.24 (d, J=4.9 Hz, 2H), 6.92 (s, 1H), 3.91 (s, 2H). $^{19}$F NMR: (376 MHz, DMSO-$d_6$, ppm): δ−74.5317, −76.2685, −76.4187, −76.6636. LCMS ESI-MS m/z: =326 [M+H]$^+$.

Example 40: (rac)-1,1,1-Trifluoro-2-(4-(pyridin-4-ylmethyl)-1H-imidazol-2-yl)propan-2-ol

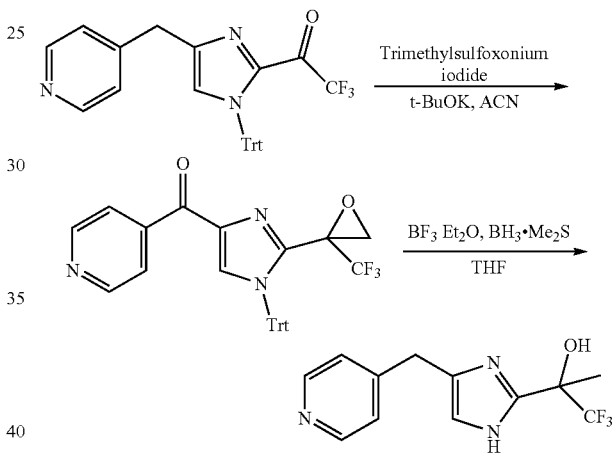

Step 1: Pyridin-4-yl(2-(2-(trifluoromethyl)oxiran-2-yl)-1-trityl-1H-imidazol-4-yl)methanone. To a stirred solution of t-BuOK (0.3 g, 3 mmol) in ACN (10 mL) was added trimethylsulfoxonium iodide (0.4 g, 2 mmol) dropwise at room temperature under a nitrogen atmosphere. The resulting mixture was stirred for 30 min at room temperature under a nitrogen atmosphere and 2,2,2-trifluoro-1-(4-(pyridin-4-ylmethyl)-1-(triphenylmethyl)imidazol-2-yl)ethanone (1 g, 2 mmol, according to Example 12, step 2) in MeCN (2 mL) was added dropwise at room temperature. The resulting mixture was stirred for another 16 h at room temperature under a nitrogen atmosphere. The reaction was quenched with water (50 mL) at room temperature. The resulting mixture was extracted with EtOAc (3×20 mL). The combined organic layers were washed with brine (1×50 mL), dried over anhydrous Na$_2$SO$_4$, filtered and concentrated under reduced pressure. The residue was purified by prep-HPLC to afford 4-(2-(2-(trifluoromethyl)oxiran-2-yl)-1-(triphenylmethyl)imidazole-4-carbonyl)pyridine (330 mg, 31%) as a white solid. LCMS ESI-MS m/z: =526 [M+H]$^+$.

Step 2: (rac)-1,1,1-Trifluoro-2-(4-(pyridin-4-ylmethyl)-1H-imidazol-2-yl)propan-2-ol. To a stirred solution of BF$_3$·Et$_2$O (81 mg, 0.5 mmol) in THF (1.5 mL) was added BH$_3$·Me$_2$S (2.1 mg, 0.1 mmol) dropwise at 0° C. under a nitrogen atmosphere. Then, 4-(2-(2-(trifluoromethyl)oxiran- 2-yl)-1-(triphenylmethyl)imidazole-4-carbonyl)pyridine (150 mg, 0.3 mmol) in THF (0.2 mL) was added dropwise at 0° C. and the resulting mixture was stirred overnight at room temperature under a nitrogen atmosphere. The reaction was quenched with the addition of water (10 mL) at room temperature. The resulting mixture was extracted with EtOAc (3×5 mL). The combined organic layers were washed with brine (5 mL), dried over anhydrous $Na_2SO_4$, filtered and concentrated under reduced pressure to afford crude product as a white solid. The crude product was purified by prep-HPLC to afford (rac)-1,1,1-trifluoro-2-(4-(pyridin-4-ylmethyl)-1H-imidazol-2-yl)propan-2-ol (18 mg, 23%) as a white solid. $^1H$ NMR (400 MHz, DMSO-$d_6$, ppm): δ 8.58-8.39 (m, 2H), 7.32-7.18 (m, 2H), 6.78 (s, 1H), 6.04 (s, 1H), 3.86 (s, 2H), 1.67 (s, 3H). LCMS ESI-MS m/z: =272 $[M+H]^+$.

Example A

Biological Assay

Each reaction was run at a volume of 20 μL containing 50 μM compound (dissolved in DMSO; final concentration of DMSO is 1% v/v), 40 nM human SARM1$_{(50-724)}$, 0.3 mM NMN, 20 μM NAD, 1 mM TCEP, 25 mM HEPES pH 7.4, 10 mM KCl and 10 mM $MgCl_2$. The reaction was incubated at room temperature for 60 minutes and quenched with 20 μL of 0.4% formic acid. The samples were run on Agilent HPLC 1260 Infinity II with Synergi 2.5 μM Fusion-RP 100 Å (100×3.0 mm) LC column from Phenomenex. Total run time for each sample was 4 minutes. The run was isocratic with 1.5% methanol in 40 mM ammonium acetate pH 6.0. Samples were run at a flow rate of 0.8 mL/min at 55° C. Peak areas of NAD and NAM were determined using OpenLAB CDS (Chem Station edition) software. For dose-response, the compound was diluted serially 1:3 in DMSO and added to the reaction starting at a final compound concentration of 100 μM in 1% DMSO.

$IC_{50}$ data according to the assay described above is provided in Table 1 ($IC_{50}$<1 μM (*); 1 μM≤$IC_{50}$<10 μM (); and 10 μM≤$IC_{50}$≤100 μM (*)). † The absolute stereochemistry was assigned arbitrarily.

TABLE 1

| Ex. No. | Average $IC_{50}$ (μM) |
|---|---|
| 1 | *** |
| 2 | ** |
| 3 | *** |
| 4 | ** |
| 5 | *** |
| 5a† | *** |
| 5b† | ** |
| 6 | *** |
| 7† | *** |
| 7a† | *** |
| 8 | * |
| 9 | ** |
| 10 | ** |
| 11 | ** |
| 12 | *** |
| 13 | ** |
| 14 | * |
| 15† | ** |
| 15a† | *** |
| 16† | ** |
| 16a† | ** |
| 17† | * |
| 17a† | ** |
| 18 | >100 μM |

TABLE 1-continued

| Ex. No. | Average $IC_{50}$ (μM) |
|---|---|
| 19† | * |
| 19a† | ** |
| 20† | ** |
| 20a† | *** |
| 21 | * |
| 22 | * |
| 23 | *** |
| 24† | *** |
| 24a† | * |
| 24b† | *** |
| 24c† | >50 μM |
| 25 | *** |
| 26† | * |
| 26a† | *** |
| 27 | *** |
| 28 | >50 μM |
| 29 | >50 μM |
| 30† | * |
| 30a† | ** |
| 31† | >50 μM |
| 31a† | ** |
| 32† | *** |
| 32a† | ** |
| 33† | ** |
| 33a† | ** |
| 34† | >100 μM |
| 34a† | >100 μM |
| 35 | ** |
| 36 | *** |
| 37† | ** |
| 37a† | *** |
| 38† | *** |
| 38a† | ** |
| 39 | ** |
| 40 | ** |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A method of treating a neurological disorder in a patient in need thereof comprising administering to the patient a therapeutically effective amount of a compound of Formula IIa:

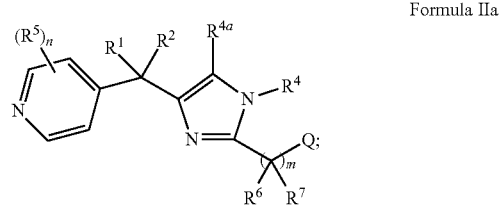

Formula IIa or a pharmaceutically acceptable salt thereof, wherein:
Q is —Cy, —$C_{1-4}$ alkyl-Cy, —$CF_3$, or —$C_{1-4}$ alkyl-$CF_3$;
$R^1$ is H;
$R^2$ is H or $C_{1-4}$ alkyl;
$R^4$ and $R^{4a}$ are each independently selected from H, halo, and $C_{1-4}$ alkyl;
each $R^5$ is independently selected from halo and $C_{1-4}$ alkyl, wherein $R^5$ is attached to a carbon atom;

R⁶ and R⁷ are each independently selected from H, —ORᵃ, —NRᶜRᵈ, C₁₋₄ alkyl, and C₁₋₄ haloalkyl;

Cy is selected from C₆₋₁₀ aryl, C₃₋₇ cycloalkyl, 5-6 membered heteroaryl, and 4-7 membered heterocycloalkyl, each optionally substituted by 1, 2, 3, 4, or 5 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRCS(O)Rᵇ, NRCS(O)₂Rᵇ, NRCS(O)₂NRᶜRᵈ, S(O)Rᵇ, S(O)NRᶜRᵈ, S(O)₂Rᵇ, and S(O)₂NRᶜRᵈ, or two adjacent Roy substituents together with the atoms to which they are attached form a fused phenyl, C₃₋₇ cycloalkyl, 5-6 membered heteroaryl, or 4-7 membered heterocycloalkyl ring, each optionally substituted by 1, 2, 3, 4, or 5 substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRCS(O)Rᵇ, NRCS(O)₂Rᵇ, NRCS(O)₂NRᶜRᵈ, S(O)Rᵇ, S(O)NRᶜRᵈ, S(O)₂Rᵇ, and S(O)₂NRᶜRᵈ, each Rᵃ, Rᵇ, Rᶜ, and Rᵈ is independently selected from H, C₁₋₄ alkyl, and C₁₋₄ haloalkyl, wherein said C₁₋₄ alkyl is optionally substituted with 1, 2, or 3 substituents independently selected from OH, CN, amino, halo, C₁₋₄ alkyl, C₁₋₄ alkoxy, C₁₋₄ haloalkyl, and C₁₋₄ haloalkoxy;

each Rᵉ is independently selected from H, C₁₋₄ alkyl, and CN;

n is 0, 1, or 2; and m is 1 or 2; wherein the neurological disorder is selected from amyotrophic lateral sclerosis (ALS), multiple sclerosis (MS), diabetic neuropathy, traumatic brain injury (TBI), ocular neuropathy, Parkinson's disease, Alzheimer's disease, and peripheral neuropathy.

2. The method of claim 1, or a pharmaceutically acceptable salt thereof, wherein R² is H.

3. The method of claim 2, or a pharmaceutically acceptable salt thereof, wherein R⁴ is H.

4. The method of claim 3, or a pharmaceutically acceptable salt thereof, wherein R^{4a} is H.

5. The method of claim 4, or a pharmaceutically acceptable salt thereof, wherein R⁶ and R⁷ are each independently selected from H and OH.

6. The method of claim 5, or a pharmaceutically acceptable salt thereof, wherein at least one of R⁶ and R⁷ is H.

7. The method of claim 6, or a pharmaceutically acceptable salt thereof, wherein both R⁶ and R⁷ are H.

8. The method of claim 6, or a pharmaceutically acceptable salt thereof, wherein R⁶ is OH and R⁷ is H.

9. The method of claim 6, or a pharmaceutically acceptable salt thereof, wherein Q is —CF₃.

10. The method of claim 6, or a pharmaceutically acceptable salt thereof, wherein Q is —Cy.

11. The method of claim 10, or a pharmaceutically acceptable salt thereof, wherein Cy is selected from C₆₋₁₀ aryl and 5-6 membered heteroaryl, each optionally substituted by 1, 2, 3, 4, or 5 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRCS(O)Rᵇ, NRCS(O)₂Rᵇ, NRCS(O)₂NRᶜRᵈ, S(O)Rᵇ, S(O)NRᶜRᵈ, S(O)₂Rᵇ, and S(O)₂NRᶜRᵈ.

12. The method of claim 11, or a pharmaceutically acceptable salt thereof, wherein Cy is selected from 5-6 membered heteroaryl optionally substituted by 1, 2, 3, or 4 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRCS(O)Rᵇ, NRCS(O)₂Rᵇ, NRCS(O)₂NRᶜRᵈ, S(O)Rᵇ, S(O)NRᶜRᵈ, S(O)₂Rᵇ, and S(O)₂NRᶜRᵈ.

13. The method of claim 12, or a pharmaceutically acceptable salt thereof, wherein Cy is thiazoyl optionally substituted by 1 or 2 R^Cy substituents independently selected from halo, C₁₋₄ alkyl, C₁₋₄ haloalkyl, CN, NO₂, ORᵃ, SRᵃ, C(O)Rᵇ, C(O)NRᶜRᵈ, C(O)ORᵃ, OC(O)Rᵇ, OC(O)NRᶜRᵈ, NRᶜRᵈ, NRᶜC(O)Rᵇ, NRᶜC(O)ORᵃ, NRᶜC(O)NRᶜRᵈ, C(=NRᵉ)Rᵇ, C(=NRᵉ)NRᶜRᵈ, NRᶜC(=NRᵉ)NRᶜRᵈ, NRCS(O)Rᵇ, NRCS(O)₂Rᵇ, NRCS(O)₂NRᶜRᵈ, S(O)Rᵇ, S(O)NRᶜRᵈ, S(O)₂Rᵇ, and S(O)₂NRᶜRᵈ.

14. The method of claim 13, or a pharmaceutically acceptable salt thereof, wherein Cy is

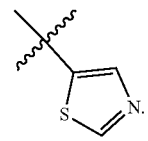 [SMILES: *c1cncs1]

15. The method of claim 13, or a pharmaceutically acceptable salt thereof, wherein each Roy substituent is independently selected from halo, C₁₋₄ alkyl, C₁₋₄ haloalkyl, CN, ORᵃ, C(O)Rᵇ, C(O)NRᶜRᵈ, C(O)ORᵃ, NRᶜRᵈ, NRᶜC(O)Rᵇ, NRCS(O)₂Rᵇ, S(O)₂Rᵇ, and S(O)₂NRᶜRᵈ.

16. The method of claim 9, or a pharmaceutically acceptable salt thereof, wherein n is 0.

17. The method of claim 16, or a pharmaceutically acceptable salt thereof, wherein m is 1.

18. A method of treating a neurological disorder in a patient in need thereof comprising administering to the patient a therapeutically effective amount of a compound selected from:

4-((2-(2,2,2-Trifluoroethyl)-1H-imidazol-4-yl)methyl) pyridine;
4-((2-(3,3,3-trifluoropropyl)-1H-imidazol-4-yl)methyl) pyridine;
2-(4-(Pyridin-4-ylmethyl)-1H-imidazol-2-yl)acetonitrile;
3-(4-(Pyridin-4-ylmethyl)-1H-imidazol-2-yl)propanenitrile;
rac-4-(1-(2-(2,2,2-Trifluoroethyl)-1H-imidazol-4-yl) ethyl)pyridine;
(R)-4-(1-(2-(2,2,2-Trifluoroethyl)-1H-imidazol-4-yl) ethyl)pyridine;
(S)-4-(1-(2-(2,2,2-Trifluoroethyl)-1H-imidazol-4-yl) ethyl)pyridine;
5-((4-(Pyridin-4-ylmethyl)-1H-imidazol-2-yl)methyl)thiazole;
4-((5-(2,2,2-Trifluoroethyl)-1H-1,2,4-triazol-3-yl) methyl)pyridine;
2-(Pyridin-4-ylmethyl)-4-(2,2,2-trifluoroethyl)thiazole;
4-(Pyridin-4-ylmethyl)-2-(2,2,2-trifluoroethyl)thiazole;
rac-4-(1-(5-(2,2,2-trifluoroethyl)-1H-pyrrol-2-yl)ethyl) pyridine;
(S)-2,2,2-Trifluoro-1-(5-(pyridin-4-ylmethyl)-1H-imidazol-2-yl)ethan-1-ol;

(R)-2,2,2-Trifluoro-1-(5-(pyridin-4-ylmethyl)-1H-imidazol-2-yl)ethan-1-ol;
2,2,2-Trifluoro-1-(5-(pyridin-4-ylmethyl)-1H-imidazol-2-yl)ethan-1-one;
(E/Z)-2,2,2-Trifluoro-1-(5-(pyridin-4-ylmethyl)-1H-imidazol-2-yl)ethan-1-one oxime;
4-((5-Methyl-2-(2,2,2-trifluoroethyl)-1H-imidazol-4-yl)methyl)pyridine;
(S)-2,2,2-trifluoro-1-(4-(pyridin-4-ylmethyl)-1H-imidazol-2-yl)ethan-1-amine;
(R)-2,2,2-trifluoro-1-(4-(pyridin-4-ylmethyl)-1H-imidazol-2-yl)ethan-1-amine;
(S)-2,2,2-Trifluoro-N-methyl-1-(5-(pyridin-4-ylmethyl)-1H-imidazol-2-yl)ethan-1-amine;
(R)-2,2,2-Trifluoro-N-methyl-1-(5-(pyridin-4-ylmethyl)-1H-imidazol-2-yl)ethan-1-amine;
(S)-2,2,2-Trifluoro-N,N-dimethyl-1-(5-(pyridin-4-ylmethyl)-1H-imidazol-2-yl)ethan-1-amine;
(R)-2,2,2-Trifluoro-N,N-dimethyl-1-(5-(pyridin-4-ylmethyl)-1H-imidazol-2-yl)ethan-1-amine;
(E/Z)-2, 2,2-Trifluoro-1-(4-(pyridin-4-ylmethyl)thiazol-2-yl)ethan-1-one oxime;
(R)-2,2,2-Trifluoro-1-(5-(pyridin-4-ylmethyl)thiazol-2-yl)ethan-1-amine;
(S)-2,2,2-Trifluoro-1-(5-(pyridin-4-ylmethyl)thiazol-2-yl)ethan-1-amine;
(S)-(4-(Pyridin-4-ylmethyl)-1H-imidazol-2-yl)(thiazol-5-yl)methanol;
(R)-(4-(Pyridin-4-ylmethyl)-1H-imidazol-2-yl)(thiazol-5-yl)methanol;
(5-((3-Methylpyridin-4-yl)methyl)-1H-imidazol-2-yl)(thiazol-5-yl)methanol;
3,5-Dichloro-4-((2-(2,2,2-trifluoroethyl)-1H-imidazol-5-yl)methyl)pyridine;
1-(4-((3-Chloropyridin-4-yl)methyl)-1H-imidazol-2-yl)-2,2,2-trifluoroethan-1-ol;
(S)-2,2,2-trifluoro-1-(4-((S)-1-(pyridin-4-yl)ethyl)-1H-imidazol-2-yl)ethan-1-ol;
(R)-2,2,2-trifluoro-1-(4-((S)-1-(pyridin-4-yl)ethyl)-1H-imidazol-2-yl)ethan-1-ol;
(S)-2,2,2-trifluoro-1-(4-((R)-1-(pyridin-4-yl)ethyl)-1/-imidazol-2-yl)ethan-1-ol;
(R)-2,2,2-trifluoro-1-(4-((R)-1-(pyridin-4-yl)ethyl)-1H-imidazol-2-yl)ethan-1-ol;
3-Methyl-4-((2-(2,2,2-trifluoroethyl)-1H-imidazol-4-yl)methyl)pyridine;
(R)-2,2,2-Trifluoro-1-(4-(pyridin-4-ylmethyl)-1H-imidazol-2-yl)-1-(thiazol-5-yl)ethan-1-ol;
(S)-2,2,2-Trifluoro-1-(4-(pyridin-4-ylmethyl)-1H-imidazol-2-yl)-1-(thiazol-5-yl)ethan-1-ol;
3-Chloro-4-((2-(2,2,2-trifluoroethyl)-1H-imidazol-4-yl)methyl)pyridine;
2-Chloro-4-((2-(2,2,2-trifluoroethyl)-1H-imidazol-4-yl)methyl)pyridine;
2-Fluoro-4-((2-(2,2,2-trifluoroethyl)-3H-imidazol-4-yl)methyl)pyridine;
(S)-(5-((3-Methylpyridin-4-yl)methyl)-1H-imidazol-2-yl)(thiazol-5-yl)methanol;
(R)-(5-((3-Methylpyridin-4-yl)methyl)-1H-imidazol-2-yl)(thiazol-5-yl)methanol;
(R)-(5-(Pyridin-4-ylmethyl)-1H-imidazol-2-yl)(thiazol-2-yl)methanol;
(S)-(5-(Pyridin-4-ylmethyl)-1H-imidazol-2-yl)(thiazol-2-yl)methanol;
(R)-1,1,1-Trifluoro-2-(5-(pyridin-4-ylmethyl)-1H-imidazol-2-yl)propan-2-ol;
(S)-1,1,1-Trifluoro-2-(5-(pyridin-4-ylmethyl)-1H-imidazol-2-yl)propan-2-ol;
(S)-4-((2-(2,2,2-trifluoro-1-methoxyethyl)-1H-imidazol-5-yl)methyl)pyridine;
(R)-4-((2-(2,2,2-trifluoro-1-methoxyethyl)-1H-imidazol-5-yl)methyl)pyridine;
(R)-2,2,2-Trifluoro-1-(5-((2-fluoropyridin-4-yl)methyl)-1H-imidazol-2-yl)ethan-1-ol;
(S)-2,2,2-Trifluoro-1-(5-((2-fluoropyridin-4-yl)methyl)-1H-imidazol-2-yl)ethan-1-ol;
Pyridin-2-yl(5-(pyridin-4-ylmethyl)-1H-imidazol-2-yl)methanol;
3-Fluoro-4-((2-(2,2,2-trifluoroethyl)-1H-imidazol-4-yl)methyl)pyridine;
(S)-2,2,2-Trifluoro-1-(4-((3-methylpyridin-4-yl)methyl)-1H-imidazol-2-yl)ethan-1-ol;
(R)-2,2,2-Trifluoro-1-(4-((3-methylpyridin-4-yl)methyl)-1H-imidazol-2-yl)ethan-1-ol;
(S)-2,2,2-Trifluoro-1-(4-((3-fluoropyridin-4-yl)methyl)-1/-imidazol-2-yl)ethan-1-ol;
(R)-2,2,2-Trifluoro-1-(4-((3-fluoropyridin-4-yl)methyl)-1H-imidazol-2-yl)ethan-1-ol;
1,1,1,3,3,3-Hexafluoro-2-(4-(pyridin-4-ylmethyl)-1H-imidazol-2-yl)propan-2-ol; and
1,1,1-Trifluoro-2-(4-(pyridin-4-ylmethyl)-1H-imidazol-2-yl)propan-2-ol;
or a pharmaceutically acceptable salt of any of the aforementioned; wherein the neurological disorder is selected from amyotrophic lateral sclerosis (ALS), multiple sclerosis (MS), diabetic neuropathy, traumatic brain injury (TBI), ocular neuropathy, Parkinson's disease, Alzheimer's disease, and peripheral neuropathy.

19. The method of claim 1, comprising administering to the patient a further pharmaceutically active agent.

* * * * *

UNITED STATES PATENT AND TRADEMARK OFFICE
CERTIFICATE OF CORRECTION

Page 1 of 2

PATENT NO. : 12,110,285 B2
APPLICATION NO. : 18/178325
DATED : October 8, 2024
INVENTOR(S) : Rao Kolluri et al.

It is certified that error appears in the above-identified patent and that said Letters Patent is hereby corrected as shown below:

In the Claims

Column 107, Line 11:
In Claim 1, the term "$NRCS(O)R^b$" should read --$NR^cS(O)R^b$--.

Column 107, Line 11:
In Claim 1, the term "$NRCS(O)_2R^b$" should read --$NR^cS(O)_2R^b$--.

Column 107, Line 11:
In Claim 1, the term "$NRCS(O)_2NR^cR^d$" should read --$NR^cS(O)_2NR^cR^d$--.

Column 107, Line 13:
In Claim 1, the term "$Roy$" should read --$R^{Cy}$--.

Column 107, Line 22:
In Claim 1, the term "$NRCS(O)R^b$" should read --$NR^cS(O)R^b$--.

Column 107, Line 22:
In Claim 1, the term "$NRCS(O)_2R^b$" should read --$NR^cS(O)_2R^b$--.

Column 107, Line 22:
In Claim 1, the term "$NRCS(O)_2NR^cR^d$" should read --$NR^cS(O)_2NR^cR^d$--.

Column 107, Line 65:
In Claim 11, the term "$C(=NR^e)NR^cR^d$" should read --$C(=NR^e)NR^cR^d$--.

Column 107, Line 65:
In Claim 11, the term "$NR^cC(=NR^e)NR^cR^d$" should read --$NR^cC(=NR^e)NR^cR^d$--.

Signed and Sealed this
Twenty-eighth Day of January, 2025

Coke Morgan Stewart
*Acting Director of the United States Patent and Trademark Office*

CERTIFICATE OF CORRECTION (continued)
U.S. Pat. No. 12,110,285 B2

Column 107, Line 66:
In Claim 11, the term "NRCS(O)R$^b$" should read --NR$^c$S(O)R$^b$--.

Column 107, Line 66:
In Claim 11, the term "NRCS(O)$_2$R$^b$" should read --NR$^c$S(O)$_2$R$^b$--.

Column 107, Line 66:
In Claim 11, the term "NRCS(O)$_2$NR$^c$R$^d$" should read --NR$^c$S(O)$_2$NR$^c$R$^d$--.

Column 108, Line 8:
In Claim 12, the term "NRCS(O)R$^b$" should read --NR$^c$S(O)R$^b$--.

Column 108, Line 8:
In Claim 12, the term "NR$_c$S(O)$_2$R$^b$" should read --NR$^c$S(O)$_2$R$^b$--.

Column 108, Lines 8-9:
In Claim 12, the term "NRCS(O)$_2$NR$^c$R$^d$" should read --NR$^c$S(O)$_2$NR$^c$R$^d$--.

Column 108, Line 18:
In Claim 13, the term "NRCS(O)R$^b$" should read --NR$^c$S(O)R$^b$--.

Column 108, Line 18:
In Claim 13, the term "NRCS(O)$_2$R$^b$" should read --NR$^c$S(O)$_2$R$^b$--.

Column 108, Line 18:
In Claim 13, the term "NRCS(O)$_2$NR$^c$R$^d$" should read --NR$^c$S(O)$_2$NR$^c$R$^d$--.

Column 108, Line 33:
In Claim 15, the term "Roy" should read --R$^{Cy}$--.

Column 108, Line 36:
In Claim 15, the term "NRCS(O)$_2$R$^b$" should read --NR$^c$S(O)$_2$R$^b$--.